(12) United States Patent
Johns et al.

(10) Patent No.: US 9,446,418 B2
(45) Date of Patent: Sep. 20, 2016

(54) ROBOTIC ARM

(71) Applicant: Beckman Coulter, Inc., Brea, CA (US)

(72) Inventors: Charles W. Johns, Brownsburg, IN (US); Joseph F. Quint, Orange, CA (US); Chi S. Chen, Irvine, CA (US)

(73) Assignee: Beckman Coulter, Inc., Brea, CA (US)

( * ) Notice: Subject to any disclaimer, the term of this patent is extended or adjusted under 35 U.S.C. 154(b) by 775 days.

(21) Appl. No.: 13/671,440

(22) Filed: Nov. 7, 2012

(65) Prior Publication Data
US 2013/0128035 A1 May 23, 2013

Related U.S. Application Data

(60) Provisional application No. 61/556,667, filed on Nov. 7, 2011, provisional application No. 61/616,994, filed on Mar. 28, 2012, provisional application No. 61/680,066, filed on Aug. 6, 2012.

(51) Int. Cl.
*B04B 13/00* (2006.01)
*B65G 47/28* (2006.01)
(Continued)

(52) U.S. Cl.
CPC ............. *B04B 13/00* (2013.01); *B01D 21/262* (2013.01); *B04B 7/02* (2013.01); *B04B 7/08* (2013.01); *B04B 9/146* (2013.01); *B04B 15/00* (2013.01); *B25J 11/00* (2013.01); *B65D 51/24* (2013.01); *B65G 47/28* (2013.01); *G01B 11/02* (2013.01); *G01B 11/08* (2013.01); *G01B 11/10* (2013.01); *G01L 19/08* (2013.01); *G01M 1/14* (2013.01); *G01N 21/27* (2013.01); *G01N 35/0099* (2013.01); *G01N 35/00732* (2013.01); *G01N 35/04* (2013.01); *G01N 35/10* (2013.01); *G01N 35/1009* (2013.01); *B01L 3/5021* (2013.01); *B04B 2011/046* (2013.01);
(Continued)

(58) Field of Classification Search
None
See application file for complete search history.

(56) References Cited

U.S. PATENT DOCUMENTS 3,158,765 A 11/1964 Prolgreen
4,052,161 A 10/1977 Atwood et al.
(Continued)

FOREIGN PATENT DOCUMENTS

CA 1 282 692 A1 4/1991
CN 1127887 A 7/1996
(Continued)

OTHER PUBLICATIONS

International Search Report and Written Opinion mailed on Aug. 9, 2012 for PCT Patent Application No. PCT/US2012/037585, 10 pages.
(Continued)

*Primary Examiner* — Kate Luo
(74) *Attorney, Agent, or Firm* — Kilpatrick Townsend & Stockton LLP

(57) ABSTRACT

An analytical laboratory system and method for processing samples is disclosed. A sample container is transported from an input area to a distribution area by a gripper comprising a means for inspecting a tube. An image is captured of the sample container. The image is analyzed to determine a sample container identification. A liquid level of the sample in the sample container is determined. A scheduling system determines a priority for processing the sample container based on the sample container identification. The sample container is transported from the distribution area to a subsequent processing module by the gripper.

10 Claims, 29 Drawing Sheets

(51) Int. Cl.

| | | |
|---|---|---|
| *B01D 21/26* | (2006.01) | |
| *B04B 7/08* | (2006.01) | |
| *B04B 15/00* | (2006.01) | |
| *B25J 11/00* | (2006.01) | |
| *B04B 9/14* | (2006.01) | |
| *G01N 35/00* | (2006.01) | |
| *G01N 35/04* | (2006.01) | |
| *G01B 11/02* | (2006.01) | |
| *G01B 11/08* | (2006.01) | |
| *G01B 11/10* | (2006.01) | |
| *G01M 1/14* | (2006.01) | |
| *G01N 21/27* | (2006.01) | |
| *B04B 7/02* | (2006.01) | |
| *B65D 51/24* | (2006.01) | |
| *G01L 19/08* | (2006.01) | |
| *B04B 11/04* | (2006.01) | |
| *G01N 35/10* | (2006.01) | |
| *B01L 3/00* | (2006.01) | |

(52) U.S. Cl.
CPC ............... *B04B 2013/006* (2013.01); *G01N 2035/00495* (2013.01); *G01N 2035/0405* (2013.01); *G01N 2035/0462* (2013.01); *G01N 2035/0491* (2013.01); *G01N 2035/1025* (2013.01); *G01N 2035/1032* (2013.01); *Y10T 29/49826* (2015.01)

(56) References Cited

U.S. PATENT DOCUMENTS

| | | |
|---|---|---|
| 4,101,070 A | 7/1978 | Hoare et al. |
| 4,119,381 A | 10/1978 | Muka et al. |
| 4,250,266 A | 2/1981 | Wade |
| 4,401,189 A | 8/1983 | Majewski |
| 4,486,539 A | 12/1984 | Ranki et al. |
| 4,501,495 A | 2/1985 | Faulkner et al. |
| 4,530,056 A | 7/1985 | MacKinnon et al. |
| 4,593,238 A | 6/1986 | Yamamoto |
| 4,593,239 A | 6/1986 | Yamamoto |
| 4,673,657 A | 6/1987 | Christian |
| 4,674,640 A | 6/1987 | Asa et al. |
| 4,676,952 A | 6/1987 | Edelmann et al. |
| 4,683,195 A | 7/1987 | Mullis et al. |
| 4,683,202 A | 7/1987 | Mullis |
| 4,751,177 A | 6/1988 | Stabinsky |
| 4,780,817 A | 10/1988 | Lofgren |
| 4,800,159 A | 1/1989 | Mullis et al. |
| 4,851,330 A | 7/1989 | Kohne |
| 4,865,986 A | 9/1989 | Coy et al. |
| 4,943,415 A | 7/1990 | Przybylowicz et al. |
| 4,947,094 A | 8/1990 | Dyer et al. |
| 4,950,613 A | 8/1990 | Arnold, Jr. et al. |
| 5,055,393 A | 10/1991 | Kwoh et al. |
| 5,055,408 A | 10/1991 | Higo et al. |
| 5,075,853 A | 12/1991 | Luke, Jr. |
| 5,118,191 A | 6/1992 | Hopkins |
| 5,147,529 A | 9/1992 | Lee et al. |
| 5,154,888 A | 10/1992 | Zander et al. |
| 5,158,895 A | 10/1992 | Ashihara et al. |
| 5,168,766 A | 12/1992 | Stoffel |
| 5,179,329 A | 1/1993 | Nishikawa et al. |
| 5,185,439 A | 2/1993 | Arnold, Jr. et al. |
| 5,186,827 A | 2/1993 | Liberti et al. |
| 5,190,136 A | 3/1993 | Greckel et al. |
| 5,196,168 A | 3/1993 | Muszak et al. |
| 5,205,393 A | 4/1993 | Malow et al. |
| 5,229,297 A | 7/1993 | Schinpelsky et al. |
| 5,234,665 A | 8/1993 | Ohta et al. |
| 5,244,055 A | 9/1993 | Shimizu |
| 5,283,174 A | 2/1994 | Arnold et al. |
| 5,283,739 A | 2/1994 | Summerville et al. |
| 5,288,463 A | 2/1994 | Chemelli |
| 5,330,916 A | 7/1994 | Williams et al. |
| 5,350,564 A | 9/1994 | Mazza et al. |
| 5,351,801 A | 10/1994 | Markin et al. |
| 5,362,291 A | 11/1994 | Williamson, IV |
| 5,366,896 A | 11/1994 | Margrey et al. |
| 5,374,395 A | 12/1994 | Robinson et al. |
| 5,375,898 A | 12/1994 | Ohmori et al. |
| 5,380,487 A | 1/1995 | Choperena et al. |
| 5,388,682 A | 2/1995 | Dudley |
| 5,389,339 A | 2/1995 | Petschek et al. |
| 5,397,709 A | 3/1995 | Berndt |
| 5,399,491 A | 3/1995 | Kacian et al. |
| 5,403,711 A | 4/1995 | Walder et al. |
| 5,415,839 A | 5/1995 | Zuan et al. |
| 5,422,271 A | 6/1995 | Chen et al. |
| 5,427,930 A | 6/1995 | Birkenmeyer et al. |
| 5,437,990 A | 8/1995 | Burg et al. |
| 5,443,791 A | 8/1995 | Cathcart et al. |
| 5,447,687 A | 9/1995 | Lewis et al. |
| 5,449,602 A | 9/1995 | Royer et al. |
| 5,462,881 A | 10/1995 | Perlman |
| 5,466,574 A | 11/1995 | Liberti et al. |
| 5,480,784 A | 1/1996 | Kacian et al. |
| 5,482,834 A | 1/1996 | Gillespie |
| 5,504,345 A | 4/1996 | Bartunek et al. |
| 5,514,550 A | 5/1996 | Findlay et al. |
| 5,525,300 A | 6/1996 | Danssaert et al. |
| 5,527,673 A | 6/1996 | Reinhartz et al. |
| 5,536,649 A | 7/1996 | Fraiser et al. |
| 5,538,849 A | 7/1996 | Uematsu et al. |
| 5,554,516 A | 9/1996 | Kacian et al. |
| 5,563,037 A | 10/1996 | Sutherland et al. |
| 5,578,270 A | 11/1996 | Reichler et al. |
| 5,582,796 A | 12/1996 | Carey et al. |
| 5,585,242 A | 12/1996 | Bourma et al. |
| 5,585,481 A | 12/1996 | Arnold, Jr. et al. |
| 5,587,128 A | 12/1996 | Wilding et al. |
| 5,589,333 A | 12/1996 | Bagasra et al. |
| 5,602,042 A | 2/1997 | Farber |
| 5,604,130 A | 2/1997 | Warner et al. |
| 5,612,200 A | 3/1997 | Dattagupta et al. |
| 5,612,525 A | 3/1997 | Apter et al. |
| 5,623,415 A | 4/1997 | O'Bryan et al. |
| 5,628,962 A | 5/1997 | Kanbara et al. |
| 5,637,275 A | 6/1997 | Carey et al. |
| 5,639,599 A | 6/1997 | Ryder et al. |
| 5,639,604 A | 6/1997 | Arnold et al. |
| 5,641,658 A | 6/1997 | Adams et al. |
| 5,652,489 A | 7/1997 | Kawakami |
| 5,653,940 A | 8/1997 | Carey et al. |
| 5,656,493 A | 8/1997 | Mullis et al. |
| 5,665,554 A | 9/1997 | Reeve et al. |
| 5,679,553 A | 10/1997 | Van Gemen et al. |
| 5,686,272 A | 11/1997 | Marshall et al. |
| 5,702,950 A | 12/1997 | Tajima |
| 5,705,062 A | 1/1998 | Knobel |
| 5,714,380 A | 2/1998 | Neri et al. |
| 5,720,923 A | 2/1998 | Haff et al. |
| 5,723,591 A | 3/1998 | Livak et al. |
| 5,730,938 A | 3/1998 | Carbonari et al. |
| 5,735,587 A | 4/1998 | Malin et al. |
| 5,741,708 A | 4/1998 | Carey et al. |
| 5,746,978 A | 5/1998 | Bienhaus et al. |
| 5,750,338 A | 5/1998 | Collins et al. |
| 5,773,268 A | 6/1998 | Korenberg et al. |
| 5,779,981 A | 7/1998 | Danssaert et al. |
| 5,786,182 A | 7/1998 | Catanzariti et al. |
| 5,795,547 A | 8/1998 | Moser et al. |
| 5,798,263 A | 8/1998 | Wood et al. |
| 5,814,008 A | 9/1998 | Chen et al. |
| 5,814,276 A | 9/1998 | Riggs |
| 5,814,961 A | 9/1998 | Imahashi |
| 5,827,653 A | 10/1998 | Sammes et al. |
| 5,846,489 A | 12/1998 | Bienhaus et al. |
| 5,846,491 A | 12/1998 | Choperena et al. |
| 5,846,726 A | 12/1998 | Nadeau et al. |
| 5,857,955 A | 1/1999 | Phillips et al. |
| 5,866,336 A | 2/1999 | Nazarenko et al. |
| 5,881,781 A | 3/1999 | Bishop |

(56) References Cited

U.S. PATENT DOCUMENTS

| | | | |
|---|---|---|---|
| 5,882,903 | A | 3/1999 | Andrevski et al. |
| 5,895,631 | A | 4/1999 | Tajima et al. |
| 5,897,090 | A | 4/1999 | Smith et al. |
| 5,897,783 | A | 4/1999 | Howe et al. |
| 5,914,230 | A | 6/1999 | Liu et al. |
| 5,919,622 | A | 7/1999 | Macho et al. |
| 5,922,591 | A | 7/1999 | Anderson et al. |
| 5,925,517 | A | 7/1999 | Tyagi et al. |
| 5,928,907 | A | 7/1999 | Woudenberg |
| 5,948,673 | A | 9/1999 | Cottingham et al. |
| 5,966,309 | A | 10/1999 | O'Bryan et al. |
| 5,994,056 | A | 11/1999 | Higuchi et al. |
| 6,011,508 | A | 1/2000 | Perreault et al. |
| 6,033,574 | A | 3/2000 | Siddiqi |
| 6,033,880 | A | 3/2000 | Haff et al. |
| 6,043,880 | A | 3/2000 | Andrews et al. |
| 6,049,745 | A | 4/2000 | Douglas et al. |
| 6,056,106 | A | 5/2000 | van Dyke, Jr. et al. |
| 6,060,022 | A | 5/2000 | Pang et al. |
| 6,063,340 | A | 5/2000 | Lewis et al. |
| 6,068,978 | A | 5/2000 | Zaun et al. |
| 6,071,395 | A | 6/2000 | Lange |
| 6,100,079 | A | 8/2000 | Tajima |
| 6,110,676 | A | 8/2000 | Coull et al. |
| 6,110,678 | A | 8/2000 | Weisburg et al. |
| 6,117,398 | A | 9/2000 | Bienhaus et al. |
| 6,129,428 | A | 10/2000 | Helwig et al. |
| 6,150,097 | A | 11/2000 | Tyagi et al. |
| 6,165,778 | A | 12/2000 | Kedar |
| 6,171,780 | B1 | 1/2001 | Pham et al. |
| 6,212,448 | B1 | 4/2001 | Xydis |
| 6,277,332 | B1 | 8/2001 | Sucholeiki |
| 6,293,750 | B1* | 9/2001 | Cohen et al. .............. 414/744.4 |
| 6,300,068 | B1 | 10/2001 | Burg et al. |
| 6,300,138 | B1 | 10/2001 | Gleason et al. |
| 6,306,658 | B1 | 10/2001 | Turner et al. |
| 6,333,008 | B1 | 12/2001 | Leistner et al. |
| 6,335,166 | B1 | 1/2002 | Ammann et al. |
| 6,353,774 | B1 | 3/2002 | Goldenberg et al. |
| 6,368,872 | B1 | 4/2002 | Juranas |
| 6,370,452 | B1 | 4/2002 | Pfister |
| 6,374,989 | B1 | 4/2002 | van Dyke, Jr. et al. |
| 6,377,888 | B1 | 4/2002 | Olch |
| 6,429,016 | B1 | 8/2002 | McNeil |
| 6,436,349 | B1 | 8/2002 | Carey et al. |
| 6,444,171 | B1 | 9/2002 | Sakazume et al. |
| RE37,891 | E | 10/2002 | Collins et al. |
| 6,458,324 | B1 | 10/2002 | Schinzel |
| 6,520,313 | B1 | 2/2003 | Kaarakainen et al. |
| 6,548,026 | B1 | 4/2003 | Dales et al. |
| 6,586,234 | B1 | 7/2003 | Burg et al. |
| 6,586,255 | B1 | 7/2003 | Hubert et al. |
| 6,597,450 | B1 | 7/2003 | Andrews et al. |
| 6,599,476 | B1 | 7/2003 | Watson et al. |
| 6,605,213 | B1 | 8/2003 | Ammann et al. |
| 6,629,028 | B2 | 9/2003 | Paromtchik et al. |
| 6,633,785 | B1 | 10/2003 | Kasahara et al. |
| 6,692,708 | B2 | 2/2004 | Chandler, Jr. |
| 6,764,649 | B2 | 7/2004 | Ammann |
| 6,770,883 | B2 | 8/2004 | Mc Neal et al. |
| 6,818,183 | B2 | 11/2004 | Hajduk et al. |
| 6,890,742 | B2 | 5/2005 | Ammann et al. |
| 6,919,058 | B2 | 7/2005 | Andersson et al. |
| 6,919,175 | B1 | 7/2005 | Bienhaus et al. |
| 6,941,200 | B2 | 9/2005 | Sonoyama et al. |
| 6,993,176 | B2 | 1/2006 | Yamagishi et al. |
| 6,999,847 | B2 | 2/2006 | Barry et al. |
| 7,028,831 | B2 | 4/2006 | Veiner |
| 7,033,820 | B2 | 4/2006 | Ammann et al. |
| 7,045,358 | B2 | 5/2006 | Chandler, Jr. |
| 7,071,006 | B2 | 7/2006 | Tajima et al. |
| 7,078,698 | B2 | 7/2006 | Itoh |
| 7,118,892 | B2 | 10/2006 | Ammann et al. |
| 7,135,145 | B2 | 11/2006 | Ammann et al. |
| 7,174,836 | B2 | 2/2007 | Marino et al. |
| 7,264,111 | B2 | 9/2007 | Veiner |
| 7,267,795 | B2 | 9/2007 | Ammann et al. |
| 7,269,480 | B2 | 9/2007 | Hashimoto et al. |
| 7,273,749 | B1 | 9/2007 | Wittwer et al. |
| 7,288,229 | B2 | 10/2007 | Turner et al. |
| 7,362,258 | B2 | 4/2008 | Kawabe et al. |
| 7,419,830 | B2 | 9/2008 | Canos et al. |
| 7,463,948 | B2 | 12/2008 | Orita |
| 7,473,897 | B2 | 1/2009 | Braendle et al. |
| 7,482,143 | B2 | 1/2009 | Ammann et al. |
| 7,499,581 | B2 | 3/2009 | Tribble et al. |
| 7,524,652 | B2 | 4/2009 | Ammann et al. |
| 7,560,255 | B2 | 7/2009 | Ammann et al. |
| 7,560,256 | B2 | 7/2009 | Ammann et al. |
| 7,688,448 | B2 | 3/2010 | Bamberg et al. |
| 7,771,659 | B2 | 8/2010 | Ziegler |
| 8,074,578 | B2 | 12/2011 | Thornton |
| 8,192,992 | B2 | 6/2012 | Ammann et al. |
| 2002/0025064 | A1 | 2/2002 | Itoh |
| 2002/0028489 | A1 | 3/2002 | Ammann et al. |
| 2002/0031768 | A1 | 3/2002 | McMillan et al. |
| 2002/0077239 | A1 | 6/2002 | Evans, III et al. |
| 2002/0086417 | A1 | 7/2002 | Chen |
| 2002/0098117 | A1 | 7/2002 | Ammann et al. |
| 2002/0123156 | A1 | 9/2002 | Tajima |
| 2002/0132286 | A1* | 9/2002 | Downs ........................ 435/41 |
| 2002/0137194 | A1 | 9/2002 | Ammann et al. |
| 2002/0137197 | A1 | 9/2002 | Ammann et al. |
| 2002/0146347 | A1 | 10/2002 | McNeil |
| 2002/0147515 | A1 | 10/2002 | Fava et al. |
| 2003/0026736 | A1 | 2/2003 | Hajduk et al. |
| 2003/0027206 | A1 | 2/2003 | Ammann et al. |
| 2003/0033896 | A1* | 2/2003 | Borowczak et al. ........... 73/866 |
| 2003/0054542 | A1 | 3/2003 | Burns et al. |
| 2003/0129611 | A1 | 7/2003 | Parameswaran et al. |
| 2003/0190755 | A1 | 10/2003 | Turner et al. |
| 2003/0213313 | A1 | 11/2003 | Katagi |
| 2003/0223916 | A1 | 12/2003 | Testrut et al. |
| 2004/0029260 | A1 | 2/2004 | Hansen et al. |
| 2004/0076983 | A1 | 4/2004 | Karlsen |
| 2004/0087426 | A1 | 5/2004 | Lattanzi |
| 2004/0115796 | A1 | 6/2004 | Burns |
| 2004/0158355 | A1 | 8/2004 | Holmqvist et al. |
| 2004/0184959 | A1 | 9/2004 | Itoh |
| 2004/0206419 | A1 | 10/2004 | Ganz et al. |
| 2004/0213651 | A1 | 10/2004 | Malin |
| 2005/0130198 | A1 | 6/2005 | Ammann et al. |
| 2005/0158212 | A1 | 7/2005 | Yavilevich |
| 2005/0163354 | A1 | 7/2005 | Ziegler |
| 2005/0207937 | A1 | 9/2005 | Itoh |
| 2005/0220670 | A1 | 10/2005 | Palmieri et al. |
| 2005/0233370 | A1 | 10/2005 | Ammann et al. |
| 2005/0239127 | A1 | 10/2005 | Ammann et al. |
| 2005/0266489 | A1 | 12/2005 | Ammann et al. |
| 2005/0271555 | A1 | 12/2005 | Itoh |
| 2006/0003373 | A1 | 1/2006 | Ammann et al. |
| 2006/0014295 | A1 | 1/2006 | Ziegler |
| 2006/0020370 | A1 | 1/2006 | Abramson |
| 2006/0148063 | A1 | 7/2006 | Fauzi et al. |
| 2006/0228268 | A1 | 10/2006 | Heimberg et al. |
| 2007/0044676 | A1 | 3/2007 | Clark et al. |
| 2007/0059209 | A1 | 3/2007 | Pang et al. |
| 2007/0100498 | A1 | 5/2007 | Matsumoto et al. |
| 2007/0110634 | A1 | 5/2007 | Heimberg et al. |
| 2007/0134131 | A1 | 6/2007 | Watson et al. |
| 2007/0179690 | A1 | 8/2007 | Stewart |
| 2007/0184548 | A1 | 8/2007 | Tan et al. |
| 2007/0193859 | A1 | 8/2007 | Kyuyoku et al. |
| 2007/0196237 | A1 | 8/2007 | Neuzil et al. |
| 2007/0208440 | A1 | 9/2007 | Bliss et al. |
| 2007/0225901 | A1 | 9/2007 | Yamaguchi |
| 2007/0225906 | A1 | 9/2007 | Ikeda |
| 2008/0014181 | A1 | 1/2008 | Ariff et al. |
| 2008/0015470 | A1 | 1/2008 | Sarstedt |
| 2008/0056958 | A1 | 3/2008 | Vijay et al. |
| 2008/0069730 | A1 | 3/2008 | Itoh |
| 2008/0138249 | A1 | 6/2008 | Itoh |
| 2008/0167817 | A1 | 7/2008 | Hessler et al. |
| 2008/0241837 | A1 | 10/2008 | Ammann et al. |

(56) References Cited

U.S. PATENT DOCUMENTS

| | | | |
|---|---|---|---|
| 2008/0255683 A1 | 10/2008 | Takahashi et al. |
| 2008/0268528 A1 | 10/2008 | Ammann et al. |
| 2008/0274511 A1 | 11/2008 | Tan et al. |
| 2008/0297769 A1 | 12/2008 | Bamberg et al. |
| 2009/0029352 A1 | 1/2009 | Ammann et al. |
| 2009/0029871 A1 | 1/2009 | Ammann et al. |
| 2009/0029877 A1 | 1/2009 | Ammann et al. |
| 2009/0030551 A1 | 1/2009 | Hein et al. |
| 2009/0035185 A1 | 2/2009 | Tsujimura et al. |
| 2009/0042281 A1 | 2/2009 | Chang et al. |
| 2009/0047179 A1 | 2/2009 | Ping et al. |
| 2009/0117620 A1 | 5/2009 | Fritchie et al. |
| 2009/0318276 A1 | 12/2009 | Miler |
| 2009/0324032 A1 | 12/2009 | Chen |
| 2010/0018330 A1 | 1/2010 | Marty et al. |
| 2010/0115887 A1 | 5/2010 | Schroeder et al. |
| 2010/0129789 A1 | 5/2010 | Self et al. |
| 2010/0141756 A1 | 6/2010 | Grote et al. |
| 2010/0261595 A1 | 10/2010 | Schaefer et al. |
| 2010/0291619 A1 | 11/2010 | Robinson et al. |
| 2011/0065193 A1 | 3/2011 | Kitagawa et al. |
| 2011/0226584 A1 | 9/2011 | Ek |
| 2012/0129673 A1 | 5/2012 | Fukugaki et al. |
| 2013/0123089 A1 | 5/2013 | Johns et al. |
| 2013/0125675 A1 | 5/2013 | Mueller et al. |
| 2013/0126302 A1 | 5/2013 | Johns et al. |
| 2013/0129166 A1 | 5/2013 | Mueller et al. |

FOREIGN PATENT DOCUMENTS

| | | |
|---|---|---|
| CN | 1164894 A | 11/1997 |
| CN | 1212019 A | 3/1999 |
| CN | 1212021 A | 3/1999 |
| CN | 1245218 A | 2/2000 |
| CN | 1281462 A | 1/2001 |
| CN | 1974781 A | 6/2007 |
| CN | 101379403 A | 3/2009 |
| CN | 102023227 A | 4/2011 |
| DE | 35 10 797 C2 | 1/1988 |
| DE | 696 33 532 T2 | 2/2006 |
| EP | 0 324 616 A2 | 7/1989 |
| EP | 0 328 829 A2 | 8/1989 |
| EP | 0 410 645 A2 | 1/1991 |
| EP | 0 479 448 A2 | 4/1992 |
| EP | 0 502 589 A2 | 9/1992 |
| EP | 0 502 638 A2 | 9/1992 |
| EP | 0 542 422 A1 | 5/1993 |
| EP | 0 574 267 A2 | 12/1993 |
| EP | 0 574 267 A3 | 12/1993 |
| EP | 0 622 457 A1 | 2/1994 |
| EP | 0 600 130 A2 | 6/1994 |
| EP | 0 687 501 B1 | 12/1995 |
| EP | 0 656 864 B1 | 3/1996 |
| EP | 0 727 665 A2 | 8/1996 |
| EP | 0 763 739 A1 | 3/1997 |
| EP | 0 819 641 A2 | 1/1998 |
| EP | 0 875 584 A2 | 4/1998 |
| EP | 0 843 176 A1 | 5/1998 |
| EP | 0 680 883 B1 | 12/1998 |
| EP | 0 889 328 A | 7/1999 |
| EP | 0 953 838 A1 | 11/1999 |
| EP | 0 640 828 B1 | 5/2000 |
| EP | 1 069 942 B1 | 1/2001 |
| EP | 1 075 328 B1 | 2/2001 |
| EP | 0 875 584 A3 | 5/2001 |
| EP | 0 752 971 B1 | 6/2001 |
| EP | 1 205 756 A2 | 5/2002 |
| EP | 1 248 170 B1 | 10/2002 |
| EP | 1 273 919 A1 | 1/2003 |
| EP | 0 687 502 B1 | 3/2003 |
| EP | 1 288 758 B1 | 3/2003 |
| EP | 1 326 077 B1 | 9/2004 |
| EP | 1 557 961 A1 | 7/2005 |
| EP | 1 712 971 A2 | 10/2006 |
| EP | 1 712 971 A3 | 10/2006 |
| EP | 1 398 729 B1 | 10/2007 |
| EP | 1 024 355 B1 | 3/2008 |
| EP | 0 885 958 B1 | 6/2008 |
| EP | 1 138 784 B1 | 10/2008 |
| EP | 1 623 764 B1 | 2/2009 |
| EP | 1 614 470 B1 | 3/2009 |
| EP | 1 721 671 B1 | 10/2009 |
| EP | 1 731 222 B1 | 3/2010 |
| EP | 2 295 144 A | 3/2011 |
| EP | 2 316 570 A2 | 5/2011 |
| EP | 2 316 571 A2 | 5/2011 |
| EP | 2 316 572 A2 | 5/2011 |
| EP | 2 148 205 B1 | 1/2013 |
| GB | 2 101 514 A | 1/1983 |
| GB | 2 203 243 A | 10/1988 |
| JP | 62-148858 A | 7/1987 |
| JP | 01-211500 A1 | 8/1989 |
| JP | 02-025754 A2 | 1/1990 |
| JP | 05-184397 A | 7/1993 |
| JP | 05-219933 A | 8/1993 |
| JP | 05-281239 A | 10/1993 |
| JP | 06-011512 A | 1/1994 |
| JP | 06-197797 A | 7/1994 |
| JP | 06-327476 A | 11/1994 |
| JP | 07-049346 A | 2/1995 |
| JP | 07-75544 A | 3/1995 |
| JP | 07-191042 A | 7/1995 |
| JP | 07-213586 A | 8/1995 |
| JP | 07-107999 B2 | 11/1995 |
| JP | 07-301637 A | 11/1995 |
| JP | 07-333230 A | 12/1995 |
| JP | 08-9957 A | 1/1996 |
| JP | 08-62224 A | 3/1996 |
| JP | 08-211071 A | 8/1996 |
| JP | 08-285857 A | 11/1996 |
| JP | 08-286749 A | 11/1996 |
| JP | 08-320274 A | 12/1996 |
| JP | 09-021805 A | 1/1997 |
| JP | 09-080056 A | 3/1997 |
| JP | 09-089902 A | 4/1997 |
| JP | 09-89907 A | 4/1997 |
| JP | 09-121899 A | 5/1997 |
| JP | 09-329602 A | 12/1997 |
| JP | 10-062426 A | 3/1998 |
| JP | 11-503315 A | 3/1999 |
| JP | 2000-500331 A | 1/2000 |
| JP | 3007571 B2 | 2/2000 |
| JP | 2001-503730 A | 3/2001 |
| JP | 2002-296286 A | 10/2002 |
| JP | 2006-317330 A | 11/2006 |
| JP | 2007-249632 A | 9/2007 |
| JP | 2008-032652 A2 | 2/2008 |
| JP | 4511034 A | 5/2010 |
| JP | 4662580 A | 3/2011 |
| WO | 88/01302 A1 | 2/1988 |
| WO | 88/10315 A1 | 12/1988 |
| WO | 89/02476 A1 | 3/1989 |
| WO | 90/06042 A2 | 6/1990 |
| WO | 90/08840 A1 | 8/1990 |
| WO | 91/15768 A1 | 10/1991 |
| WO | 91/16675 A1 | 10/1991 |
| WO | 93/07292 A1 | 4/1993 |
| WO | 93/25912 A2 | 12/1993 |
| WO | 93/25912 A3 | 12/1993 |
| WO | 93/25913 A1 | 12/1993 |
| WO | 95/08774 A2 | 3/1995 |
| WO | 95/11454 A1 | 4/1995 |
| WO | 95/21382 A2 | 8/1995 |
| WO | 95/30139 A1 | 11/1995 |
| WO | 95/35390 A1 | 12/1995 |
| WO | 96/29602 A1 | 9/1996 |
| WO | 96/31781 A1 | 10/1996 |
| WO | 96/40990 A1 | 12/1996 |
| WO | 97/03348 A1 | 1/1997 |
| WO | 97/05492 A1 | 2/1997 |
| WO | 97/16561 A1 | 5/1997 |
| WO | 97/22882 A1 | 6/1997 |
| WO | 97/31105 A1 | 8/1997 |
| WO | 97/34908 A1 | 9/1997 |

(56) References Cited

FOREIGN PATENT DOCUMENTS

| | | |
|---|---|---|
| WO | 97/46707 A2 | 12/1997 |
| WO | 98/18008 A1 | 4/1998 |
| WO | 99/25476 A2 | 5/1999 |
| WO | 99/28724 A1 | 6/1999 |
| WO | 99/57561 A2 | 11/1999 |
| WO | 00/08472 A2 | 2/2000 |
| WO | 00/08472 A3 | 2/2000 |
| WO | 00/15481 A | 3/2000 |
| WO | 00/38046 A1 | 6/2000 |
| WO | 00/67547 A2 | 11/2000 |
| WO | 01/44510 A2 | 6/2001 |
| WO | 03/046412 A1 | 6/2003 |
| WO | 03/097808 A2 | 11/2003 |
| WO | 2004/013640 A1 | 2/2004 |
| WO | 2006/021052 A1 | 3/2006 |
| WO | 2006/068470 A1 | 6/2006 |
| WO | 2007/094744 A1 | 8/2007 |
| WO | 2008/030914 A2 | 3/2008 |
| WO | 2008/043393 A1 | 4/2008 |
| WO | 2008/057375 A2 | 5/2008 |
| WO | 2008/067847 A1 | 6/2008 |
| WO | 2009/068555 A1 | 6/2009 |
| WO | 2009/067263 A1 | 8/2009 |
| WO | 2009/150632 A2 | 12/2009 |
| WO | 2009/150632 A3 | 12/2009 |
| WO | 2010/017528 A2 | 2/2010 |
| WO | 2010/080340 A1 | 7/2010 |
| WO | 2010/081606 A1 | 7/2010 |
| WO | 2011/013701 A1 | 2/2011 |
| WO | 2011/028166 A1 | 3/2011 |
| WO | 2012/090795 A1 | 7/2012 |
| WO | 2012/158541 A1 | 11/2012 |

OTHER PUBLICATIONS

Abe et al., "Quantitation of Hepatitis B Virus Genomic DNA by Real-Time Detection PCR," J. Clin. Microbiol., 1999, 37(9):2899-2903, American Society for Microbiology, Washington D.C., USA.

ABI PRISM® 373 DNA Sequencer With XL Upgrade—User's Manual, Mar. 2001, TOC-iii—TOC-v & 6-11—6-16, Applied Biosystems, USA.

Abravaya, "Strategies to Avoid Amplicon Contamination," in Nucleic Acid Amplification Technologies: Application to Disease Diagnosis, 1997, pp. 125-133, Eaton Pub. Co., Natick, USA.

Akane, "Identification of the heme compound copurified with deoxyribonucleic acid (DNA) from bloodstains, a major inhibitor of polymerase chain reaction (PCR) amplification", J. Forensic Sci., 1994, 39:362-72, Blackwell Pub., USA.

Akduman et al., "Evaluation of a Strand Displacement Amplification Assay (BD ProbeTec-SDA) for Detection of Neisseria gonorrhoeae in Urine Specimens," J. Clin. Microbiol., 2002, 40(1):281-282, American Society for Microbiology, Washington D.C., USA.

Amplification Technical Bulletin, "Comparison of TMA with PCR and LCR Amplification Methods," undated, Gen-Probe Incorporated, San Diego, USA, 1 page.

Analog Device; "±5 g to ±5 g, Low Noise, Low Power, Single/Dual Axis / MEMS ® Accelerometers,"; http://hibp.ecse.rpi.edu/~connor.education/ElSpecs/ADXL150_250_0.pdf;; Jan. 1, 1998; pp. 1-15.

Anderson et al., "Microfluidic Biochemical Analysis System," Transducers, International Conference on Solib-Slate Sensors and Actuators, Jun. 16-19, 1997, p. 477-480, IEEE Electron Devices Society, Piscataway, USA.

Armstrong et al., 1996, "Automated high throughput RT-PCR," Laboratory Robotics and Automation 8:311-315, VCH Publishers, USA.

Astle, "Standards in Robotics and Instrucmentation," Society Updates, Working Group Updates, and Conference Highlights, J. Biomol. Screen., 1996, 1(4):161-172, Sage Publications, USA.

Bailey et al., "Robotic Nucleic Acid Isolation Using a Magnetic Bead Resin and an Automated Liquid Handler for Biological Agent Simulants,", JALA, Dec. 2003, 8:113-120.

Bassam. "Nucleic Acid Sequence Detection Systems: Revolutionary Automation for Monitoring and Reporting PCR Products" Australasian Biotechnology, 1996, 6:285-294, Australian Biotechnology Association, Australia.

Belgrader et al., "Automated DNA Purification and Amplification from Blood-Stained Cards Using a Robotic Workstation," Short Technical Reports, Biotechniques, 1995, 19(9):426-432, Informa Healthcare USA, Inc., UK.

Belgrader et al., "Automated Polymerase Chain Reaction Product Sample Preparation for Capillary Electrophoresis Analysis," J. Chromatogr. B Biomed. Appl., 1996, 683:109-114, Elsevier Science, Amsterdam, Netherlands.

Belgrader et al., "Automated Sample Processing Using Robotics for Genetic Typing of Short Tandem Repeat Polymorphisms by Capillary Electrophoresis," Laboratory Robotics and Automation, 1997, 9:3-7, Wiley & Sons Inc., USA.

Borst et al., "False-Positive Results and Contamination in Nucleic Acid Amplification Assays: Suggestions for a Prevent and Destroy Strategy," Eur. J. Clin. Microbiol. Infect Dis., 2004, 23:289-299, Springer-Verlag, Berlin, Germany.

Boyd et al., "Robotics and the changing face of the clinical laboratory," Clin. Chem., 1996, 42(12):1901-1910, Washington DC American Association for Clinical Chemistry, USA.

Brochure, "Amplified Mycobacteria Direct Tests," undated, Gen-Probe Incorporated, San Diego, USA, 6 pages.

Brochure, "Introducing the Amplified Mycobacterium Tuberculosis Direct (MTD) Test from Gen-Probe," Oct. 1996, Gen-Probe Incorporated, San Diego, USA, 2 pages.

Brochure, "The Future of Amplification Technology has Arrived," Oct. 1995, Gen-Probe Incorporated, San Diego, USA, 4 pages.

Buhlmann et al., "An Open Software Environment to Optimize the Productivity of Robotized Laboratories," J. Chromatogra. Sci., 1994, 32:243-248, Preston Technical Abstracts, Niles, USA.

Bush et al., "Detection of human immunodeficiency virus type 1 RNA in plasma samples from high-risk pediatric patients by using the self-sustained sequence replication reaction," J. Clin. Microbiol., 1992, 30(2):281-286, American Society for Microbiology, Washington D.C., USA.

Butler et al., "Forensic DNA typing by capillary electrophoresis using the ABI Prism 310 and 3100 genetic analyzers for STR analysis," Electrophoresis, 2004, 25:1397-1412, Wiley-VCH Verlag GmbH & Co. KGaA, Germany.

Caprari, G. et al.; "The autonomous Micro Robot "Alice": a platform for scientific and commercial applications"; *Proceedings of the 1998 International Symposium on Micromechatronics and Human Science*, Nagoya, Japan; Nov. 25-28 1998; pp. 1-5.

Carlson et al., "Laboratory Detection of Chlamydia trachomatis, Neisseria gonorrhoeae, and Other Sexually-Transmitted Agents," 97th General Meeting of the American Society for Microbiology, C-308, May 4-8, 1997, Miami Beach, USA.

Carrino et al., "Nucleic Acid Amplification Methods," J. Micorbiol. Methods, 1995, 23:3-20.

Check, "Real-time PCR for the rest of us," CAP Today, Jun. 2006, College of American Pathologists, Skokie, IL, USA, 6 pages.

Chemistry Guide, "Automated Dna Sequencing," PE Applied Biosystems, 1998, pp. 1-4~1-6, The Perkin-Elmer Corporation.

Cimino et al., "Post-PCR sterilization: a method to control carry-over contamination for the polymerase chain reaction," Nucleic Acids Res., 1991, 19(1):99-107, Oxford University Press, Oxford, United Kingdom.

Clewley, "Automation of the Polymerase Chain Reaction Part 2. Extraction—The Foundation for Success," Communicable Disease and Public Health, Jun. 1999, 2(2):147-148, Public Health Laboratory Service in association with the Scottish Centre for Infection and Environmental Health, London, United Kingdom.

Corkan et al., "Experiment Manager Software for an Automated Chemistry Workstation, Including a Scheduler for Parallel Experimentation," Chemometrics and Intelligent Laboratory Systems: Laboratory Information Management, 1992, 17:47-74, Elsevier Science Publishers, Amsterdam, Netherlands.

Corrected Request for Inter Partes Reexamination of U.S. Pat. No. 7,482,143, filed on Sep. 14, 2012, 121 pages.

(56) References Cited

OTHER PUBLICATIONS

Crotchfelt et al., "Detection of Chlamydia trachomatis by the Gen-Probe Amplified Chlamydia Trachomatis Assay (AMP CT) in Urine Specimens from Men and Women and Endocervical Specimens from Women," J. Clin. Microbiol., Feb. 1998, 36(2):391-394, American Society for Microbiology, Washington D.C., USA.

Davis et al., "Amplification of DNA Using the Polymerase Chain Reaction," in Basic Methods in Molecular Biology, 2nd ed., 1994, p. 121, Appleton & Lange, Norwalk, USA.

Diamandis, "Automation of molecular diagnostics," Clinical Chemistry, 1996, 42:7-8, American Association for Clinical Chemistry, USA.

DiDomenico et al., "COBAS AMPLICOR™: fully automated RNA and DNA amplification and detection system for routine diagnostic PCR," Clin. Chem., 1996, 42(12):1915-1923, Washington DC American Association for Clinical Chemistry, USA.

Dieffenbach et al., "Setting Up a PCR Laboratory," Genome Rsearch, PCR Methods and Applications, 1993, 3:s2-s7, Cold Spring Harbor Laboratory, Cold Spring Harbor, USA.

Dragon, "Handling Reagents in the PCR Laboratory," Genome Research, PCR Methods and Applications, 1993, 3:s8-s9, Cold Spring Harbor Laboratory, Cold Spring Harbor, USA.

Dynal®, Technical Handbook. Molecular Biology, First Edition. "Dynabeads® biomagnetic separation system," 1992, 4 pages, Dynal AS, Norway.

Erlich, "PCR Technology," in Encyclopedia of Molecular Biology and Molecular Medicine: Mass Spectrometry High Speed DNA Fragment Sizing to Plasma Lipoproteins, vol. 4, 1996, p. 337, VCH Verlagsgesellschaft mbH, Weinheim, Germany.

Espy et al., "Dependence of polymerase chain reaction product inactivation protocols on amplicon length and sequence composition," J. Clin. Microbiol., 1993, 31(9):2361-2365, American Society for Microbiology, Washington D.C., USA.

Farrell, Jr., "RT PCR" in RNA Method: A Laboratory Guide for Isolation and Characterization, 1998, 2nd ed., Chapter 15, pp. 296-307, Academic Press, San Diego, California, USA.

Feinberg, "A Technique for Radiolabeling DNA Restriction Endonuclease Fragments to High Specific Activity", Analytical Biochemistry, 1983, 132:6-13, Academic Press, USA.

Findlay et al., "Automated Closed-Vessel System for in Vitro Diagnostics Based on Polymerase Chain Reaction," Clin. Chem., 1993, 39(9):1927-1933, American Association for Clinical Chemistry, Washington, D.C., USA.

Fiore et al., "The Abbott IMx automated benchtop immunochemistry analyzer system," Clin. Chem., 1988, 34 (9):1726-32, American Association for Clinical Chemistry, Washington D.C., USA.

FLEXLINK®; "TX45E puck handling (mx. 250g),"; located at http://www.flexlink.com/en/offering/conveyor-systems/pallet-and-puck-handling/x45e.jsp; last visited on Jul. 20, 2013; 2 pages.

Friendenberg et al., "Developing a fully automated instrument for molecular diagnostic assays," IVD Technology, 2005, 11(6), 6 pages, A Canon Communications, Los Angeles, USA.

Furrows et al., "'Good laboratory practice' in diagnostic laboratories using nucleic acid amplification methods," Clin. Microbiol. Infect., 2001, 7(5):227-229, Blackwell Science, Oxford, United Kingdom.

Gelmini et al., "Quantitative polymerase chain reaction-based homogeneous assay with fluorogenic probes to measure c-erbB-2 oncogene amplification," Clin. Chem., 1997, 43(5):752-758, American Association for Clinical Chemistry, Washington D.C., USA.

Gerber et al., "Differential Transcriptional Regulation of the Two Vascular Endothelial Growth Factor Receptor Genes," J. Biol. Chem., 1997, 272(38):23659-23667, The American Society for Biochemistry and Molecular Biology, Baltimore, USA.

Gibson et al., "A homogenous method for genotyping with fluorescence polarization," Clin. Chem., 1997, 43(8):1336-1341, American Association for Clinical Chemistry, Washington D.C., USA.

Gibson et al., "A novel method for real time quantitative RT-PCR," Genome Methods, 1996, 6:995-1001, Cold Spring Harbor Laboratory Press, Cold Spring Harbor, USA.

Giesendorf et al., "Molecular beacons: a new approach for semiautomated mutation analysis," Clin. Chem., 1998, 44(3):482-486, American Association for Clinical Chemistry, Washington D.C., USA.

Gilgen et al., "Hydroxyquinoline overcomes PCR inhibition by UV-damaged mineral oil," Nucleic Acids Res., 1995, 23(19):4001-4002, Oxford University Press, Oxford, United Kingdom.

Ginocchio, "Life Beyond PCR: Alternative Target Amplification Technologies for the Diagnosis of Infectious Diseases, Part II," Clinical Microbiology Newsletter, 2004, 26(17):129-136, Elsevier Science, New York, USA.

Godfrey-Faussett, "Molecular Diagnosis of Tuberculosis: The Need for New Diagnostic Tools," Thorax, 1995, 50(7):709-711, British Medical Association, London, United Kingdom.

Greenstein, "Preparing and Using M13-Derived Vectors," Current Protocols in Molecular Biology, published 1990, §1.151 and 1.15.4, J. Wiley and Sons, USA.

Haas, "Clinical Instrumentation (General Chemistry and Immunoassay Analyzers)," Anal. Chem., 1993, 65(12):444R-449R, American Chemical Society, Washington D.C., USA.

Haglund et al., "Polymerase Chain Reaction," in Forensic Taphonomy: the Postmortem Fate of Human Remains, 1997, p. 114-115, CRC Press LLC, Boca Raton, USA.

Hartley et al., "Dealing with Contamination: Enzymatic Control of Carryover Contamination in PCR," Genome Research, PCR Methods and Applications, 1993, 3:s10-s14, Cold Spring Harbor Laboratory, Cold Spring Harbor, USA.

Hawker, "Laboratory Automation: Total and Subtotal," Clin. Lab. Med., 2007, 27:749-770, Elsevier Health Sciences Division, Philadelphia, USA.

Hawkes et al., "Asymptomatic carriage of *Haemophilus ducreyi* confirmed by the polymerase chain reaction," J. Genitourin. Med., 1995, 71:224-227.

Hawkins et al., "A Magnetic Attraction to High-Throughput Genomics," Science, 1997, 276:1887 & 1889 (p. 1888 omitted—advertisement only), Washington, DC: American Association for the Advancement of Science, USA.

Hedrum et al., "Immunomagnetic Recovery of *Chlamydia trachomatis* from Urine with Subsequent Colorimetric DNA Detection," PCR Methods Appl., 1992, 2:167-171, Cold Spring Harbor Laboratory Press, Cold Spring Harbor, USA.

Heid et al., "Real Time Quantitative PCR," Genome Research, 1996, 6:986-994, Cold Spring Harbor Laboratory Press, Cold Spring Harbor, USA.

Hellyer et al., "Letter to the Editor: Specificity of IS6110-Based Amplification Assays for Mycobacterium tuberculosis Complex," J. Clin. Microbiol., 1997, 35(3):799-801, American Society for Microbiology, Washington D.C., USA.

Herring et al., "Elisa Automation: A Biomek 1000 to Biomek 2000 Comparison of Clinical ELISAs", Application Information, 1995, Beckman Industries, Inc., USA.

Herrmann et al., "General Aspects of Sample Preparation," in Ancient DNA: Recovery and Analysis of Genetic Material from Paleontological, Archaeological, Museum, Medical, and Forensic Specimens, 1994, pp. 63-64, Springer-Verlag, New York City, USA.

Hicks et al., "Beckman/Sagian "Core" Molecular Biology System,", T-1845A, Beckman Instruments, Inc., 1997, 4 pages.

Higuchi et al., "Simultaneous Amplification and Detection of Specific DNA Sequences," Bio/Technology, 1992, 10:413-417, Nature Publishing Company, New York, USA.

Hildebrandt et al., Development of an Automated Sample Preparation Method for HCV, J. Microbiol. Methods, 1997, 30:235-253, Abstract 17, 1 page, Elsevier Biomedical, Amsterdam, Netherlands.

Hill, "Gen-Probe Transcription-Mediated Amplification: System Principles," Jan. 1996, Gen-Probe Incorporated, San Diego, USA, 4 pages.

Hill, "How Full Automation of Molecular Diagnostic Testing Can Increase Accuracy, Lab Efficiency, Cost Savings," Issue Stories, Jul. 2004, 3 pages, Clinical Lab Products, Los Angeles, USA.

(56) References Cited

OTHER PUBLICATIONS

Hill, "Molecular diagnostic testing for infectious diseases using TMA technology," Expert Rev. Mol. Diagn., 2001, 1 (4):445-455, Future Drugs Ltd., London, United Kingdom.
Hill, "Molecular Diagnostic Tests for Sexually Transmitted Infections in Women," in Infectious Diseases in Obstetrics and Gynecology, 2008, 6th ed., pp. 612-623, Informa plc, St. Helier, Jersey.
Hill, "Molecular Diagnostics for Infectious Diseases," J. Clin. Ligand Assay, 1996, 19(1):43-52, Clinical Ligand Assay Society, Wayne, Michigan, USA.
Hoad et al., "Virus Genome Detection by the PCR," in Practical Molecular Virology: Viral Vectors for Gene Expression, 1991, pp. 75-76, Humana Press, Totowa, USA.
Holland et al., "Detection of specific polymerase chain reaction product by utilizing the 5'→ 3' exonuclease activity of Thermus aquaticus DNA polymerase," Biochemistry, 1991, 88:7276-7280, Proc. Natl. Acad. Sci. USA, Washington D.C., USA.
International Search Report and Written Opinion mailed on Feb. 15, 2013 for PCT Application No. PCT/US2012/063923, 12 pages.
International Search Report and Written Opinion mailed on Feb. 15, 2013 for PCT Application No. PCT/US2012/063914, 9 pages.
International Search Report and Written Opinion mailed on Jun. 12, 2013 for PCT Patent Application No. PCT/US2012/063888, 18 pages.
International Search Report and Written Opinion mailed on Mar. 19, 2013 for PCT Application No. PCT/US2012/063929, 13 pages.
International Search Report and Written Opinion mailed on Dec. 7, 2012 for PCT Patent Application No. PCT/US2011/045107, 18 pages.
International Search Report and Written Opinion mailed on Oct. 4, 2013 for PCT Patent Application No. PCT/US2012/063931, 24 pages.
International Search Report and Written Opinion mailed on Sep. 30, 2013 for PCT Patent Application No. PCT/US2012/063930, 37 pages.
Invitation to Pay Additional Fees mailed on Mar. 1, 2013 for PCT Patent Application No. PCT/US2012/063918, 6 pages.
Invitation to Pay Additional Fees mailed on Mar. 19, 2013 for PCT Patent Application No. PCT/US2012/063930, 8 pages.
Invitation to Pay Additional Fees mailed on Mar. 25, 2013 for PCT Patent Application No. PCT/US2012/063931, 8 pages.
Invitation to Pay Additional Fees mailed on Mar. 6, 2013 for PCT Patent Application no. PCT/US2012/063888, 6 pages.
Invitrogen; Manual, "Dynabeads® DNA DIRECT™ Blood" Cat. No,. 631.02 "For the isolation of PCR-ready genomic DNA from blood" Rev. o. 006, Invitrogen, *Dynal® Invitrogen Bead Separations*, 2007.
Jaklevic, "Automation of High-Throughput PCR Assays," Laboratory Robotics and Automation, 8(5):277-286, John Wiley & Sons Inc., USA.
Jaton et al., "Development of polymerase chain reaction assays for detection of Listeria monocytogenes in clinical cerebrospinal fluid samples," J. Clin. Microbiol., 1992, 30(8):1931-1936, American Society for Microbiology, Washington D.C., USA.
Jungkind et al., "Evaluation of Automated Cobas Amplicor PCR System for Detection of Several Infectious Agents and Its Impact on Laboratory Management," J. Clin. Microbiol., 1996, 34(11):2778-2783, American Society for Microbiology, Washington, D.C., USA.
Kalinina et al., "Nanoliter scale PCR with TagMan detection," Nucleic Acids Res., 1997, 25(10):1999-2004, Oxford University Press, Oxford, United Kingdom.
Kapperud et al., "Detection of Pathogenic Yersinia enterocolitica in Foods and Water by Immunomagnetic Separation, Nested Polymerase Chain Reactions, and Colorimetric Detection of Amplified DNA," Appl. Environ. Microbiol., 1993, 59(9):2938-2944, American Society for Microbiology, Washington, D.C., USA.
Kendrew et al., "Polymerase Chain Reaction," in The Encyclopedia of Molecular Biology, 1994, pp. 864-865, Blackwell Science Ltd., Cambridge, USA.
Khalil "Automation and Use of Robotics in Nucleic Acid Amplification Assays," in Nucleic Acid Amplification Technologies: Application to Disease Diagnosis, 1997, p. 151-164, Eaton Pub. Co., Natick, USA.
Kolk et al., "Development of Individual and Multiplex Assays for the Detection of HIV and HCV," 13th Annual Clinical Virology Symposium and Annual Meeting of the Pan American Society for Clinical Virology, M7, Apr. 27-30, 1997, Clearwater Beach, USA.
Kolmodin et al., "Basic Principles and Routine Practice," in PCR Cloning Protocols From Molecular Cloning to Genetic Engineering, 1997, pp. 3-5, Humana Press, Totowa, USA.
Kost, G. J., *Handbook of Clinical Automation, Robotics, and Optimization*; Chapters 1, 10, and 12-14; 1996 by John Wiley & Sons, Inc.; 189 pages total.
Kretz et al., "Cycle sequencing," PCR Methods and Applications, 1994, 3:S107-S112, Cold Spring Harbor Laboratory, Cold Spring Harbor Press, USA.
Krieg, "Quantification of RNA by Competitive RT PCR," in A Laboratory Guide to RNA, 1996, p. 210, Wiliey-Liss, New York City, USA.
Kwok et al., "Avoiding False Positive with PCR," Nature, 1989, 339:237-238, Nature Publishing Group, Basingstoke, USA.
Landry, "False-Positive Polymerase Chain Reaction Results in the Diagnosis of Herpes Simplex Encephalitis," J. Infect. Dis., 1995, 172(6):1641-1642, University of Chicago Press, Chicago, Usa.
Lay et al., "Real-time fluorescence genotyping of factor V Leiden during rapid-cycle PCR," Clin. Chem., 1997, 43(12):2262-2267, American Association for Clinical Chemistry, Washington D.C., USA.
Lee et al., "Direct Identification of *Vibrio vulmificus* in Clinical Specimens by Nested PCR," J. Clin. Microbial., 1998, 36 (10):2887-2892, American Society for Microbiology, Washington D.C., USA.
Lee et al., "Nucleic Acid Amplification Technologies: Application to Disease Diagnosis," BioTechniques Books, 1997, pp. 1-286, Eaton Publishing, Massachusetts, USA.
Leone et al., "Molecular beacon probes combined with amplification by NASBA enable homogeneous, real-time detection of RNA," Nucleic Acids Res., 1998, 26(9): 2150-2155, Oxford University Press, Oxford, United Kingdom.
Lisby, "Application of Nucleic Acid Amplification in Clinical Microbiology," in Methods in Molecular Biology: PCR in Bioanalysis, 1998, pp. 1-29, Humana Press, Totowa, USA.
Livak et al., "Oligonucleotides with Fluorescent Dyes at Opposite Ends Provide a Quenched Probe System Useful for Detecting PCR Product and Nucleic Acid Hybridization," PCR Methods and Applications, 1995, 4:357-362, Cold Spring Harbor Laboratory Press, Cold Spring Harbor, New York, USA.
Lo et al., "Quantitative Analysis of Fetal DNA in Maternal Plasma ad Serum: Implications for Noninvasive Prenatal Diagnosis," 1998, Am. J. Hum. Genet., 62:768-775, American Society of Human Genetics, Baltimore, USA.
Lo, "Setting Up a PCR Laboratory," in Methods in Molecular Medicine: Clinical Applications of PCR, 1998, pp. 12-17, Humana Press, Totowa, USA.
Longo, "Use of uracil DNA glycosylase to control carry-over contamination in polymerase chain reactions" Gene, 1990, 93: 125-128, Elsevier/North-Holland, Amsterdam.
Mabilat et al., "Routine Identification of Mycobacterium Tuberculosis Complex Isolates by Automated Hybridization," J. Clin. Microbiol., 1994, 32(11):2702-2705, American Society for Microbiology, Washington, D.C., USA.
Magnemotion; "MagneMover™ LITE,"; located at http://www.magnemotion.com/industrial-automation/magmoverlite.cfm; last visited on Jul. 20, 2013; 3 pages.
Mangiapan, "Sequence capture-PCR improves detection of mycobacterial DNA in clinical specimens" J Clin Microbiol., 1996, 34: 1209-1215, American Society for Microbiology, USA.
Martin et al., "PCR and Its Modifications for the Detection of Infectious Disease," Nucleic Acid Amplification Technologies: Application to Disease Diagnosis, 1997, p. 79-100, Eaton Pub. Co., Massachusetts, USA.

(56) References Cited

OTHER PUBLICATIONS

McCreedy et al., "Laboratory Design and Work Flow," Diagnostic Molecular Microbiology Principles and Applications, 1993, p. 149-159, Mayo Foundation, Rochester, USA.

Meng et al., "Turbo PCR—An Integrated Robotic System for Continuously Setting Up and Running Multiple PCR Reactions," DOE Human Genome Program Contractor-Grantee Workshop IV, Nov. 13-17, 1994, Santa Fe, New Mexico, 1 page.

Mercier et al., "Direct PCR from whole blood, without DNA extraction," Nucleic Acids Res., 1990, 18(19):5908, Oxford University Press, Oxford, United Kingdom.

Merel et al., "Completely Automated Extraction of DNA from Whole Blood," Clin. Chem., 1996, 42(8):1285-1286, American Association for Clinical Chemistry, USA.

Merel et al., "Perspectives on Molecular Diagnostics Automation," JALA, 2005, 10:342-350, Association for Laboratory Automation, Charlottesville, USA.

Meyers, "PCR Technology," Molecular Biology and Biotechnology: A Comprehensive Desk Reference, 1995, pp. 642-646, VCH Publishers Inc., New York City, USA.

Mischiati et al., "Use of an Automated Laboratory Workstation for Isloation of Genomic DNA Suitable for PCR and Allele-Specific Hybridization," BioTechniques, 1993, 15(1):146-151, Eaton Pub. Co., Natick, USA.

Mondada, Francesco et al.; "The e-Puck, a Robot Designed for Education in Engineering", *Proceedings of the 9th Conference on Autonomous Robot Systems and Competitions*, Castelo Branco, Portugal; May 7, 2009; vol. 1; Issue 1; pp. 59-65.

Mullis, "Eine Nachtfahrt und die Polymerase-Kettenreaktion," Spektrum der Wissenschaft, 1950, pp. 60-67, Germany.

Muramatsu et al., "Molecular Cell Biology Dictionary," 1997, Tokyo Kagaku Dojin Publisher, Tokyo, Japan, English Translation, 10 pages.

NACE, "Automation in Molecular Diagnostics: A Pleasant Surprise," Advance for Medical Laboratory Professionals, 2006, 14(11):64, Merion Publications, King of Prussia, PA, USA.

Nazarenko et al., "A closed tube format for amplification and detection of DNA based on energy transfer," Nucleic Acids Res., 1997, 25(12):2516-2521, Oxford University Press, Oxford, United Kingdom.

Neumaier et al., "Fundamentals of Quality Assessment of Molecular Amplification Methods in Clinical Diagnostics," Clin. Chem., 1998, 44(1):12-26, American Society for Clinical Chemistry, Washington D.C., USA.

Newton et al., "Instrumentation, Reagents and Consumables," PCR, 1996, 2nd ed., Chpt. 2, pp. 9-28, Bios Scientific, UK.

Nickerson et al., "Automated DNA Diagnostics Using an Elisa-based Oligonucleotide Ligation Assay," Proc. Natl. Acad. Sci. USA, 1990, 87:8923-8927, National Academy of Sciences, Washington, D.C., USA.

Niederhauser et al., "Direct Detection of *Listeria monocytogenes* Using Paramagnetic Bead DNA Extraction and Enzymatic DNA Amplificaiton,", Molecular and Cellular Probes, 1994, 8:223-228.

Noordhoek et al., "Reliability of Nucleic Acid Amplification for Detection of Mycobacterium Tuberculosis: an International Collaborative Quality Control Study Among 30 Laboratories," J. Clin. Microbiol., 1996, 34(10):2522-2524, American Society for Microbiology, Washington D.C., USA.

Obata et al., "Development of a Novel Method for Operating Magnetic Particles, Magtration Technology, and Its Use for Automating Nucleic Acid Purification," J. Biosci. Bioeng., 2001, 91(5):500-503, Elsevier Science, Amsterdam, Netherlands.

Oehlenschlager et al., "Detection of HIV-1 RNA by nucleic acid sequence-based amplification combined with fluorescence correlation spectroscopy," Biochemistry, 1996, 93:12811-12816, Proc. Natl. Acad. Sci. USA, Washington D.C., USA.

Olive, "Q-Beta Replicase Assays for the Clinical Detection of Infectious Agents," in Nucleic Acid Amplification Technologies: Application to Disease Diagnosis, 1997, p. 110, Eaton Pub. Co., Natick, USA.

Olsvik et al., "Magnetic Separation Techniques in Diagnostic Microbiology," Clin. Microbiol. Rev., 1994, 7(1):43-54, American Society for Microbiology, Washington, D.C., USA.

Oste, "Polymerase Chain Reaction," Product Application Focus, BioTechniques, 1988, 6(2):162-167, Informa Healthcare USA, Inc., UK.

Package Insert, "APTIMA® Assay for *Neisseria gonorrhoeae*," IN0148-01-REG, Rev. 1, Nov.2004, Gen-Probe Incorporated, San Diego, USA, 20 pages.

Package Insert, "APTIMA® HCV RNA Qualitative Assay," 500237 Rev. B, Jul. 2006, Gen-Probe Incorporated, San Diego, USA, 18 pages.

Package Insert, "Gen-Probe® Amplified Mycobacterium Tuberculosis Direct Test," IN0006 Rev. A, Feb. 24, 1994, Gen-Probe Incorporated, San Diego, USA, 14 pages.

Package Insert, "Gen-Probe® Amplified™ Chlamydia Trachomatis Assay," IN0012 Rev. A, Jan. 6, 1997, Gen-Probe Incorporated, San Diego, USA, 17 pages.

Package Insert, "Gen-Probe® Amplified™ Chlamydia Trachomatis Swab Specimen Preparation Kit," In0016 Rev. A, Jan. 6, 1997, Gen-Probe Incorporated, San Diego, USA, 3 pages.

Package Insert, "Gen-Probe® Amplified™ Chlamydia Trachomatis Urine Specimen Preparation Kit," IN0017 Rev. A, Nov. 11, 1996, Gen-Probe Incorporated, San Diego, USA, 3 pages.

Package Insert, "Gen-Probe® APTIMA® Combo 2 Assay," IN0037 Rev. A, Jun. 6, 2001, Gen-Probe Incorporated, San Diego, USA, 28 pages.

Package Insert, "Gen-Probe® APTIMA Combo 2® Assay," 501011 Rev. A, Jan. 2007, Gen-Probe Incorporated, San Diego, USA, 44 pages.

Package Insert, "Gen-Probe® APTIMA® Assay for *Chlamydia trachomatis*," IN0147-01, Rev. B, Apr. 2005, Gen-Probe Incorporated, San Diego, USA, 24 pages.

Package Insert, "Procleix® HIV-1/HCV Assay," IN0076-01-FDA, Rev. 3, Jun. 2004, Gen-Probe Incorporated, San Diego, USA, 28 pages.

Package Insert, "Procleix® HIV-1/HCV Assay," IN0076-02-FDA, Rev. 1, Jan. 2005, Gen-Probe Incorporated, San Diego, USA., 32 pages.

Package Insert, "Procleix® Ultrio™ Assay," IN0167EN, Rev. 1, Aug. 2004, Gen-Probe Incorporated, San Diego, USA, 44 pages.

Package Insert, "Procleix@ WNV Assay," IN0155, Rev. 1, Apr. 2004, Gen-Probe Incorporated, San Diego, USA, 15 pages.

Paillard et al., "Direct nucleic acid diagnostic tests for bacterial infectious diseases: *Streptococcal pharyngitis*, pulmonary tuberculosis, vaginitis, chlamydial and gonococcal infections," MLO, Jan. 2004, pp. 10-15, Medical Laboratory Observer, NP Communications, LLC, Monroe Township, USA.

Panaccio et al., "PCR based diagnosis in the presence of 8% (v/v) blood," Nucleic Acids Res., 1991, 19(5):1151, Oxford University Press, Oxford, United Kingdom.

Patel et al., "Death from Inappropriate Therapy for Lyme Disease," Clin. Infect. Dis., 2000, 31:1107-1109, the University of Chicago Press, Chicago, USA.

Patterson et al., "Random and continuous-access immunoassays with chemiluminescent detection by Access automated analyzer," Clin. Chem., 1994, 40(11):2042-2045, American Association for Clinical Chemistry, Washington D.C., USA.

Pauwels et al., "Automated techniques in biotechnology," Current Opinion in Biotechnology, 1995, 6:111-117, Current Biology Ltd., London, United Kingdom.

Pawlotsky, "Measuring Hepatitis C Viremia in Clinical Samples: Can We Trust the Assays?" J. Hepatol., 1997, 26(1):1-4, Viral Hepatitis Foundation Bangladesh, Dhaka, Bangladesh.

Persing, "Diagnostic molecular microbiology. Current challenges and future directions," Diagn. Microbiol. Infect. Dis., 1993, 16(2):159-163, Elsevier Biomedical, New York, USA.

Petrik et al., "Human Hepatic Glyceraldehyde-3-phosphate dehydrogenase Binds to the poly(U) tract of the 3' Non-Coding Region of Hepatitis C Virus Genomic RNA," J. General Virology, 1999, 80:3109-3113.

Request for Inter Partes Reexamination of U.S. Pat. No. 7,524,652, filed on Sep. 15, 2012, 134 pages.

(56) References Cited

OTHER PUBLICATIONS

Riggio et al., "Identification by PCR of Helicobacter pylori in subgingival plaque of adult periodontitis patients," J. Med. Microbiol., 1999, 48:317-322, The Pathological Society of Great Britain and Ireland.

Rosenblum et al., "New dye-labeled terminators for improved DNA sequencing patterns," Nucleic Acids Res., 1997, 25(22):4500-4504, Oxford University Press, UK.

Rudi et al., "Rapid, Universal Method to Isolate PCR-Ready DNA Using Magnetic Beads," BioTechniques, 1997, 22(3):506-511, Informa Healthcare USA, Inc., UK.

Rudi, et al., "Detection of Toxin-Producing Cyanobacteria by Use of Paramagnetic Beads for Cell Concentration and DNA Purification," 1998, Appl. Environ. Microbiol., 64(1):34-37, Am. Society of Microbiol., USA.

Schepetiuk et al., "Detection of Chlamydia trachomatis in Urine Samples by Nucleic Acid Tests: Comparison with Culture and Enzyme Immunoassay of Genital Swab Specimens," J. Clin Micorbiol., Dec. 1997, 35(12):3355-3357.

Skeggs, "An automatic method for colorimetric analysis," Am. J. Clin. Pathol., 1957, 28:311-322, American Society of Clinical Pathologists, Chicago, USA.

Smith et al., "Abbott AxSYM random and continuous access immunoassay system for improved workflow in the clinical laboratory," Clin. Chem., 1993, 39(10):2063-2069, American Association for Clinical Chemistry, Washington D. C., USA.

Smith et al., "Detection of Mycobacterium tuberculosis Directly from Sputum by Using a Prototype Automated Q-Beta Replicase Assay," J. Clin. Microbiol., 1997, 35(6):1477-1483, American Society for Microbiology, Washington, D.C., USA.

Smith et al., "Performance of an Automated Q-Beta Replicase Amplification Assay for Mycobacterium tuberculosis in a Clinical Trial," J. Clin. Microbiol., 1997, 35(6):1484-1491, Am. Society for Microbiology, USA.

Stanley et al., "A Survey of More Than 90 Commercially Available Luminometers and Imaging Devices for Low-Light Measurements of Chemiluminescence and Bioluminescence, Including Instruments for Manual, Automatic and Specialized Operation, for HPLC, LC, GLC and Microtitre Plates. Part 2: Photographs," J. Biolumin. Chemilumin., 1992, 7:157-169, John Wiley & Sons, Ltd., Chichester, Sussex, England.

Stanley, "Commercially Available Luminometers and Imaging Devices for Low-Light Level Measurements and Kits and Reagents Utilizing Bioluminescence or Chemiluminescence: Survey Update 3," J. Biolumin. Chemilumin., 1994, 9:123-125, John Wiley & Sons, Ltd., UK.

Stone et al., "Detection of rRNA from four respiratory pathogens using an automated Qβ replicase assay," Mol. Cell. Probes, 1996, 10:359-370, Academic Press Limited, San Diego, California, USA.

Suryanarayana et al., "Plasma SIV RNA Viral Load Determination by Real-Time Quantification of Product Generation in Reverse Transcriptase-Polymerase Chain Reaction," AIDS Res. Hum. Retroviruses, 1998, 14(2):183-189, Mary Ann Liebert, Inc., USA.

Sutton et al., "Hands Free Polymerase Chain Reaction," International Symposium on Laboratory Automation and Robotics, Oct. 17-20, 1993, p. 326-336, Boston, USA.

Sutton et al., "PCR Has Outgrown Appropriate Automated Instrumentation But Help is on the Way," Today's Chemist at Work, 1995, p. 42-48, American Chemical Society, Washington, D.C., USA.

Taos Inc. "TCS230 Programmable Color to Light-to-Frequency Converter," www.http?pdfl.alldatasheet.com/datasheet-pdf/view/96470/ETC/TCS230.html; Jan. 31, 2003, pp. 1-8.

Techne PHC-3 Thermal Cycler—TECHNI, Jun. 2009, Pegasus Scientific Inc., USA.

Tjian, "Purification and comparative properties of the delta and sigma subunits of RNA polymerase from Bacillus subtilis" Eur. J. Biochem., 1977, 74:149, Blackwell Science Ltd. on behalf of the Federation of European Biochemical Societies, UK.

Tyagi et al., "Extremely sensitive, background-free gene detection using binary proves and QB Replicase," Biochemistry, 1996, 93:5395-5400, Proc. Natl. Acad. Sci. USA, Washington D.C., USA.

Tyagi et al., "Molecular Beacons: Probes that Fluoresce upon Hybridization," Nature Biotechnology, 1996, 14:303-308, Nature Publishing Company, New York, USA.

Uckun et al., "Clinical Significance of MLL-AF4 Fusion Transcript Expression in the Absence of a Cytogenetically Detectable t(4;11)(q21;q23) Chromosomal Translocation," Blood, 1998, 92(3):810-821, American Society of Hematology, Washington D.C., USA.

Van Gemen, B. at al.; "The One-tube Quantitative HIV-1 RNA NASBA: Precision, and Application,"; 1995; PCR Methods Appl.; vol. 4; pp. 177-184.

Victor et al., "Laboratory Experience and Guidelines for Avoiding False Positive Polymerase Chain Reaction Results," Eur. J. Clin. Chem. Clin. Biochem., 1993, 31(8):531-535, Walter de Gruyter & Co., Berlin, Germany.

Voss et al., "Direct genomic fluorescent on-line sequencing and analysis using in vitro amplification of DNA," Nucl. Acids Res., 1989, 17(7):2517-2527, IRL Press, USA.

Walker et al., "Detection of Mycobacterium tuberculosis DNA with thermophilic strand displacement amplification and fluorescence polarization," Clin. Chem., 1996, 42(10):1604-1608, American Association for Clinical Chemistry, Washington D.C., USA.

Walker et al., "Strand displacement amplification (SDA) and transient-state fluorescence polarization detection of Mycobacterium tuberculosis DNA," Clin. Chem., 1996, 42(1):9-13, American Association for Clinical Chemistry, Washington D.C., USA.

Walter et al., "Fluorescence correlation analysis of probe diffusion simplifies quantitative pathogen detection by PCR," Proc. Natl. Acad. Sci. USA, 1996, 93:12805-12810, National Academy of Sciences, Washington D.C., USA.

Whelan et al., "The Role of Nucleic Acid Amplification and Detection in the Clinical Microbiology Laboratory," Annu. Rev. Microbiol., 1996, 50:349-373, Annual Reviews, Palo Alto, USA.

Wilke et al., "Automation of Polymerase Chain Reaction Tests Reduction of Human Errors Leading to Contamination," Diagn. Microbiol. Infect. Dis., 1995, 21:181-185, Elsevier Sciences, New York City, USA.

Wilke et al., "Automation of Polymerase Chain Reaction Tests to Achieve Acceptable Contamination Rates," Clin. Chem., 1995, 41(4):622-623, American Association for Clinical Chemistry, Washington, D.C., USA.

Wittwer et al., "The LightCycler: a microvolume multisample fluorimeter with rapid temperature control," BioTechniques, 1997, 22:176-181, Informa Healthcare USA, Inc., London, United Kingdom.

Yourno et al., "A method for nested PCR with single closed reaction tubes," PCR Methods Appl., 1992, 2(1):60-65, Cold Spring Harbor Laboratory Press, Cold Spring Harbor, New York, USA.

Genprobe; "Test Procedure Guide. Amplified Mycobacterium Tuberculosis Direct (MTD) Test,"; 2000, 1 page.

International Search Report and Written Opinion mailed on Nov. 6, 2013 for PCT Patent Application No. PCT/US2012/063918, 22 pages.

ABI Product Catalogue, 1993-1994, "DNA Sequencing Reagents," p. 146, Applied Biosystems, USA.

Anonymous, "GeneAmp optical reaction plate," Nature, 1998, 391(8):210, Nature Publishing Group, USA.

Asper et al., "Laboratory Mechanization and Automation," in Laboratory Organization Automation, 1991, pp. 271-275, Walter deGruyter, USA.

Bieche et al., "Novel Approach to Quantitative Polymerase Chain Reaction Using Real-Time Detection: Application to the Detection of Gene Amplification in Breast Cancer," Int. J. Cancer, 1998, 78:661-666, Wiley-Liss, Inc., USA.

Billyard, et al., "Early detection of HIV-1 RNA from sero-conversion panels using Gen-Probe's transcription-mediated amplification," The San Diego Conference Nucleic Acid Technology: The Cutting Edge of Discovery, Nov. 6-8, 1997, Clin. Chem., 1997, 43(11):2221, Am. Assoc. for Clin. Chem., USA.

(56) References Cited

OTHER PUBLICATIONS

Burg et al., "Real-time fluorescence detection of RNA amplified by Q beta replicase," Anal. Biochem., 1995, 230(2):263-272, Academic Press, Orlando, Florida, USA.
Chemistry Guide, "ABI PRISM DNA Sequencing," 1995, pp. 1-3-1-6, The Perkin-Elmer Corporation, USA.
Civitello et al., "A simple protocol for the automation of DNA cycle sequencing reactions and polymerase chain reactions," DNA Sequence—J. DNA Sequencing and Mapping, 1992, 3:17-23, Harwood Academic Publishers GmbH, UK.
Dangler, ed., Nucleic Acid Analysis: Principles and BioApplications, 1996, pp. 1-3, 19, 68-75, 106-109, 116, 117, 144, 145, 157, 162 & 163, Wiley-Liss, Inc., USA.
Educational Guide, "New Directions in Molecular Diagnostic Testing," pp. 1-12, Rev. A, 2000, Gen-Probe Incorporated, San Diego, USA.
Felder, "Automation of Preanalytical Processing and Mobile Robotics," in Handbook of Clinical Automation, Robotics, and Optimization, 1996, pp. 252-256, John Wiley & Sons, Inc., USA.
Hawkins et al., "Thermal Cycle DNA Sequence Setup Using a Modified Lab Workstation," LRA, 1995, 7:117-122, VCH Publishers, New York City, USA.
Higuchi et al., "Kinetic PCR Analysis: Real-time Monitoring of DNA Amplification Reactions," Bio/Technology, 1993, 11(9):1026-30, Nature Publishing Group, New York, USA.
Hill et al., "The Polymerase Chain Reaction in Molecular and Micro-biology," Biotechnol. Genet. Eng. Rev., 1992, 10:343-377, Taylor & Francis, UK.
Holmberg et al., "Automatic Preparation of DNA Templates for Sequencing on the ABI Catalyst Robotic Workstation," Automated DNA Sequencing and Analysis, 1994, Academic Press Inc., San Diego, USA.
Hunkapiller, "Advances in DNA sequencing technology," Curr. Opin. Genet. Dev., 1991, 1:88-92, Elsevier, UK.
Jakobsen et al., "Direct mRNA Isolation Using Magnetic Oligo (dT) Beads: A Protocol for All Types of Cell Cultures, Animal and Plant Tissues," in Advances in Biomagnetic Separation, 1994, pp. 61-71, Eaton Publishing, USA.
Kasper, "Automated Instrumentation (Generic)," in Clinical Laboratory Instrumentation and Automation: Principles, Applications, and Selection, 1994, pp. 184-205, W.B. Saunders Company, USA.
Kaufman et al., "Direct Sequencing by PCR," in Handbook of Molecular and Cellular Methods in Biology and Medicine, 1995, pp. 233-235, CRC Press, USA.
Krieg, ed., "Quantitation of RNA Transcripts Using RT-PCR," in A Laboratory Guide to RNA: Isolation, Analysis, and Synthesis, 1996, pp. 176-190, John Wiley & Sons, Inc., USA.
Little et al., "Recent Advances in Robotic Automation of Microplate Assays," Lab. Info. Mgmt., 1994, 26:89-99, Elsevier Science, Amsterdam, Netherlands.
Lundeberg et al., "Solid-Phase Technology: Magnetic Beads to Improve Nucleic Acid Detection and Analysis," Biotechnol. Annu. Rev., 1995, 1:373-401, Elsevier Science, Amsterdam, Netherlands.
Mahan et al., "An Automated System for Infectious Disease Diagnosis with Q-Beta Replicase Amplification," in New Horizons in Gene Amplification Technologies: Proceedings of a CHI Meeting, 1994, Cambridge, USA, 25 pages.
McDonough et al., High Throughput Assay for the Simultaneous or Separate Detection of Human Immunodeficiency Virus (HIV) and Hepatitis Type C Virus (HCV), Infusionsther. Transfusionsmed, 1998, 25:164-169, Karger GmbH, Germany.
Mertes et al., Automatische genetische Analytik, 1997, forward and pp. 68, 69, 73 & 74, Wiley-VCH, Germany; German Language Reference.
Mizutani et al., "Magnetic Separation in Molecular Studies of Human Leukemia," in Advances in Biomagnetic Seperation, 1994, p. 127-133, Eaton Publishing, USA.
Olsvik et al., "Magnetic Separation in Laboratory Diagnosis of Infectious Diseases," in Advances in Biomagnetic Separation, 1994, pp. 149-158, Eaton Publishing, USA.
Olympus Corporation, "Olympus News Release: Automated Chemistry Analyser AU1000," 1997, http://www.olympusglobal.com/en/news/1997a/nr970421au1000e.jsp, downloaded Jun. 17, 2013, USA, 3 pages.
Overbergh et al., "Quantification of Murine Cytokine mRNAs Using Real Time Quantitative Reverse Transcriptase PCR," Cytokine, 1999, 11(4):305-312, Academic Press, USA.
Petrik et al., "High throughput PCR detection of HCV based on semiautomated multisample RNA capture," J. Virol. Methods, 1997, 64:147-159, Elsevier/NorthHolland Biomedical Press, Amsterdam, Netherlands.
Piatek et al., "Molecular beacon sequence analysis for detecting drug resistance in Mycobacterium tuberculosis," Nature Biotechnology, 1998, 16:359-363, Nature America Publishing, New York, USA.
Shah et al., "Novel, Ultrasensitive, Q-Beta Replicase-Amplified Hybridization Assay for Detection of Chlamydia trachomatis," J. Clin. Microbiol., 1994, 32(11):2718-2724, American Society for Microbiology, USA.
Slatko, "Thermal Cycle Dideoxy DNA Sequencing," in Protocols for Gene Analysis (Methods in Molecular Biology), 1994, vol. 31, pp. 35-45, Humana Press Inc., USA.
Sloan et al., "Screening Yeast Artificial Chromosome Libraries with Robot-Aided Automation," GATA, 1993, 10(6):128-143, Elsevier Science Publishing Co., Inc., USA.
Truchaud et al., "Liquid-Phase Reactions Started by Rehydrating Lyophilized Reagents in a Centrifugal Analyzer," Clin. Chem., 1985, 31(9):1506-1508, Am. Assoc. For Clin. Chem., USA.
Tyagi et al., "Multicolor molecular beacons for allele discrimination," Nat. Biotechnol., 1998, 16:49-53, Nature Publishing Group, USA.
Vonderschmitt, ed., "Robots in the Clinical Laboratory," in Laboratory Automation Organization, 1991, pp. 576-577, Walter deGruyter, USA.
Ward, ed., "Improving Laboratory Efficiency Through Workflow Analysis", in Clinical Laboratory Instrumentation and Automation: Principles, Applications, and Selection, 1994, pp. 453 & 457, W.B. Saunders Company, USA.
Webster's New World Dictionary, Third college Edition, 1988: Definition of Incubate, Incubator.
Yohda et al., "Development of a Novel Laboratory Automation System for Molecular Biology," Kaguku-Koguku Symposium, 1998, p. 17-20.
First Chinese Office Action mailed on May 27, 2015 for CN Patent Application No. 201280066152.0, with English Translation, 20 pages.

* cited by examiner

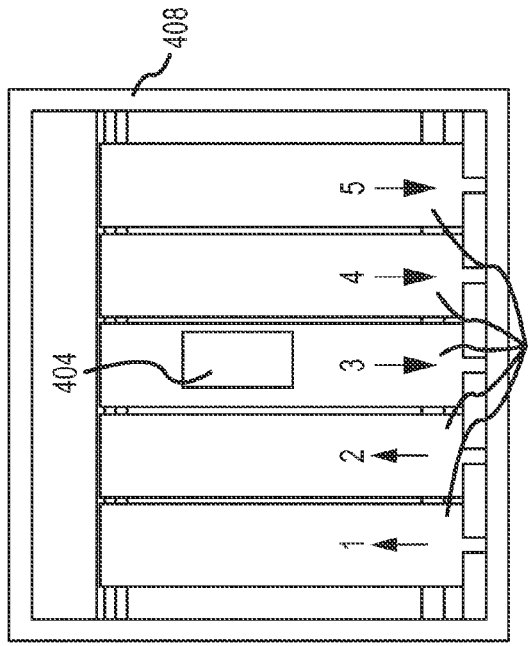
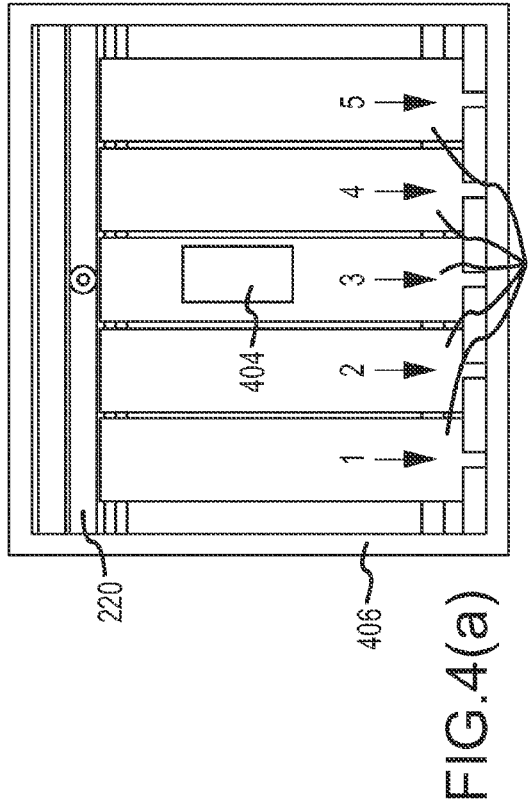
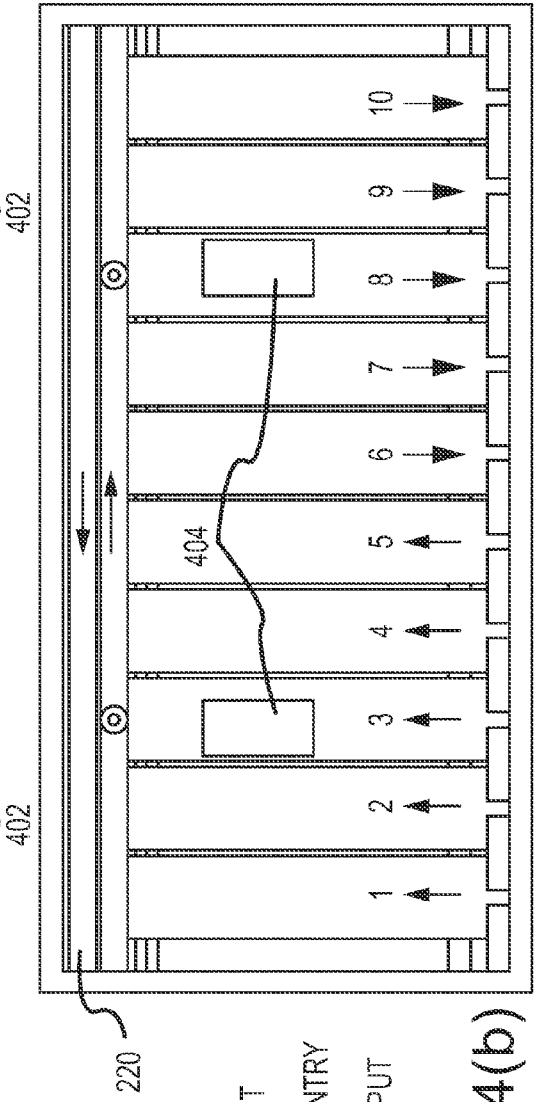
FIG.4(a)
FIG.4(b)

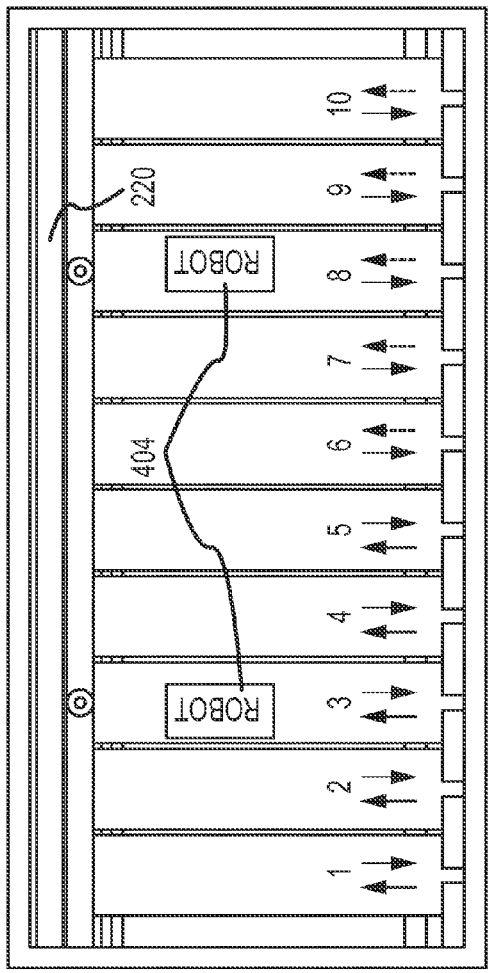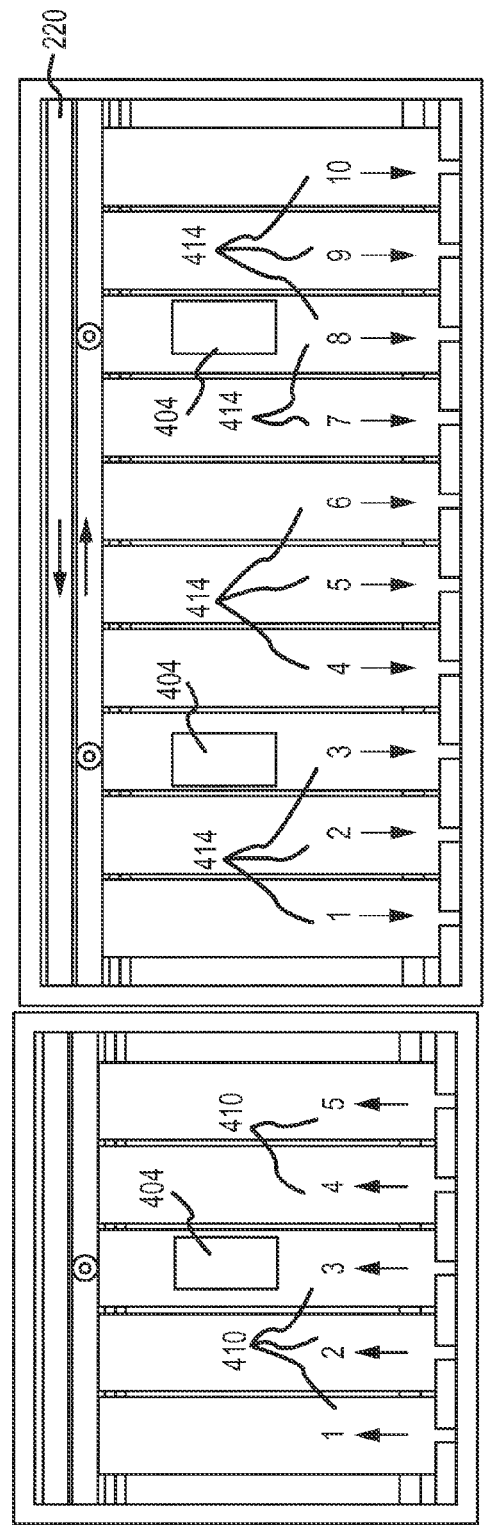
FIG.4(c)
FIG.4(d)

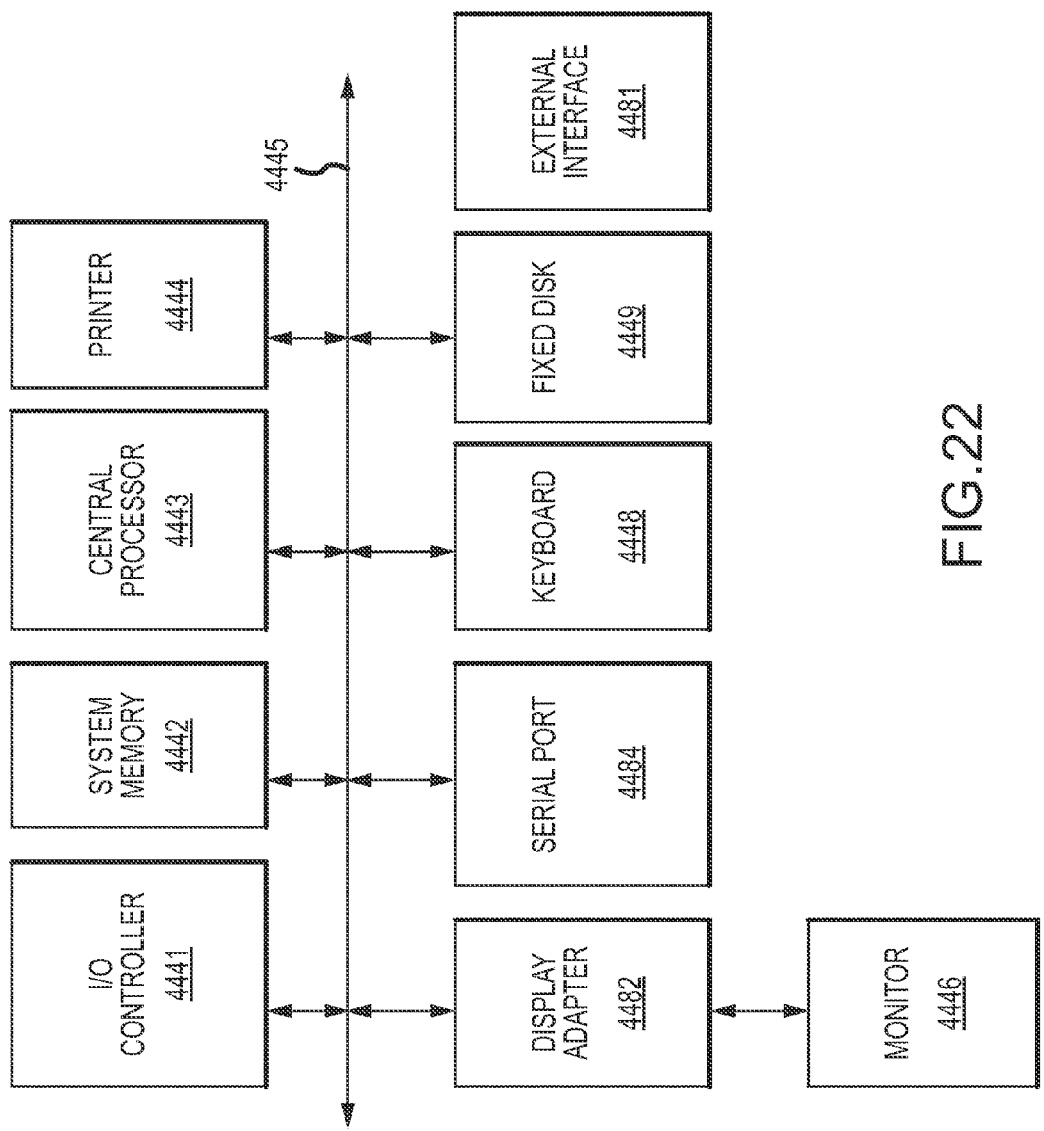

ROBOTIC ARM

CROSS-REFERENCES TO RELATED APPLICATIONS

This application claims priority to U.S. Provisional Patent Application No. 61/556,667, filed Nov. 7, 2011 and entitled "Analytical System and Method for Processing Samples." This application also claims priority to U.S. Provisional Patent Application No. 61/616,994, filed Mar. 28, 2012 and entitled "Analytical System and Method for Processing Samples." This application also claims priority to U.S. Provisional Patent Application No. 61/680,066, filed Aug. 6, 2012 and entitled "Analytical System and Method for Processing Samples." All of these applications are herein incorporated by reference in their entirety for all purposes.

BACKGROUND

Conventional medical laboratory systems contain many segments for processing patient samples, some of which are automated and some of which require manual operation. Laboratory systems today have become more efficient due to those segments which have become automated. However, there are still several components of medical laboratory systems that can be automated in order to reduce the time it takes for an analysis of a sample, reduce the need for manual operation of the system, and reduce the space required by machinery.

Generally, the laboratory process can be organized into four phases: association, pre-analytical, analytical, and post-analytical. These four phases typically occur within any laboratory process. However, some conventional labs may have a process that uses standalone units throughout the lab while others may connect some of the units with a conveyance system to move the sample from unit to unit. These two styles have some common and some different processing needs. Additionally, some conventional labs may consistently process the same types of sample tubes (e.g., as in those from a kit) while others may have a wide range of tube types that they must accommodate. Furthermore, many labs may have a preference for a particular manufacturer of an analyzer while others may use all of the analyzers from one manufacturer.

Thus, there is a need for a more efficient system and method for processing patient samples that can accommodate both a process using standalone units and units connected with a conveyance system, a variety of sample container types, and analyzers from any manufacturer.

Sample volume and sample level detection devices are known. Conventional sample volume or sample level detection devices are able to detect the total level of a liquid in a sample container either by (i) an image analysis approach of 2-dimensional images acquired by a camera system, or (ii) an absorption/transmission measurement of different wavelengths in a focused light beam. However, these devices are typically stand-alone devices that are manually operated by the laboratory system.

Robotic arms are also known. Conventional robotic arm technology for transporting objects from one position to another may utilize an XYZ-robot employing a gripper unit to grip and transport sample containers or centrifuge buckets. However, the current robotic arm technology is generally limited to gripping either the sample containers or centrifuge bucket, but not both. Additionally, the current technology cannot perform any additional functions besides the gripping function.

Embodiments of the invention address these and other problems, individually and collectively.

BRIEF SUMMARY

Embodiments of the technology relate to systems and methods for efficiently processing patient samples.

One embodiment is directed to a movable assembly for preparing a specimen for laboratory analysis. A robotic arm of the assembly has a gripper unit capable of gripping a sample container. The robotic arm is capable of three-dimensional movement. A first image acquisition device of the movable assembly is configured to acquire an image of the sample container. The image is analyzed, by a processor, to determine at least one of identifying information associated with the sample container and a liquid level of the sample in the sample container.

Another embodiment of the invention is directed to a method comprising transporting a sample container with a robotic arm having a gripper unit from a first location to a second location, wherein an image acquisition device is physically coupled to the robotic arm. The method also comprises acquiring an image of the sample container using the image acquisition device during transporting and analyzing the image of the sample container.

Another embodiment is directed to a method of transporting a sample container for analysis by a laboratory automation system. A sample container containing a sample is transported from an input area to a distribution area by a gripper comprising a means for inspecting a tube. Data is obtained during the transporting of the sample container. An image is captured of the sample container. The sample container may be identified based on at least one physical characteristic of the sample container via analysis of the image of the sample container. A liquid level of the sample in the sample container is determined. A weight of the sample container is calculated based on the sample container identification and the liquid level. A scheduling system determines a time when the sample container containing the sample will be processed. The tube is transported from the distribution area to a subsequent processing module by the gripper.

Another embodiment of the invention is directed to a system comprising an assembly comprising (a) a robotic arm having a gripper unit configured to gripping a sample container, wherein the robotic arm is configured to move in three dimensions, (b) an image acquisition device physically coupled to the robotic arm and configured to acquire an image of the sample container, and (c) an image analysis device in communication with the image acquisition device. The image analysis device is configured to analyze the image of the sample container to determine at least one of identifying information associated with the sample container and a liquid level of the sample in the sample container. The system further comprises a distribution area, wherein the sample container is configured to reside in the distribution area. The system further comprises a subassembly, coupled to the distribution area.

These and other embodiments of the technology are described in further detail below.

BRIEF DESCRIPTION OF THE DRAWINGS

A further understanding of the nature and advantages of the different embodiments may be realized by reference to the following drawings.

FIGS. 4(a)-(e) depict block diagrams of configurations of components associated with output/sorter modules.

FIG. 22 depicts a block diagram of an exemplary computer apparatus.

DETAILED DESCRIPTION

Figure 1:
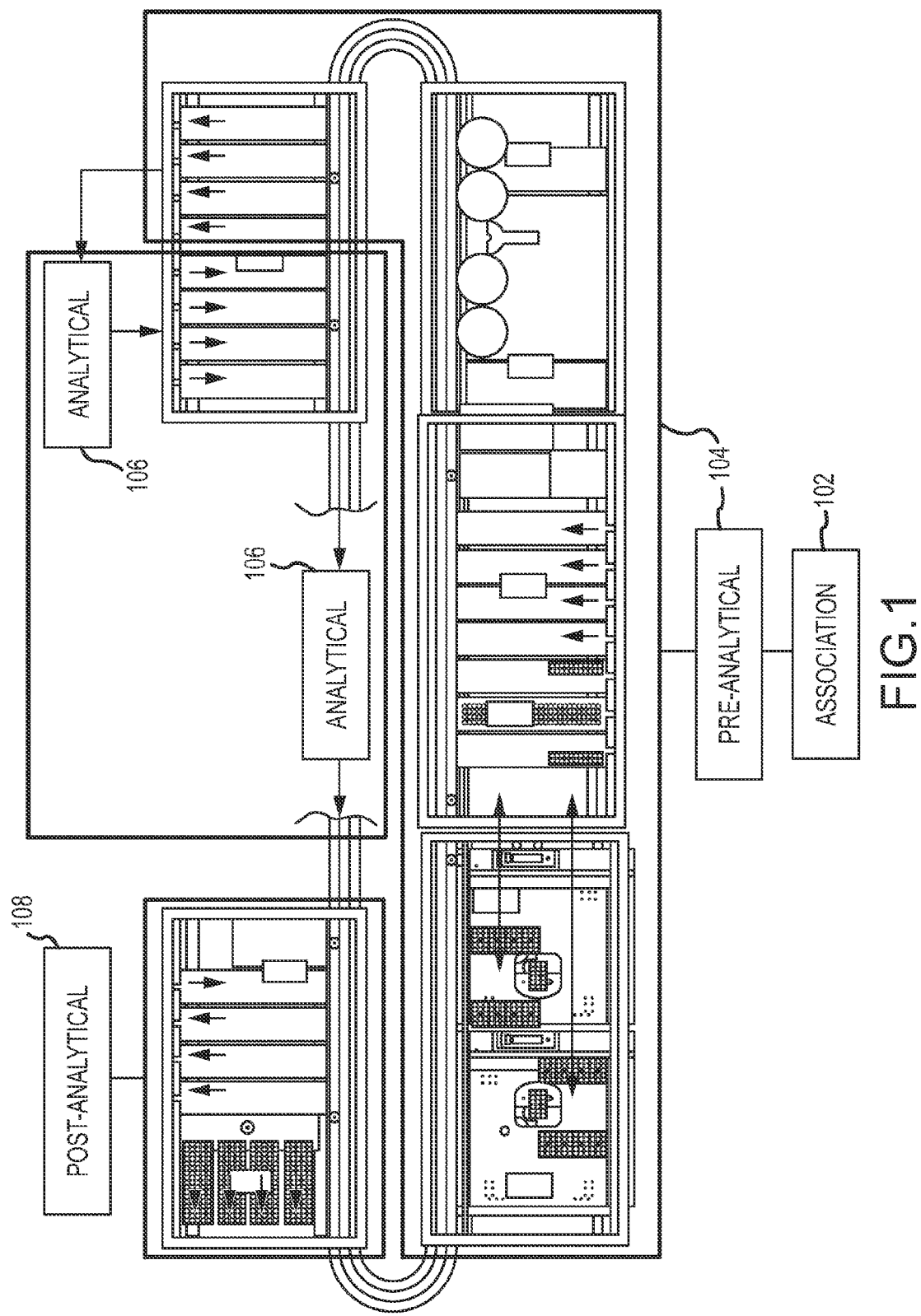
FIG. 1 depicts a block diagram of components associated with phases of a laboratory automation system.

Embodiments of the present technology relate to a laboratory system and method for processing patient samples. These embodiments, as will be described in more detail below, are advantageous because they provide, among other advantages, greater speed, accuracy, efficiency, and prevention of contamination. As discussed above, many conventional laboratory systems may have a process that uses standalone units throughout the lab, requiring that the samples be manually transported between each standalone unit, while others may connect some of the units with a conveyance system to move the samples from unit to unit. Additionally, as discussed above, sample tube sizes and equipment from different manufacturers may be constraints in conventional laboratory systems. Such conventional technology is slow and inaccurate. Embodiments of the present technology provide for a modular laboratory system which is capable of accommodating different laboratory units and transport systems, sample tube sizes, and manufacturers by using more universal components and by grouping functions required by most laboratory systems into five basic functional units: (1) manager, (2) centrifuge, (3), aliquotter, (4) output/sorter, and (5) storage units. These five basic functional units will be described in more detail below.

In embodiments of the invention, the laboratory system operates a controlled process using a central controller or scheduler. By keeping the samples under the control of an intelligent scheduler, the system provides efficient usage of every instrument. The system can maintain a consistent minimal turnaround time and maximizes the throughput of the entire system by maintaining control of the process and only delivering samples to instruments when those instruments are ready and available.

In embodiments of the invention, a "sample container" may have any suitable shape or form. In some embodiments, the sample container may be in the form of a sample tube, which may have an aspect ratio of greater than about 3:1. Such sample containers may be made or any suitable material including plastic, glass, etc. They may further include a sample tube body with a closed end and an open end, as well as a cap that is structured to cover and attach to the open end of the sample tube body.

In embodiments of the invention, a "sample container holder" may be in any suitable shape or form, and may comprise any suitable material. In some cases, the sample tube holder may be in the form of a sample tube rack. Sample container holders may include an array of recesses that can receive sample containers (e.g., sample tubes). They may also comprise any suitable material including plastic.

Embodiments of the invention further utilize one or more robotic gripper units mounted on robotic arms. Each robotic arm unit has a robotic gripper for gripping sample tubes and may be equipped with one or more means for detecting information about sample tubes. The means for detecting information about a sample tube may include a first image acquisition device, such as a camera, for identifying a sample tube among a plurality of sample tubes in a rack. The identified sample tube is gripped by the gripper. The means for detecting information about sample tubes may further include a second image acquisition device to obtain an image of the gripped sample tube. The level of liquid in the sample tube may be determined from the image obtained by the second image acquisition device. The second image acquisition device may comprise a receiver that receives transmissions from an emitter. In comparison with prior art systems, which have a camera mounted on a track and thus require all sample tubes to be on the track before the tubes can be identified, the laboratory system described herein can identify a sample tube before it is placed on a conveyer track. As a result, samples that do not need to be transported on the conveyer are not placed on the conveyer merely for the purpose of sample tube identification. Further, urgent samples can have a prioritized placement on the conveyer track.

Use of a plurality of robotic gripper units in the laboratory system also increases sample processing efficiency. A first gripper, such as an input module gripper, identifies a sample tube and makes data measurements as described above. After the first gripper delivers the sample tube to a distribution area, a second gripper, such as a distribution area gripper, delivers a sample tube to a subsequent module such as a centrifuge module or conveyor. The use of multiple grippers allows an increase in processing efficiency over prior art systems.

I. Overall System

A. Phases of Laboratory System

FIG. 1 depicts one embodiment of a medical laboratory system for processing patient samples. The laboratory system includes components associated with the association phase 102, the pre-analytical phase 104, the analytical phase 106, and the post-analytical phase 108.

1. Association Phase

The association phase 102 is the first phase in the laboratory process. During this phase, the patient information, the requested tests for the patient sample and a unique laboratory identifier (e.g., a barcode) are associated with one another. While the association phase 102 could be automated, in some embodiments, the association phase is handled manually. For example, in some embodiments, a laboratory technician (hereinafter referred to as a "user") can assign a priority to the samples. The samples are loaded into racks or directly onto the system at specific entry points. Although grouping samples into a few basic priority levels (e.g., urgent or high priority, medium priority, low priority, etc.) may be desirable to provide a more consistent turnaround time, it is not necessary. Processing patient samples can be based on any priority defined by the user. However, if a priority is not specified, a priority can be assigned based on factors such as minimizing turnaround time, maximizing throughput, the availability of processes, etc.

2. Pre-Analytical Phase

The pre-analytical phase 104 includes preparing patient samples for analysis. During the pre-analytical phase 104, the patient and test information is deciphered, the process for analysis is planned, quality checks are performed, the sample may be separated into its constituent components (e.g., centrifuged), the sample may be divided for parallel analytical processes, and/or the sample can be delivered to one or more analyzers and/or racks. The pre-analytical phase 104 manages the flow of samples to different instruments and different analyzers within the lab system. This process management permits the system to operate efficiently and with minimal instruments. Additionally, the pre-analytical phase 104 ensures that a backup of patient samples at different points within the lab system does not occur along the process, or if a backup does occur, the pre-analytical phase 104 ensures that the backup can be cleared quickly and without significant impact on the remainder of the system.

Embodiments of the system can identify the patient samples as quickly as possible and determine the best scheduling of each sample to provide a consistent minimal turnaround time and maximum throughput of the analytical processes. The steps and organization of those steps in the process are designed to avoid backups of patient samples. Modules of the lab system can operate at a throughput speed that ensures processing of samples at the maximum throughput of the upstream processes. However, in some embodiments, at the aliquotter unit, the throughput may be managed by the introduction of samples upstream and by small queues at each aliquotting station.

Figure 2:
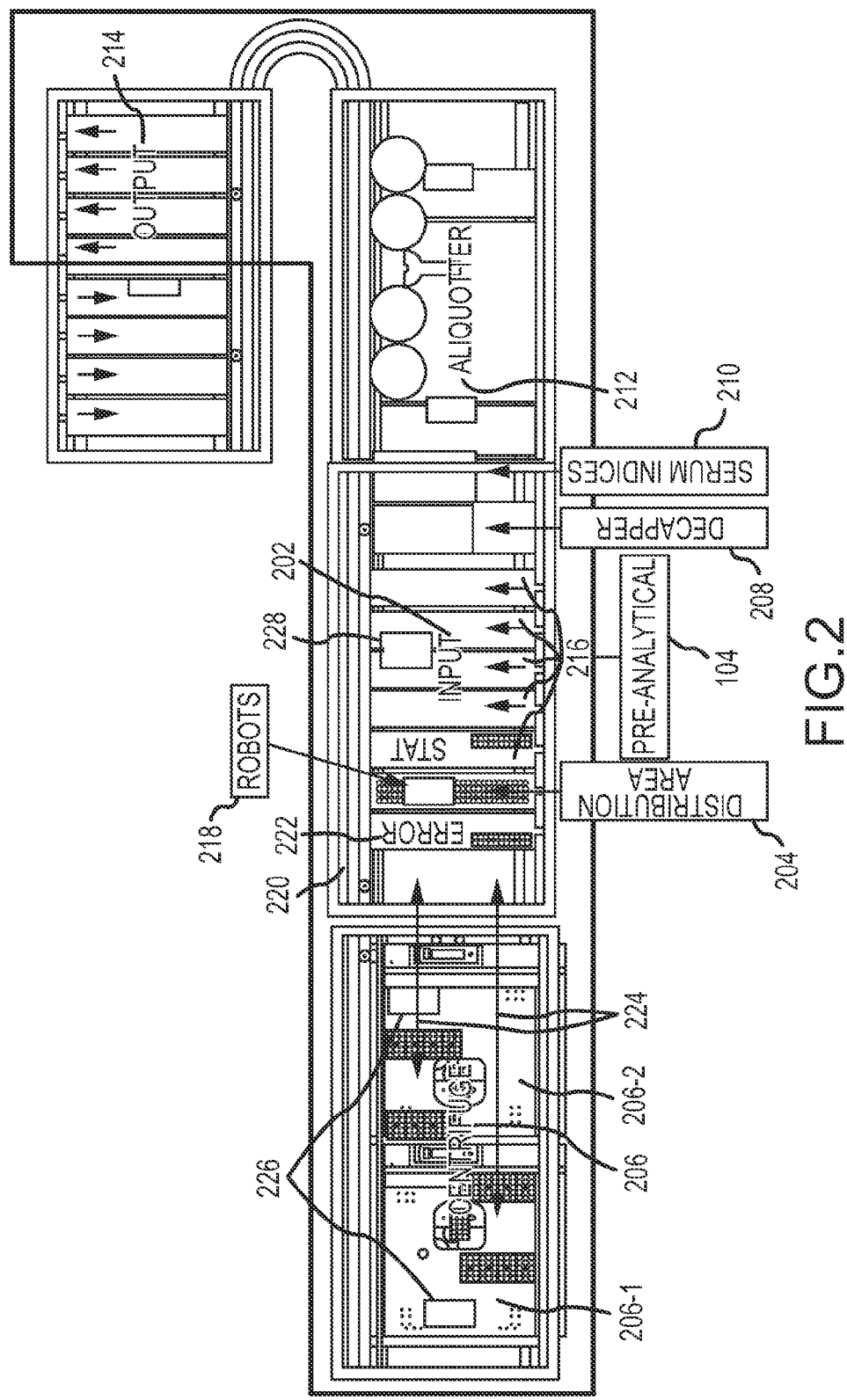
FIG. 2 depicts a block diagram of components associated with a pre-analytical phase of a laboratory automation system.

FIG. 2 is a more detailed depiction of the components associated with the pre-analytical phase 104. The components associated with the pre-analytical phase 104 include seven modules: input module 202, distribution area 204, centrifuge 206, decapper 208, serum indices measurement device 210, aliquotter 212, and output/sorter 214.

(a) Input Module

The input module 202 shown in FIG. 2 can accommodate a variety of tubes, racks, prioritizations, etc. and is capable of receiving a specimen. Racks of tubes and/or individual tubes can be loaded onto one of several lanes 216, which may be manually operated drawers and/or automated devices. In FIG. 2, five lanes 216 are depicted. However, the lab system can have any number of lanes 216. The lanes 216 are assigned priorities in accordance with those assigned by the user. In some embodiments, the highest priority lane (short turnaround time or "STAT") may have a fixed position for accepting a group of individual tubes from the user. Once tubes are loaded in the STAT lane, they become the next tubes processed. Other lanes can be assigned different priority levels in any manner. For example, when the drawers are manually operated, assigning one priority to at least two of the drawers and another priority to at least two other drawers may allow the system to operate continuously on one drawer while the other drawer of the same priority is available to the user.

In some embodiments, while the input module 202 is processing a drawer of samples, the user may be informed that the drawer should not be opened by using an indication such as a light on the drawer or a lock on the drawer. This may help maintain the process integrity and maximize throughput. When processing is complete on the first drawer, the drawer may be identified to the user as available, and the system may automatically begin processing another drawer. Additionally, the samples can be transferred to and from the drawers 216 of the input module 202 using an input module gripper 228.

(b) Distribution Area Module

From the lanes 216 within the input module 202 of FIG. 2, one of at least two or more distribution area grippers 218 (discussed in more detail below) may select the highest priority tube and transport it to a fixed matrix called the distribution area 204. The distribution area 204 is capable of distributing a specimen to a desired component (e.g., a subsystem) of the laboratory automation system. During the transfer to this module by the input module gripper 228, the levels of the sample's constituent components are measured and photographs of the sample tube are taken. These photographs can be analyzed to determine the tube's manufacturer, diameter, height, cap color, etc. From this information, the volumes of the sample's components can be calculated, and an estimate of the total tube weight can be made. This weight can be later used to aid in balancing the centrifuge buckets in the centrifuge module 206, as will be discussed in more detail below.

To protect the distribution area 204 from filling with low priority tubes, a limit can be set on the number of tubes loaded into this area from the low priority input lanes. Moreover, the distribution area 204 may have a reserved area to ensure STAT samples have continuous access to the distribution area 204 from the STAT drawer in the input module 202.

The distribution area 204 can be the holding area which permits the system to access test information associated with the sample tube in the association phase 102 and plan the analysis process for the sample. This enables the system to schedule a sample tube's process with respect to the other sample tubes currently on the system. Scheduling enables the efficient processing of samples based upon priority without overloading any step in the overall system, permitting the optimization of turnaround time and throughput. Furthermore, the sample's schedule can be updated throughout the process as the system's activity or availability changes, providing real time active control of the sample.

Once the schedule is planned by the distribution area module 204, one of the at least two or more distribution area robotic grippers 218 then selects the sample tube that is the next tube to be transferred to the next module based on the priority of the tubes within the distribution area 204. The selected sample tube is transported from the distribution area 204 to the conveyance system 220, to the centrifuge module 206, or to an error area 222 based on the analysis performed by the distribution area module 204.

If the sample tube is being moved to the centrifuge module 206, the tube can be placed into the appropriate centrifuge adapter based upon the earlier weight estimation to ensure proper balance of the centrifuge rotor. The centrifuge adapter is the component which carries the tubes from the distribution area 204 to the centrifuge bucket of the centrifuge.

If the distribution area module 204 determines that the sample tube does not require centrifugation and no other tubes are being placed onto the conveyance line by the centrifugation module 206, the distribution area robot gripper 218 places the sample into a carrier on the conveyance system 220 with the barcode label properly aligned to the carrier. More detail on the conveyance system 220 and the carriers will be discussed below. A carrier can refer to any suitable device, which can be present in a conveyance system and can carry or transport one or more sample containers or tubes. Exemplary carriers may contain recesses which can hold the containers or tubes. If a problem exists with the sample (e.g., the volume is too low, the barcode is unreadable, no test information is downloaded, etc.), the sample tube is moved to the error area 222 and the user is notified of the issue.

(c) Centrifuge Module

The sample tube may be moved from the distribution area 204 of FIG. 2 to the centrifuge module 206 if the distribution area module 204 determines that the sample requires centrifugation before analysis of the sample. When a sample tube is to be transported from the distribution area 204 to the centrifuge module 206, the sample tube is loaded by the distribution area robot gripper 218 into a centrifuge adapter at the distribution area 204. The adapters may locate and retain multiple tube sizes for centrifugation. The adapter sits in a shuttle 224 which moves between the distribution area 204 and the centrifuge module 206 once the adapter is filled with sample tubes. An adapter can be a device which holds sample containers, and can be used in a centrifuge. Such adapters are commonly constructed of a polymeric material but not limited to and constructed as a single piece having a shape which allows retention of one or more containers in which a sample may be placed. In some cases, an adapter is inserted into a device mounted on or in a centrifuge rotor. Labware (e.g., sample containers or tubes) holding the sample is inserted in the adapter.

When the sample tubes in the adapters arrive at the centrifuge module 206 from the distribution area 204 via the shuttle 224, the adapters are loaded into an available centrifuge bucket. The configuration of the adapters allows for simplification of delivery to and removal from the centrifugation buckets. Once loaded into a centrifuge bucket, the samples can be centrifuged. The centrifuge module 206 may include one or more centrifuges that are refrigerated to maintain the temperature of the sample. In FIG. 2, two centrifuges 206-1 and 206-2 are depicted. The centrifuges use a swinging centrifuge bucket rotor which produces level sedimentation layers from which analyzers and pipettors can consistently aspirate the maximum volume of fluid. Once centrifugation is complete, the adapters can be removed from the centrifugation bucket and placed in an unloading area. The sample tubes are then removed from the adapters in the unloading area and placed in carriers on the conveyance system 220 for transport to the next module.

The timing for loading tubes into an adapter at the distribution module 204, sending the tubes in the adapter to the centrifuge module 206 via the shuttle 224, loading the adapter into a centrifuge bucket, centrifuging the samples, unloading the adapter from the centrifuge bucket, and unloading the tubes from the adapter is such that the process is continuous, allowing for the continual centrifugation of samples as they arrive at the centrifuge module 206 from the distribution area 204. As the centrifuge completes a spin cycle, the last tube in the distribution area 204 is loaded by the distribution area gripper 218 into an adapter, and the shuttle 224 moves the adapter to a centrifuge in the centrifuge module 206. At the same time, an automated door on the centrifuge opens and provides access to a bucket as the rotor indexes into position at the doorway. A centrifuge module gripper 226 in the centrifuge module 206 removes the adapter that is already in the bucket and moves that adapter to an area where the tubes will be unloaded to carriers on the conveyance system 220. Next, the centrifuge module gripper 226 selects an adapter that has been recently loaded with tubes from the distribution area 204 and deposits it into the empty bucket. While the rotor indexes to the next bucket, a previously emptied adapter is moved to the open position on the shuttle 224 for loading with tubes from the distribution area 204 when the shuttle 224 returns to the distribution area 204.

After the final adapter is loaded into the centrifuge, the door closes and the spin cycle begins. The adapter shuttle 224 moves back to the distribution area 204, and a centrifuge module gripper 226 begins to unload tubes from the adapters removed from the buckets into carriers on the conveyance system 220. As the tubes are moved from the adapter to the carrier, the heights of the sedimentation layers are measured and the barcode on each tube is aligned with the carrier. If insufficient serum or plasma is present, the tube will be sent to an error area located in the output module 214.

If the scheduling algorithm predicts the overloading of an analyzer with samples from the centrifuge module 206, the centrifuge module gripper 226 can unload the samples and distribute the samples from the adapters to the conveyance system 220 only as quickly as the downstream process can handle them. As a result, the full cycle time of the centrifuges can be greater than or equal to, e.g., 360 seconds. If while operating two centrifuges, one of the unloading phases is delayed as a result of a busy analyzer, the trailing centrifuge can be kept, e.g., 180 seconds out of phase to ensure they do not drift into phase over time.

The centrifuge module 206 may include an automated centrifuge controlled by a centrifuge controller. The automated centrifuge can be loaded with multiple centrifuge buckets or receptacles, each bucket receiving multiple sample tubes. The centrifuge includes a motor coupled to a spindle that receives the buckets, a controller, and optionally, a lid, and a lid drive. The centrifuge controller indexes or stops the spindle at selected positions for automated placement and removal of the buckets in response to signals from the central controller. The lid has a closed position and an open position, and the lid drive opens and closes in response to instructions from the centrifuge controller.

In some instances, before the loaded buckets are placed in the centrifuge, the buckets are typically balanced in a balance system. The balance system, which can be an included part of the centrifuge module 206, comprises a scale having sites for receiving and holding a plurality of buckets, and a balance controller for selectively depositing sample tubes in cavities of the buckets while correlating incremental weight changes with the locations of each deposit for equalizing weight in pairs of the buckets. The balance controller can be implemented as a balance program within the central controller, the balance program maintaining a database of sample tube locations and associated weights, and directing the robotic arm for depositing the sample tubes. The balance system may also include a supply of dummy loads in buckets for limiting weight variations between buckets. The dummy loads may be weighted for limiting the weight variations to not greater than, e.g., 10 grams between members of each pair of buckets.

In other embodiments of the invention, a balance system need not be present or used in embodiments of the invention. As explained below, in embodiments of the invention, the weight of a sample tube can be automatically determined by an assembly that can determine a liquid level of a sample in the sample tube. Thus, embodiments of the invention are more efficient than systems requiring a balance system, because a sample tube weighting step need not be performed. Embodiments of the invention can also be less complex since a balance system is not needed in some embodiments of the invention.

The centrifuge controller may operate to perform a number of functions, such as receiving and storing a centrifuge spin profile including a rotor spindle speed and duration, indexing the rotor for advancing a selected one of the sample stations into an access position, spinning the rotor in accordance with the cycle profile, stopping the rotor with a predetermined sample station at the access position, etc.

(d) Decapper Module

The decapper module 208 of FIG. 2 is capable of decapping the cap from the sample tubes in carriers on the conveyance system 220 before they are analyzed. The decapper system may clamp a sample tube and remove the cap from a sample tube. The decapper module 208 follows the distribution module 204 and the centrifuge module 206. For sample tubes which do not require cap removal (e.g., for instances in which the samples may only require sorting), the carrier on the conveyance system 220 will bypass the decapper module 208. For sample tubes that require cap removal, the decapper module 208 may remove the cap from the sample tube and deposit the cap in a biohazardous waste disposal container below the deck of the decapper module 208. The biohazardous waste disposal container is removable and replaceable to protect the user from biohazardous waste.

(e) Serum Indices Module

The serum indices module 210 of FIG. 2 is capable of measuring the serum index of a sample. Typically, this function is performed during the analytical phase 106. However, in some instances, certain laboratories may prefer to address any quality issues prior to delivering the samples to the analyzer. Thus, the serum indices module 210 provides this quality control option for samples that should be tested. For samples that do not require a serum index measurement, the sample may bypass the serum indices module 210.

The serum indices module 210 can be the next module after the decapper module 208 since a serum indices measurement typically requires access to the sample. Similar to the decapper module 208, the serum indices module 210 may have a biohazardous waste disposal container below the deck of this module. The container may be removable and replaceable to protect the user from biohazardous waste.

(f) Aliquotter Module

Figure 3:
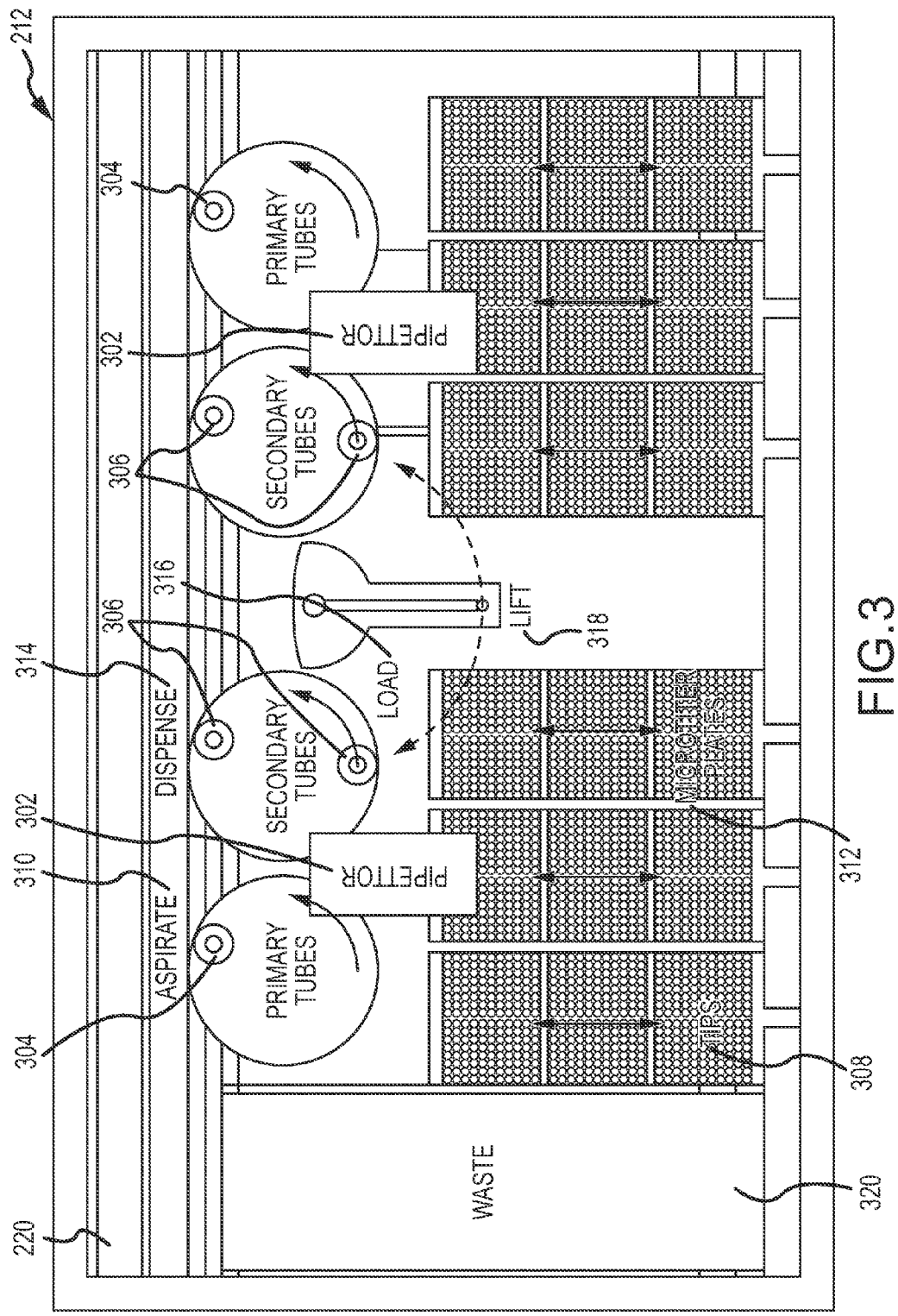
FIG. 3 depicts a block diagram of components within an aliquotter module.

The aliquotter module 212 of FIG. 2 is depicted in greater detail in FIG. 3. The aliquotter module 212 divides the primary sample 304 into multiple secondary tubes 306 depending on how many tubes are needed for analysis. This module may contain one or more pipettors 302 for dividing the primary sample 304 into secondary samples 306. The aliquotter module 212 further facilitates labeling of the secondary samples 306 with a barcode label specifying the patient and test information. The barcode labels are attached to the secondary tubes 306 below the deck of the aliquotter module 212 in a device called the Secondary Tube Preparation Unit (STPU). The STPU can produce labeled tubes faster than a single pipettor can transfer a sample. However, when two or more pipettors are incorporated, the STPU limits the combined throughput of the two or more pipettors. New secondary tubes can be delivered to the aliquotter module 212 in racks and loaded into drawers below the aliquotter module 212. The labels are delivered on a roll and printed below the deck of the aliquotter module 212 prior to attachment to the tubes.

To minimize contamination of patient samples, the pipettors 302 use disposable tips 308. These tips arrive in racks which are loaded into drawers on the deck. The pipettor 302 loads a disposable tip from these racks, aspirates 310 the sample from the primary tube 304 and dispenses 314 the sample into one or more secondary tubes 306 and/or a microtiter plate 312. In one embodiment, the tip may be limited to a particular amount (e.g., 1 milliliter) of the sample. In such a case, dispensing volumes exceeding that particular amount may require multiple aspirations. Once the pipetting is finished for a sample, the tip can be disposed in the waste container 320.

In order to manage the tubes during aspiration 310 and dispensing 314, the primary 304 and secondary 306 tubes are removed from the travel lane of conveyance system 220 and queued on supplementary lanes. Because the aliquotting module 212 may operate at a slower rate than the other modules, the queues minimize the effect of aliquotting on the remainder of the system. Although the queuing process may vary depending upon the conveyance system 220, the carriers with the primary tubes 304 are transferred to a queue wheel. Empty carriers for the secondary tubes 306 are transferred to a separate queue wheel adjacent to the primary tubes 304. The labeled secondary tube 306 is loaded 316 into the empty carrier from below the deck by a lift 318 which rotates around to align with the empty carrier. The STPU transfers the tube to the lift 318 in the correct orientation to ensure the barcode is aligned properly with the carrier. In the case of an aliquotter module 212 having more than one pipettor, the lift 318 rotates the opposite direction to place the tube in the carrier.

(g) Output/Sorter Module

FIGS. 4(*a*)-(*e*) depict examples of an output/sorter module 214. The output/sorter module 214 transfers tubes to and/or from racks located in drawers 402 or bays. The racks may be either analyzer racks, standard storage racks, or any rack that meets the Clinical and Laboratory Standards Institute (CLSI) standards. An output/sorter gripper 404 removes the tubes from the carrier and deposits them into the racks. If necessary, the barcode is aligned to the rack as desired. The output/sorter module 214 may have any number of drawers 402 and may have any number of output/sorter grippers 404. The number of output/sorter grippers 404 may depend on how many drawers 402 the output/sorter module 214 contains. That is, more output/sorter grippers 404 may be needed for output/sorter modules 214 having a large number of drawers 402. FIG. 4(a) depicts an example of single gripper output unit 406 that is connected to the conveyance system 220 and a standalone single gripper sorter with input and output 408. FIG. 4(b) depicts an example of a dual gripper sorter with input and output. Depending upon the application, the unit may be connected to the conveyance system 220 or it may operate as a standalone system.

The output/sorter module 214 can function as a component for handling the output of the pre-analytical phase 104 and can also function as a sorter for sorting tubes based on the type of analysis that the samples are to undergo. FIG. 4(c) depicts another embodiment of the output/sorter module 214. The output/sorter module 214 may include drawers for handling the output 414 of the pre-analytical phase 104, drawers for handling tubes that are inputted 410 to the output/sorter module 214 for sorting, and drawers for handling tubes that should be reentered 412 into the analytical phase for further analysis.

The output/sorter module 214 includes areas to load and/or unload racks of tubes. Additionally, some of the drawers on the output/sorter module 214 may be specified as input and some as output. In the sorter mode, the units with a single robotic gripper 404 select a tube from an input drawer, read the barcode, measure the height of the constituent sample components, make a photograph of the tube and analyze the data to record its manufacturer, diameter, height, and cap color. Based upon the information received from the laboratory information system (LIS), the gripper 404 deposits the tube in the correct rack while aligning the barcode as appropriate. If an error condition is identified, the tube is placed into an error rack.

An output/sorter module 214 having a larger number of drawers 402 and more than one output/sorter robotic gripper 404 may attain a higher throughput. A first output/sorter gripper 404 may perform the same functions as described above. However, since the destination is typically a single point on the conveyance system 220, it may not have to wait on information from an LIS (laboratory information system). As the tube is conveyed to the extraction point for a second output/sorter gripper, the LIS has time to respond with the appropriate information. The second output/sorter gripper may remove the tube from the carrier and deposit and align the tube in the appropriate rack. Because these units can function as either an input 410 or an output 414, they can be assembled together with the conveyance system 220 to create even larger input and/or output areas. FIG. 4(d) depicts an example of this embodiment of an output/sorter module 214. Units are combined with the conveyance system 220 to permit the creation of a sorter having an input 410 with five drawers and an output 414 with ten drawers.

3. Analytical Phase

Referring again to FIGS. 1 and 2, the analytical phase 106 includes performing the actual measurements needed to process a sample and produce results. This phase is typically composed predominantly of one or more analysis instruments or analyzers. The analysis instruments or analyzers can be any analysis instruments or analyzers known in the art. Typically an analyzer may comprise a mechanism for selectively performing one or more types of analyses on a specimen and an analyzer controller in communication with the central controller, so that the central controller can instruct the analyzer controller as to what analysis to perform for the specimen. Each analyzer may also include an output system for providing analysis results to the memory of the central controller.

For a laboratory system that has the components associated with the pre-analytical 104, analytical 106, and post-analytical 108 phases connected together via a conveyance system 220, the samples may move past the output/sorter module 214 and onto analyzers. When the carrier reaches the destination analyzer for that particular sample, the carrier pulls off the main travel lane and forms a queue upstream of the analyzer's access point to the conveyance system 220. The queue length is minimal because of the planning done by the scheduler while the tube was still in the distribution area 204 and because of the controlled release of tubes by the distribution 204 and centrifuge 206 modules.

Figure 4E:
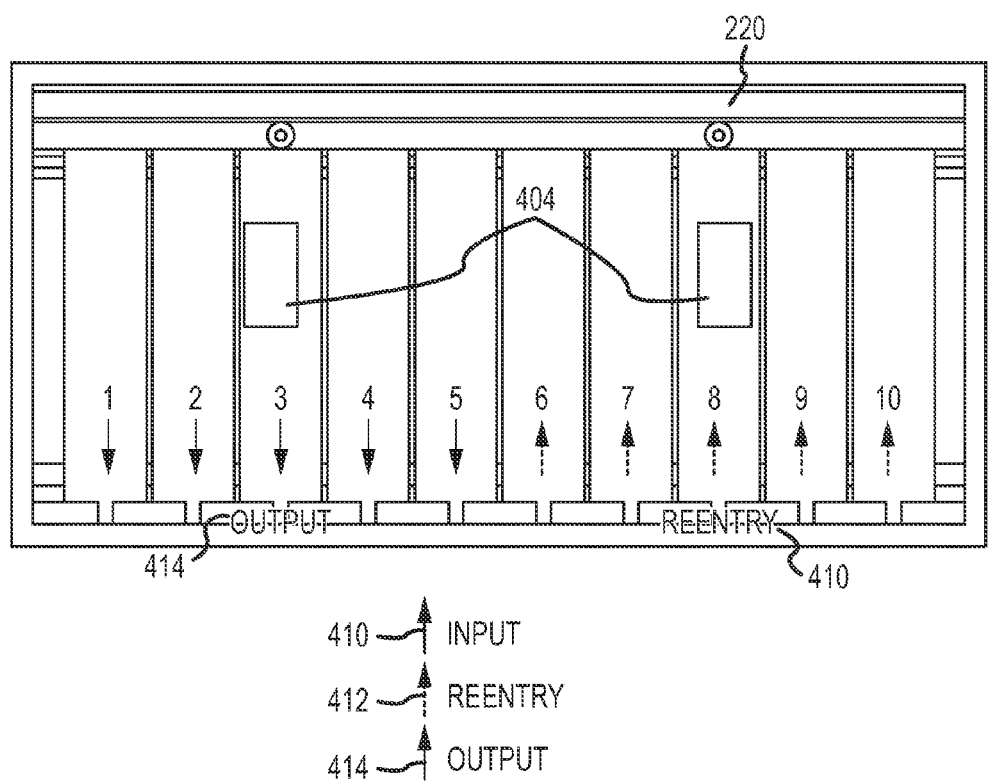

If some of the analyzers are connected via the conveyance system 220 and some are not, the samples destined for the unconnected analyzers will exit the system at the output/sorter module 214. However, these samples may need to reenter the connected system for additional processing. The reentry function of the output/sorter module 214 performs this function by inputting 410 the tubes that should reenter the system for analysis. Thus, since the output/sorter module 214 can function as an input 410, another module is not necessary, increasing the efficiency of the system. The location of this function may vary by the user's laboratory layout. In one embodiment, the location of this function may be adjacent to and downstream of the output/sorter 214 in the pre-analytical phase 104. In one embodiment, two separate frames are used to perform these functions, such as the example depicted in FIG. 4(d). In another embodiment, the functions can be combined into a single frame of an output/sorter module 214, as shown in FIG. 4(e). However, any combination of the configurations shown in FIGS. 4(a)-4(e) can be used.

The throughput of the output 414 and input 410 or reentry 412 may be tailored to match the needs of the user. For example, a user with few samples destined for an unconnected analyzer may only need an output/sorter module 214 that has one single output/sorter gripper 404. On the other hand, a user with no connected analyzers and high throughput may prefer a large output area and a separate sorter.

4. Post-Analytical Phase

The final phase of the laboratory process is the post-analytical phase 108. In this phase, the sample is prepared for storage and is stored. Once the sample has completed the testing and analysis required, the sample is capped and placed into storage. This may be either ambient or refrigerated storage depending upon the sample and the laboratory process. Moreover, users with systems having connected analyzers may desire a connected cold storage for some samples and offline ambient storage for others. However, users with unconnected analyzers will likely store all of their samples offline.

Figure 5:
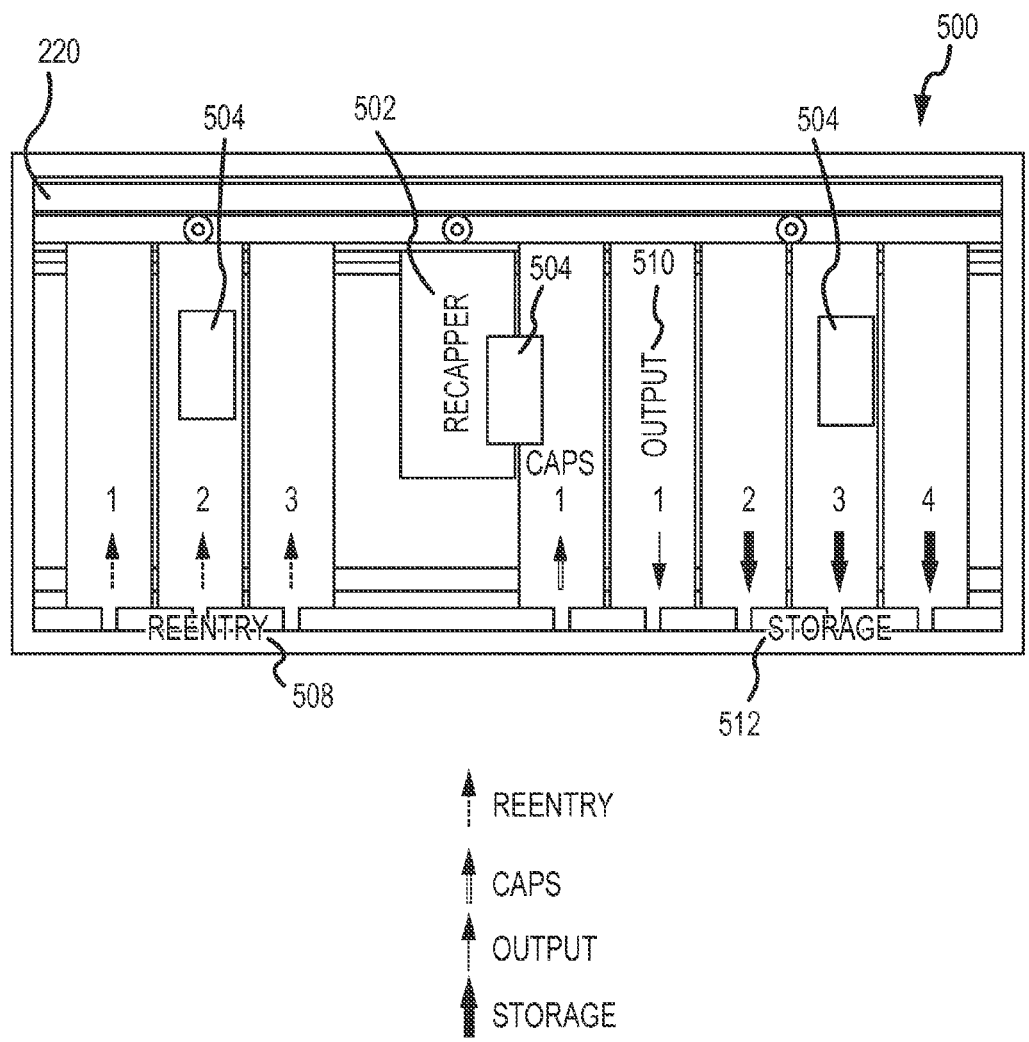
FIG. 5 depicts a block diagram of a configuration of a sorter module coupled to a capping device.

The user with unconnected analyzers may use a sorter in combination with a capping device to prepare their samples for storage. FIG. 5 depicts an example of a sorter module 500 coupled to a capping device 502. The sorter module 500 may be similar to the output/sorter modules 214 depicted in FIGS. 4(a)-(e). When a tube completes a test, the user loads the sample on the input or reentry side 508 of the sorter and retrieves the sample on the output side 510. The samples are transferred via the conveyance system 220 using robotic grippers 504 at the reentry side 508, the recapper 502, and the output side 510. The output side 510 of the unit has areas for storage racks 512 and/or racks for tubes requiring additional testing. The samples requiring additional testing are delivered to the subsequent analyzers and subsequently returned to the sorter unit 500. Because this process is operationally intensive on the sorter unit 500 with multiple passes, this part of the process can be properly sized for the lab throughput to prevent unnecessary backups. Once the samples are capped and placed into a storage rack 512, the racks are removed and stored elsewhere in the lab.

Figure 6:
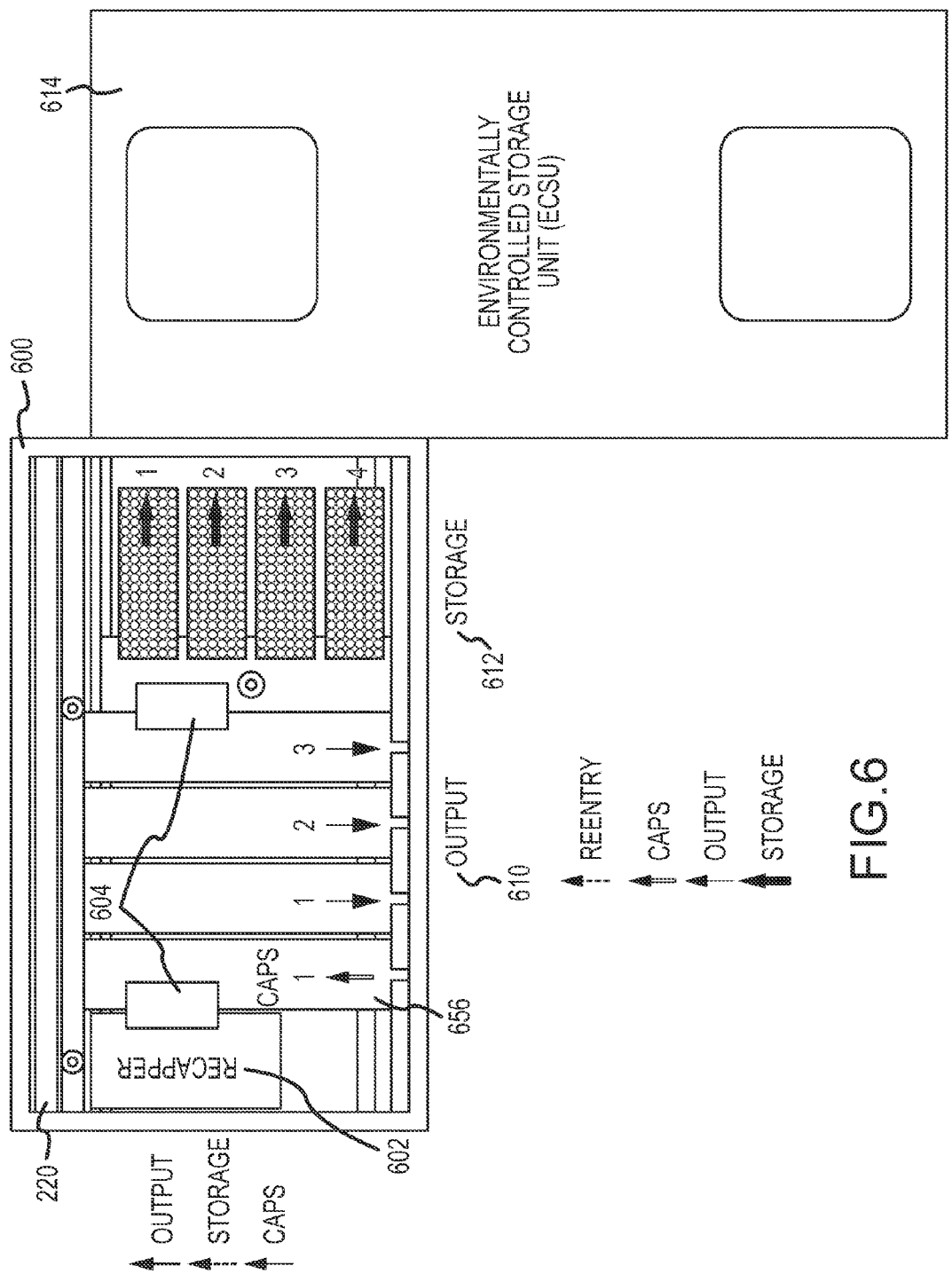
FIG. 6 depicts a block diagram of components within a post-analytical phase of the laboratory automation system.

A user with connected analyzers may prefer to have a connected refrigerated storage unit, as shown in FIG. 6. In the example shown in FIG. 6, the sorter 600 performs similar functions to those performed by the sorter unit 500 in FIG. 5. That is, the sorter 600 may take a sample from the conveyance system 220 using a robotic gripper 604 and recap samples using the recapper 602 and caps from the cap drawer 656. The recapped samples may be either outputted 610 or sent to storage 612 using the robotic gripper 604. In some cases, the sample may be output so that it can be sent to an ambient storage unit or it may be stored in a refrigerated storage unit. Samples can be retrieved automatically from the refrigerated storage unit for any additional testing that may be needed.

A special environmentally controlled storage unit (ECSU) 614 may been designed to store up to any number of tubes (e.g., 15,000 tubes). The unit may contain racks which can hold multiple size tubes with caps that may minimize the space required between tubes. As shown in the example of FIG. 6, four of the storage racks 612 may be arranged on the surface of a rack builder module to permit continuous loading or unloading and access to stored samples for reruns. During low system input, the ECSU 614 may have the ability to retrieve expired samples and dispose of them in a waste container below the deck of the rack builder module.

As samples enter the sorter unit 600, the recapper 602 applies a cap as necessary. The recapper 602 may have access to different types of caps. For example, from a vibratory bowl feeder, the recapper 602 can access a push style cap, and from a drawer, the recapper 602 can access screw style caps which are arranged in racks loaded on a drawer. After the capping process, a robotic gripper 604 removes the tube from its carrier and deposits and aligns the tube into a storage rack 612. The storage rack may be located on an output drawer 610 or on a position destined for the ECSU 614. When the rack is ready for storage, the ECSU 614 retrieves the rack from the deck and loads it into a matrix inside the ECSU 614. The ECSU 614 may be any size and can accommodate any number of tubes.

When requested, the ECSU 614 may have the ability to retrieve tubes for additional testing. It may also be capable of disposing of samples when they reach their expiration date. In one embodiment, this may be done concurrently with archiving but at a lower priority. A biohazardous waste container may be kept below the deck. Tubes entering the waste container may be capped to minimize the contamination through splashing of biohazardous waste.

In some embodiments, the ECSU 614 may not be large enough to archive all of a laboratory's samples prior to their expiration. Thus, periodic emptying of samples may be performed. This is accomplished via large doors on the backside of the ECSU 614. When the doors are open, the racks can be retrieved from the storage matrix. The racks chosen for removal are identified for the user to reduce the possibility of removing the incorrect rack. The racks may be removed individually from the unit and transported on a laboratory cart to an offline storage unit such as a walk-in refrigeration unit.

If a sample is requested from the offline storage unit, the rack can be reloaded onto the ECSU 614 and retrieved by the ECSU 614, or the user can remove the tube and load it onto the input or reentry 508. If samples expire while in the offline storage, the racks can be reloaded onto the ECSU 614 and disposed by the ECSU 614, or the user can dispose of the samples manually.

B. Functional Units of Laboratory System

As discussed above, the components of the laboratory system generally described above can be grouped into basic functional units, as many phases and modules may perform functions similar to functions performed in other phases or modules. In one embodiment, components can be grouped in five basic functional units: (1) manager, (2) centrifuge, (3) aliquotter, (4) output/sorter, and (5) storage units. For simplicity, the functional groupings will be discussed with respect to these five functional units. However, any functions can be grouped in any manner. Grouping the functions into general functional units allows for the design of the laboratory system to be somewhat general, flexible, and easily configurable for any user and the user's laboratory needs, so that the design of a highly customizable system for each lab is not necessary. Within each of the functional units, the specific functionality may vary depending on the laboratory's needs. These functional units may enable the design of standard products that, when combined in various ways, may satisfy any laboratory's needs with a minimal number of standard products.

Figure 7A:
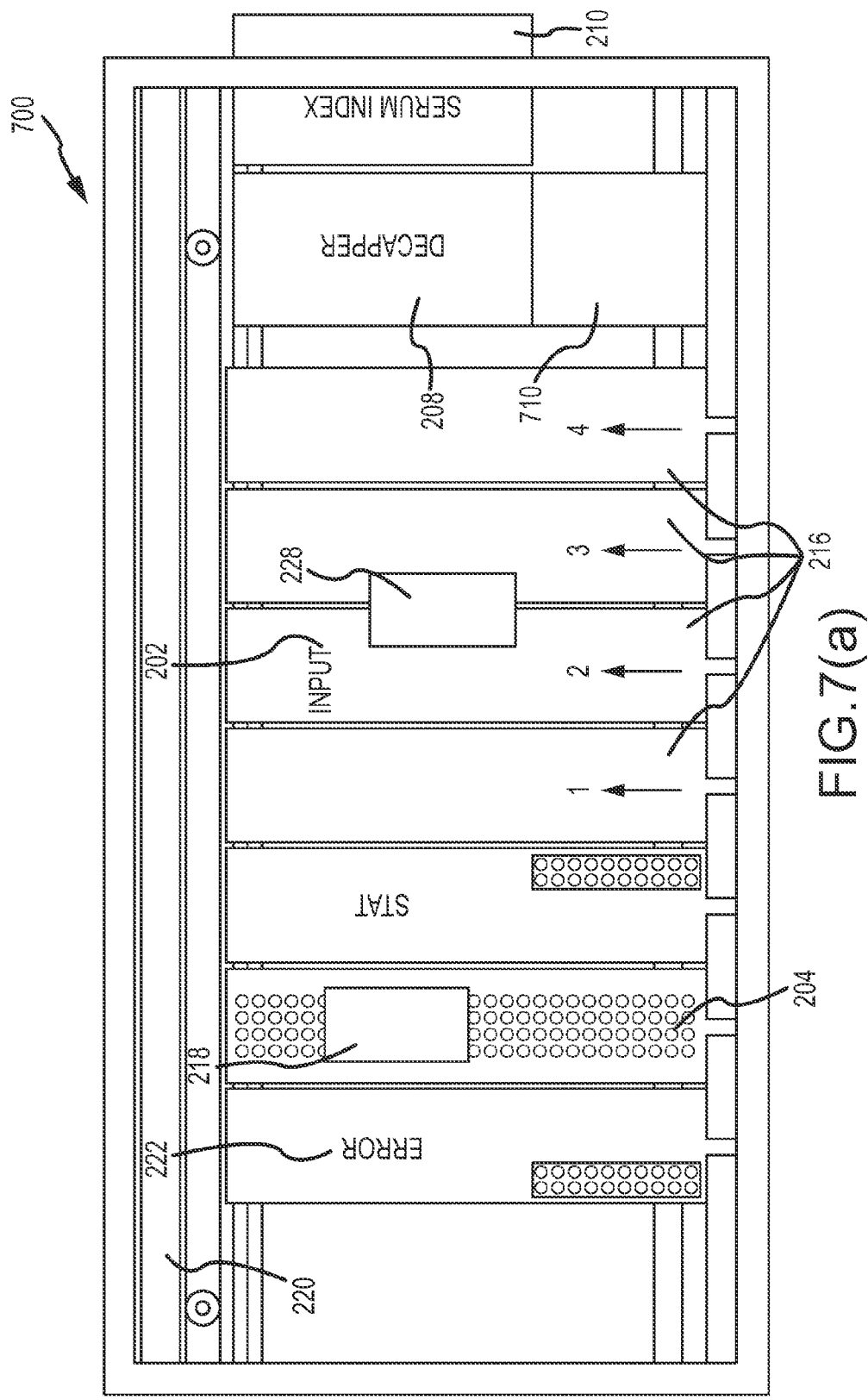
FIG. 7(a) depicts a block diagram of components associated with a manager unit.
Figure 7B:
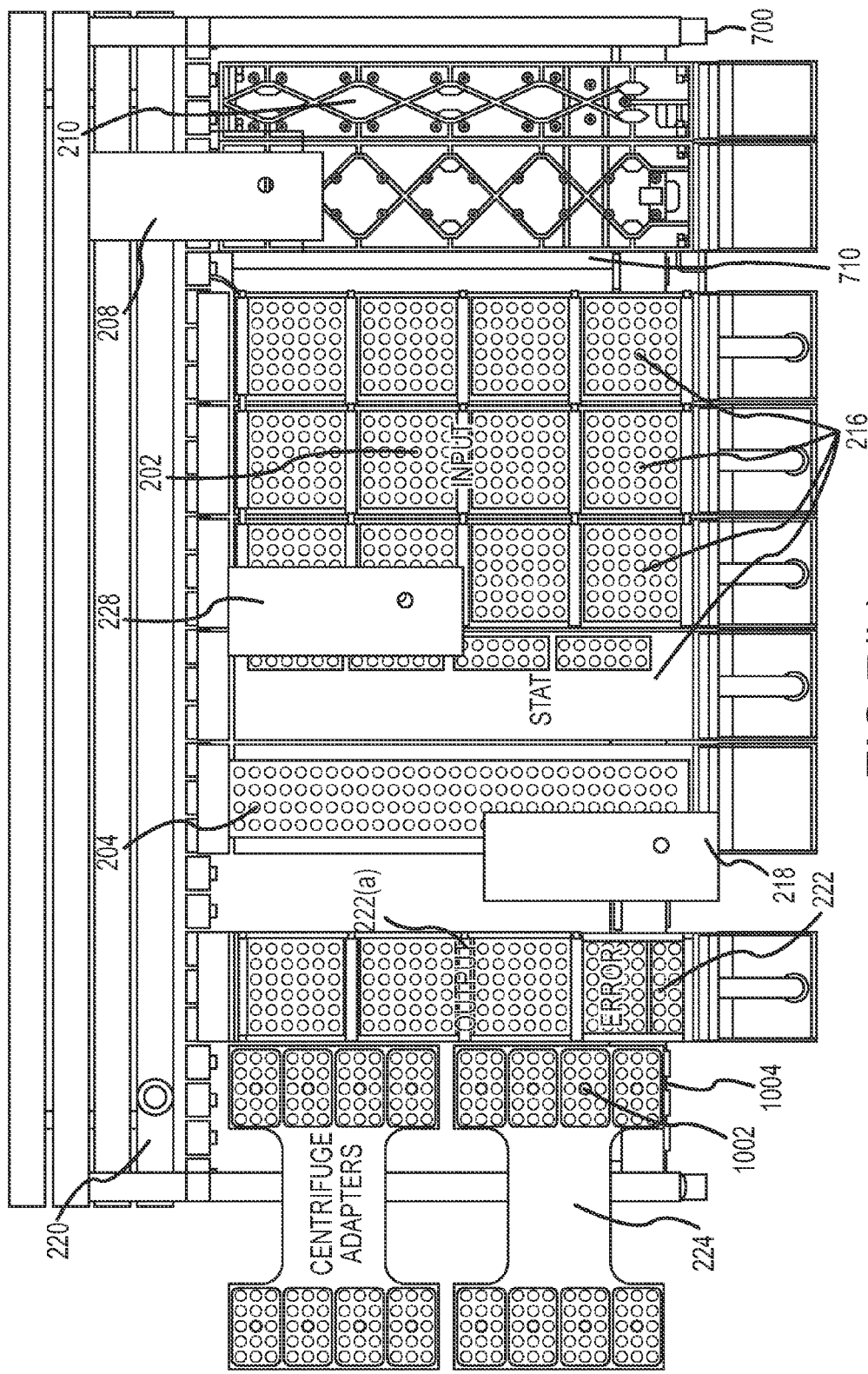
FIG. 7(b) depicts a block diagram of components associated with another manager unit embodiment.

FIG. 7(*a*) depicts an example of a manager unit 700. The manager unit 700 depicted in FIG. 7(*a*) includes the input module 202, the distribution area 204, the decapper 208 with a decapping robot 710, and the device for measuring the serum indices 210 from the pre-analytical phase 104 (see the description with respect to FIG. 2). Depending on the needs of the laboratory, any of the modules may be omitted and/or configured within the manager unit 700. For example, based on the laboratory's needs, the area for holding samples 204 while a process routing plan is prepared and/or the device for measuring the serum indices 210 of the sample may be omitted. FIG. 7(*a*) also shows a STAT drawer as well as an error drawer 222.

FIG. 7(*b*) shows another manager unit embodiment. In FIGS. 7(*a*) and 7(*b*), like numerals designate like elements. FIG. 7(*b*) specifically shows an error area 222 in an output drawer 222*a*. FIG. 7(*b*) also shows a conveyance system 220, a shuttle 224, a centrifuge adapter 1002, and a centrifuge loading position 1004. These elements are discussed in further detail below.

Figure 8A:
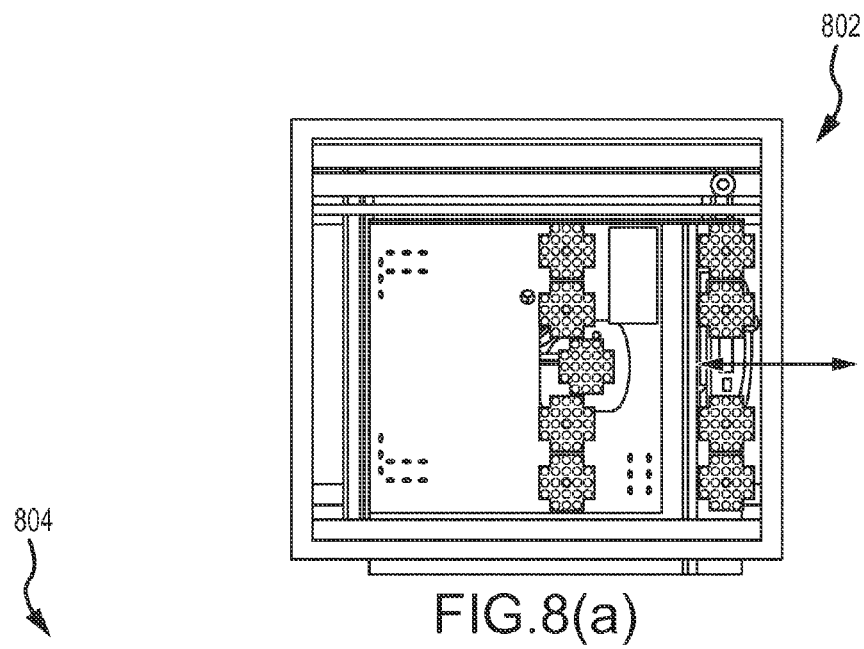
FIGS. 8(a)-(b) depict block diagrams of components associated with centrifuge units.
Figure 8B:
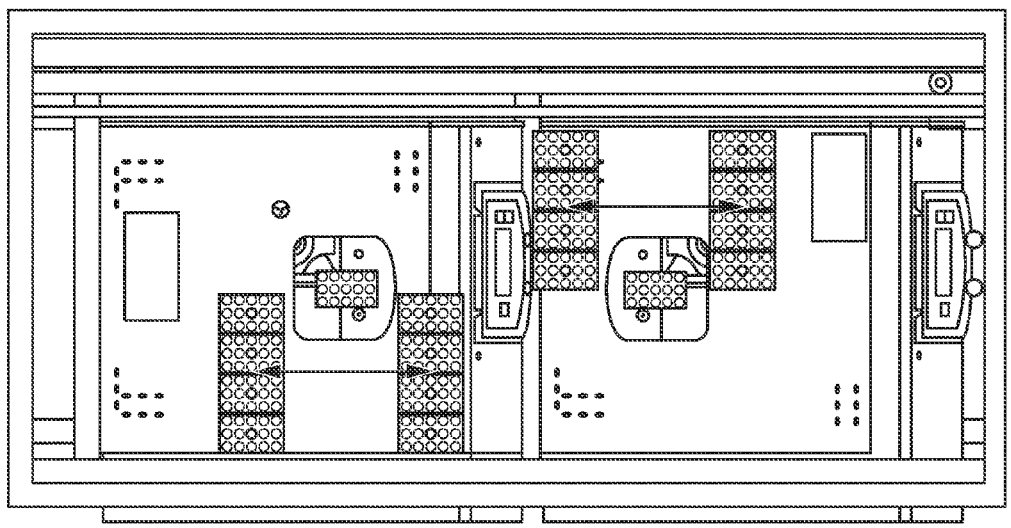

FIG. 8(*a*) and FIG. 8(*b*) depict examples of centrifuge units. The centrifuge units include centrifuges that are capable of centrifuging a specimen. The centrifuge unit 802 in FIG. 8(*a*) depicts a single centrifuge unit, while the centrifuge unit 804 in FIG. 8(*b*) depicts a double centrifuge unit. However, the centrifuge unit may have any number of centrifuges depending on the needs of the laboratory. The centrifuge units may be used as part of the centrifuging module 206 in the pre-analytical phase 104 described in FIG. 2.

One example of the aliquotter unit can be found in FIG. 3. An aliquotter unit may be capable of pipetting a specimen. FIG. 3 depicts an example of a double aliquotter unit having two pipetting functions. However, any number of pipettes can be included in the aliquotter unit depending on the needs of the laboratory.

Examples of output/sorter units are depicted in FIGS. 4(*a*)-(*e*) and FIG. 5. Any output/sorter configuration can be used based on the needs of the laboratory. Typically, the output/sorter unit is capable of receiving a specimen from the manager unit, centrifuge unit, aliquotter unit, and/or an analyzer. The output/sorter unit may include areas to load and/or unload racks of tubes and may include any number of robotic grippers for performing any functions necessary for the laboratory.

One example of a storage unit is depicted in FIG. 6. Depending on the needs of the laboratory, the storage unit may be capable of storing a specimen and may include a device to install caps on tubes, areas for tubes to be loaded into racks using robotic grippers, and attached storage units.

C. Exemplary Pre-Analytical Phase System

1. Pre-Analytical Phase System Layout

Figure 9:
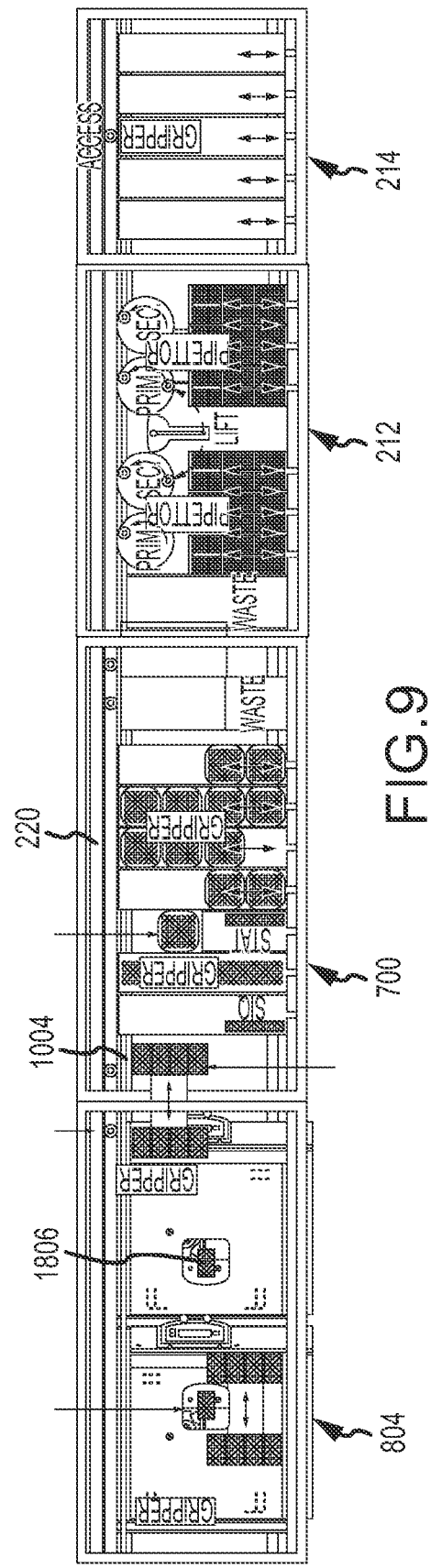
FIG. 9 depicts a block diagram of components within a pre-analytical phase of the laboratory automation system.

FIG. 9 depicts a detailed example of the manager unit 700, centrifuge unit 804, the aliquotter unit 212, centrifuge loading position 1004, and the output/sorter unit 214 of the pre-analytical phase 104. Each of these units will be described in more detail below.

Figure 10:
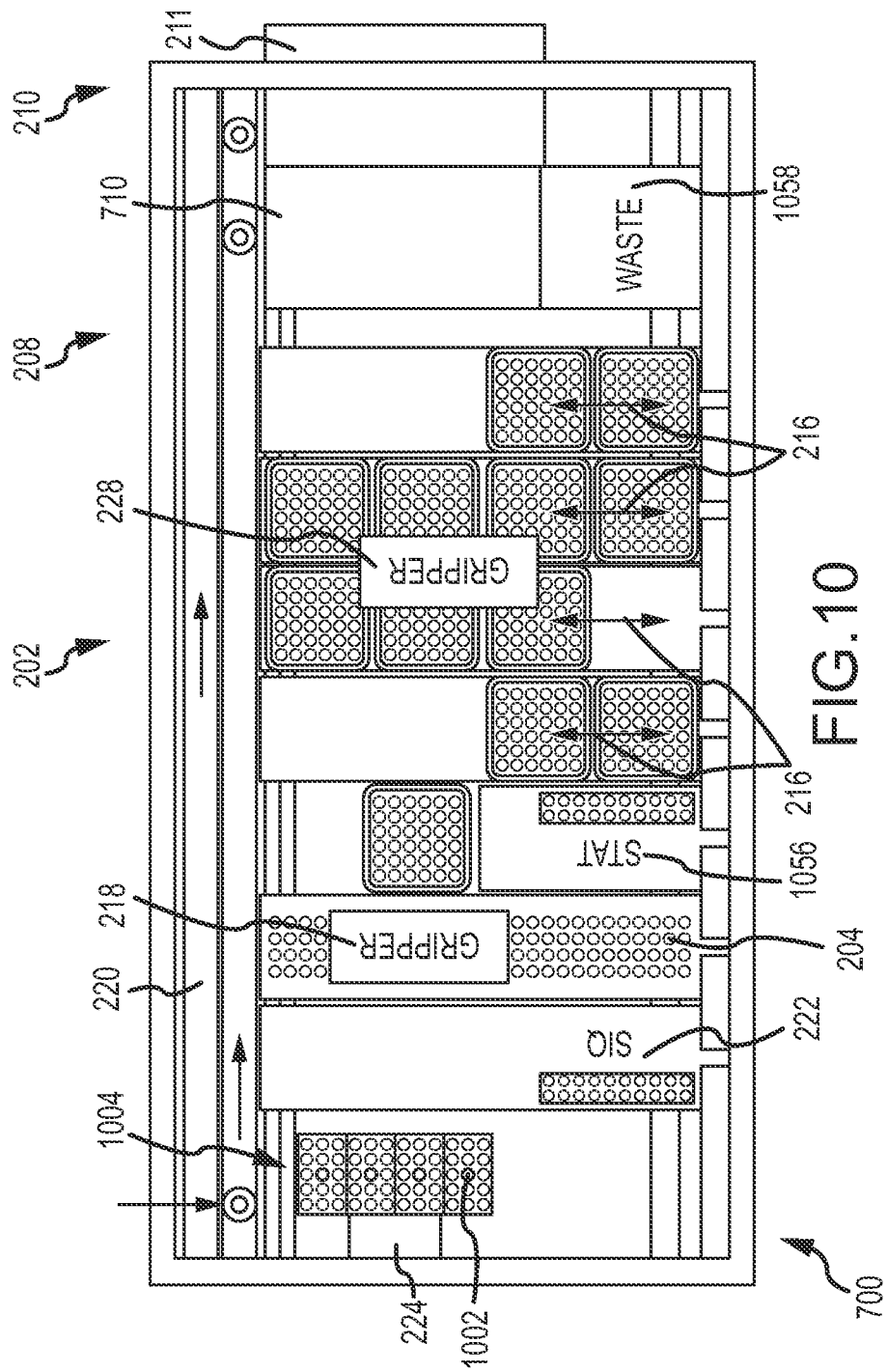
FIG. 10 depicts a block diagram of components associated with a manager unit.

FIG. 10 depicts a closer view of the manager unit 700. The manager unit 700 of FIG. 10 includes the input module 202, the distribution area module 204, the decapping module 208 with a decapping robot 710, which were described in more detail in the description of FIG. 7(*a*), and the serum indices module 210 with serum indices measurement unit 211. The input module 202 includes input drawers 216, including a STAT drawer 1056 loaded with sample racks, and an input robot 228 that can grip a sample tube, read a barcode, identify the tube by the characteristics, and can detect the sample level within a tube. The distribution area module 204 includes a distribution robot gripper 218 for gripping sample tubes, an error drawer 222, and centrifuge adapters 1002. The centrifuge loading position 1004 is the location for loading the centrifuge adapters 1002 with sample tubes that are to be sent to the centrifuge module 206 via a shuttle 224. The decapper module 208 includes the decapping robot 710 and the waste container 1058.

Figure 11:
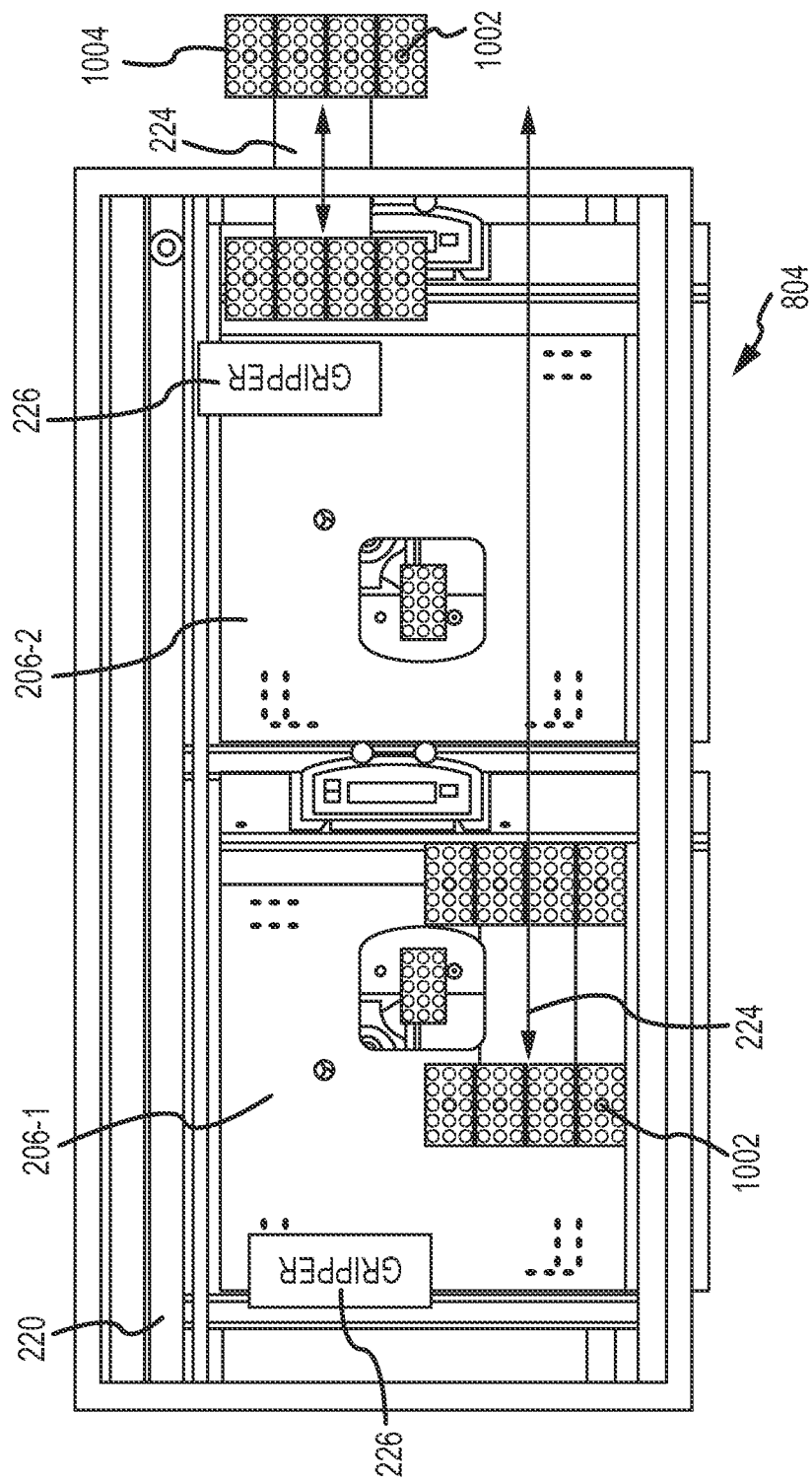
FIG. 11 depicts a block diagram of components associated with a double centrifugation unit.

FIG. 11 depicts a closer view of a double centrifuge unit 804, which was described in more detail in the description of FIG. 2. The centrifuge unit 804 includes two single centrifuges 206-1 and 206-2, an adapter shuttle 224 holding centrifuge adapters 1002, and centrifuge module robotic grippers 226.

Figure 12:
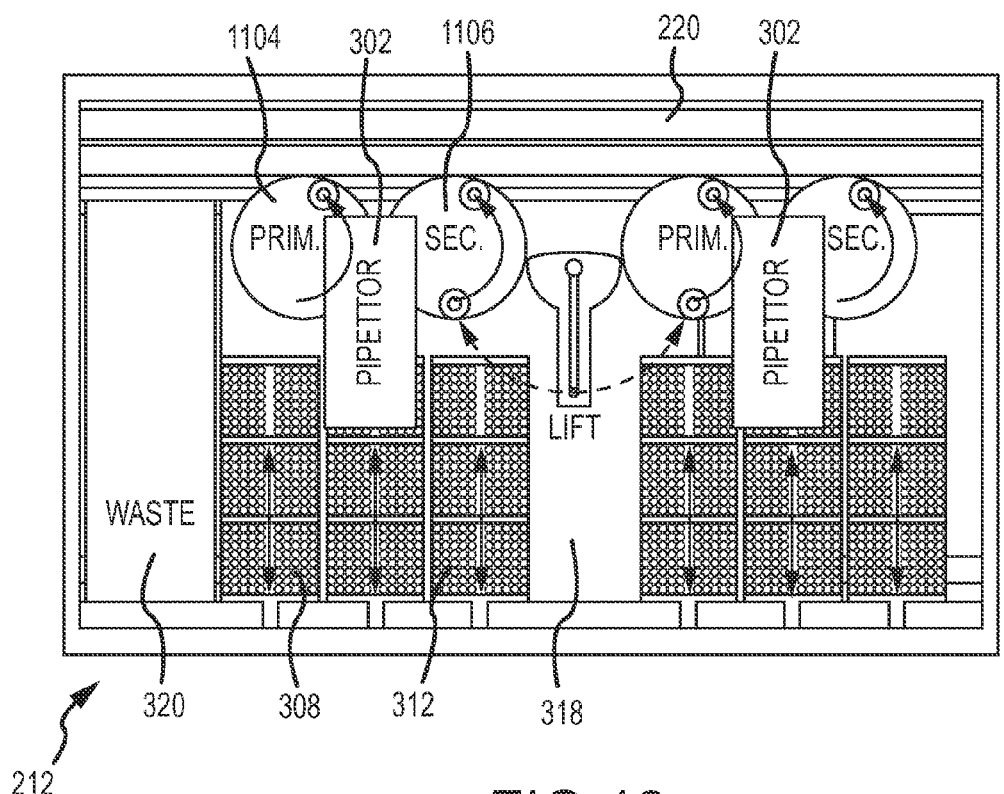
FIG. 12 depicts a block diagram of components associated with a double aliquotter unit.

FIG. 12 depicts a closer view of a double aliquotter unit 212, which was described in more detail in the descriptions of FIG. 2 and FIG. 3. The aliquotter unit 212 includes a primary tube queue 1104, a secondary tube queue 1106, a secondary tube lift 318 with tube storage and a labeler below the secondary tube lift 318, a waste container 320, a pipette robot 302, tip drawers 308, and microplate drawers 312.

Figure 13:
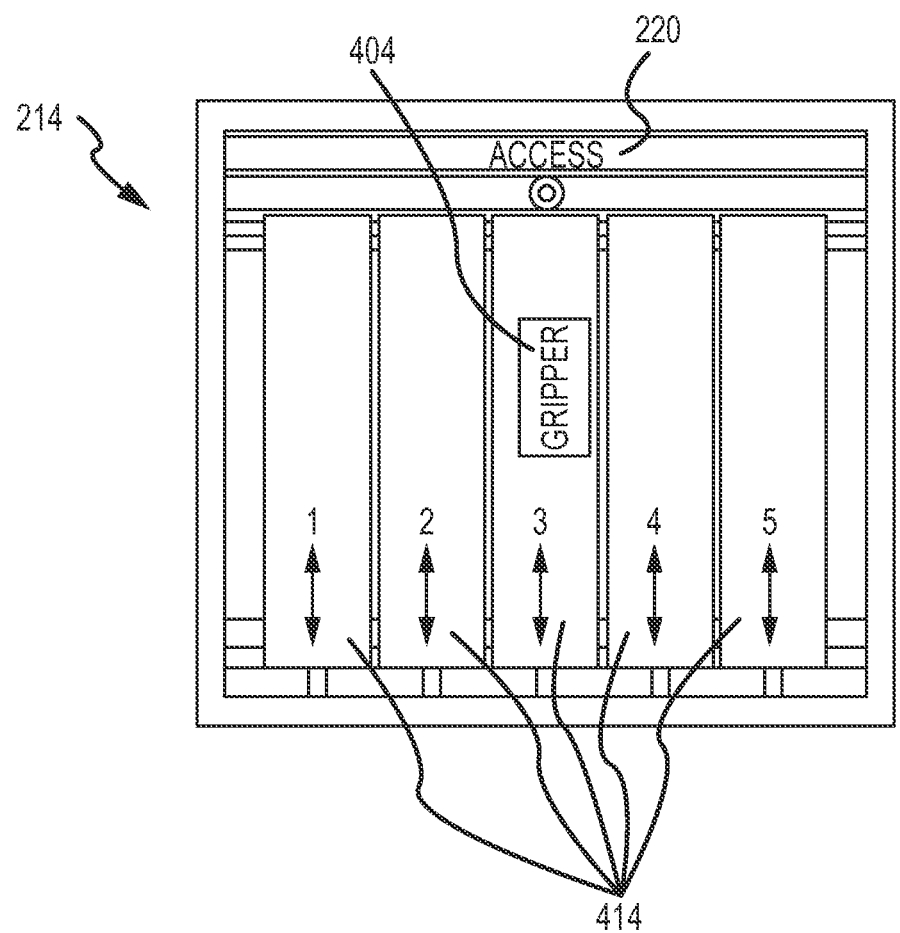
FIG. 13 depicts a block diagram of components associated with an output/sorter unit.
Figure 14A:
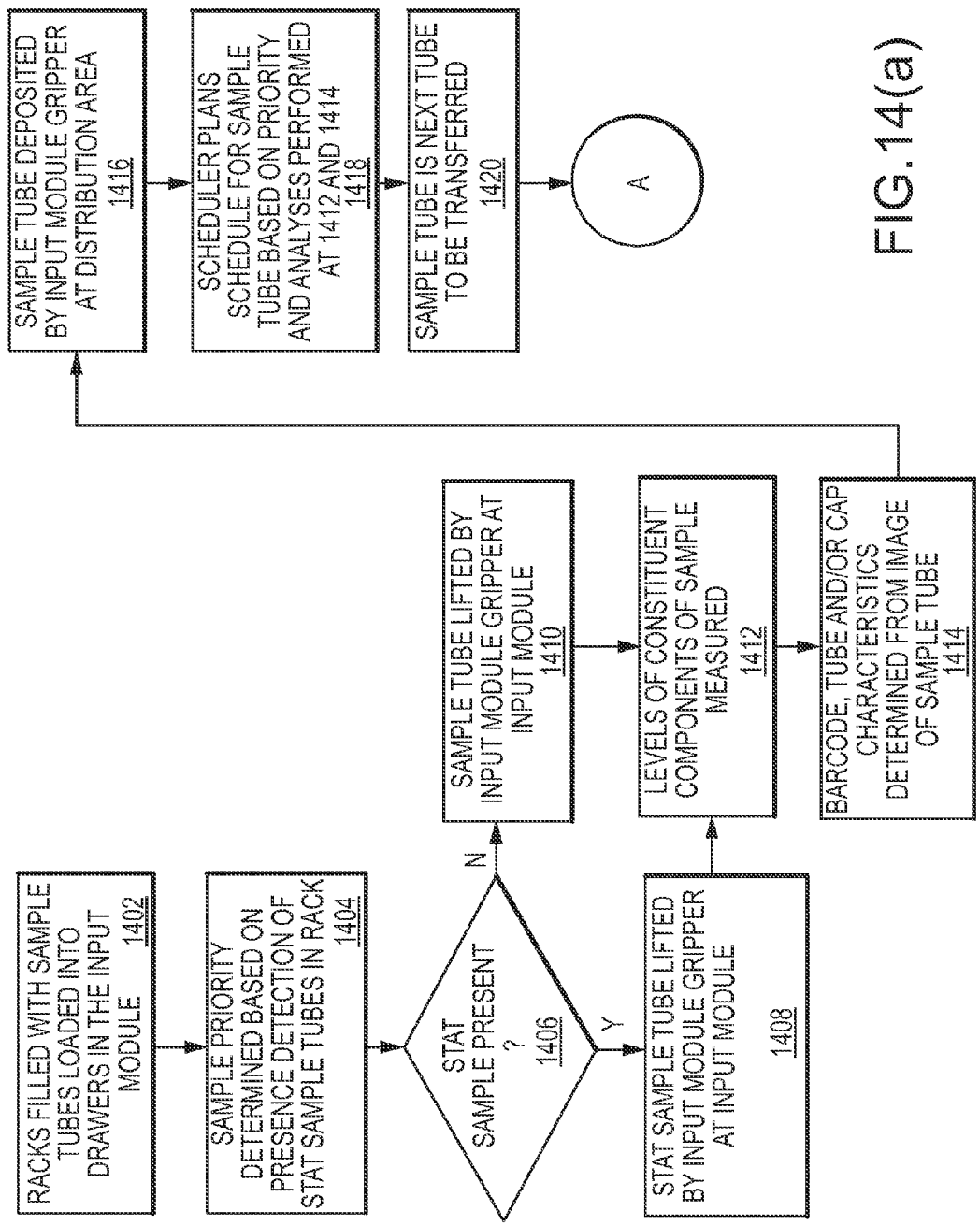
FIGS. 14 (a)-(d) are parts of a flow chart showing an illustrative example of the pre-analytical phase system workflow.
FIG. 14(e) shows a flowchart illustrating a method for selected an appropriate sample.
Figure 14B:
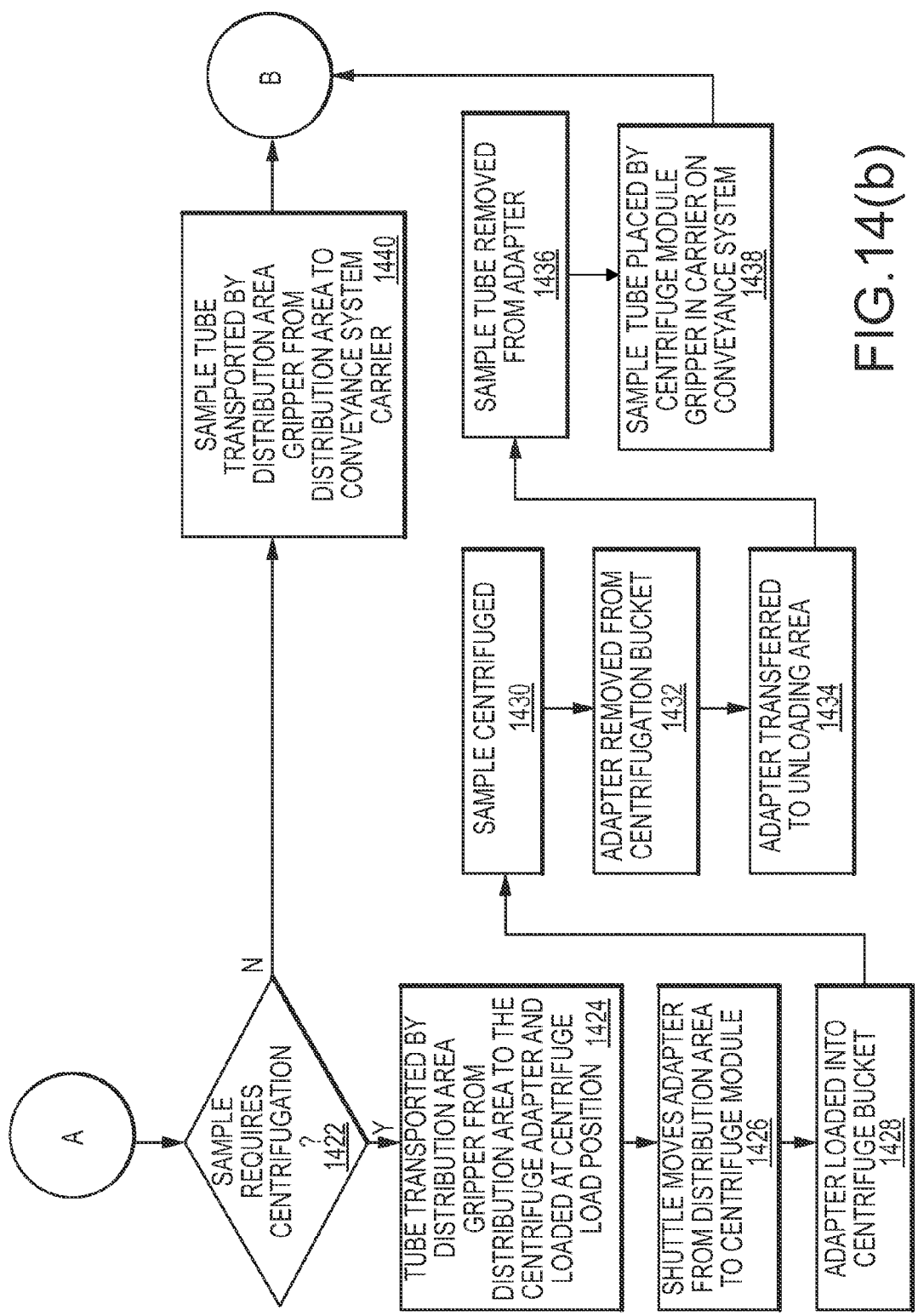
Figure 14C:
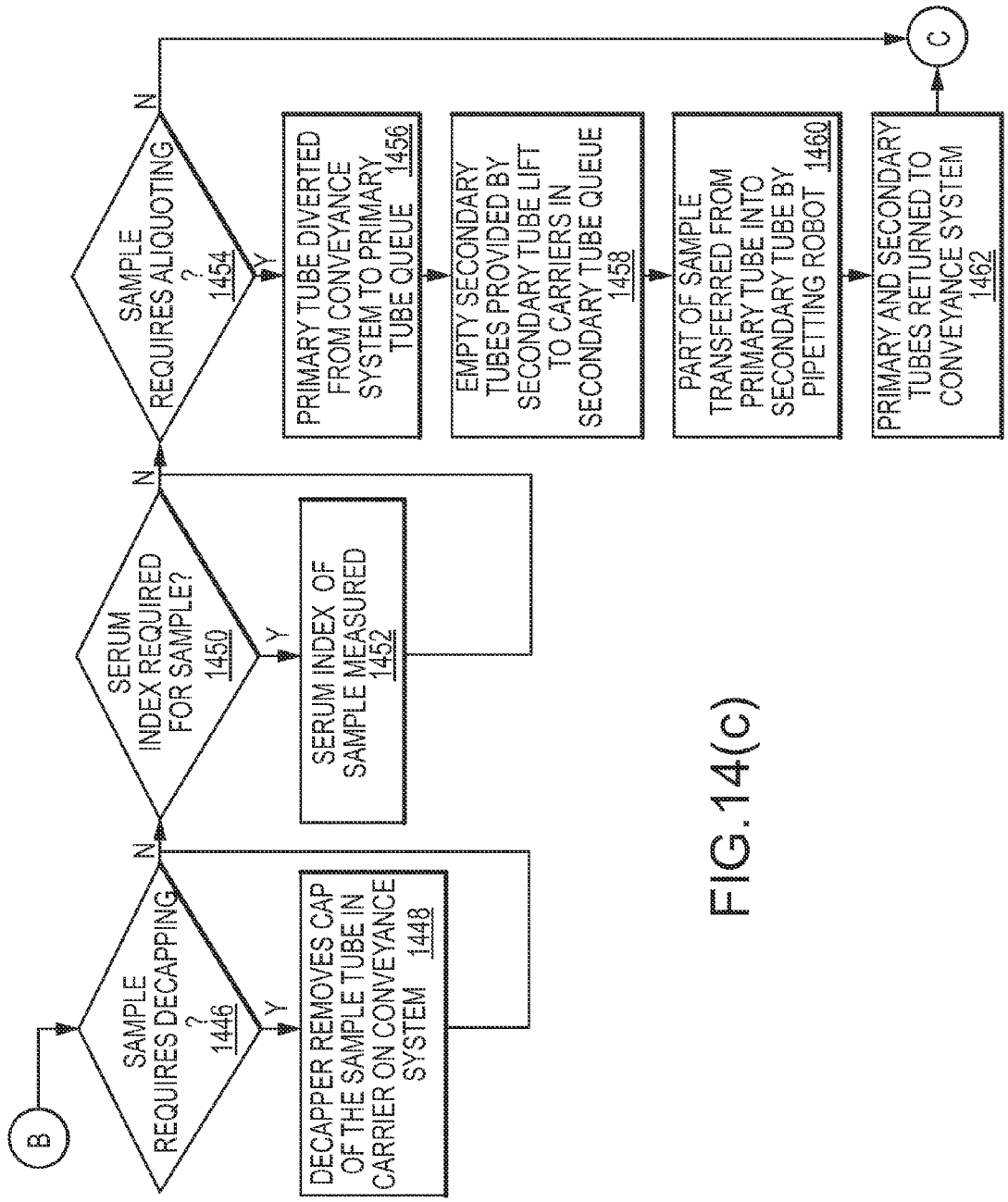
Figure 14D:
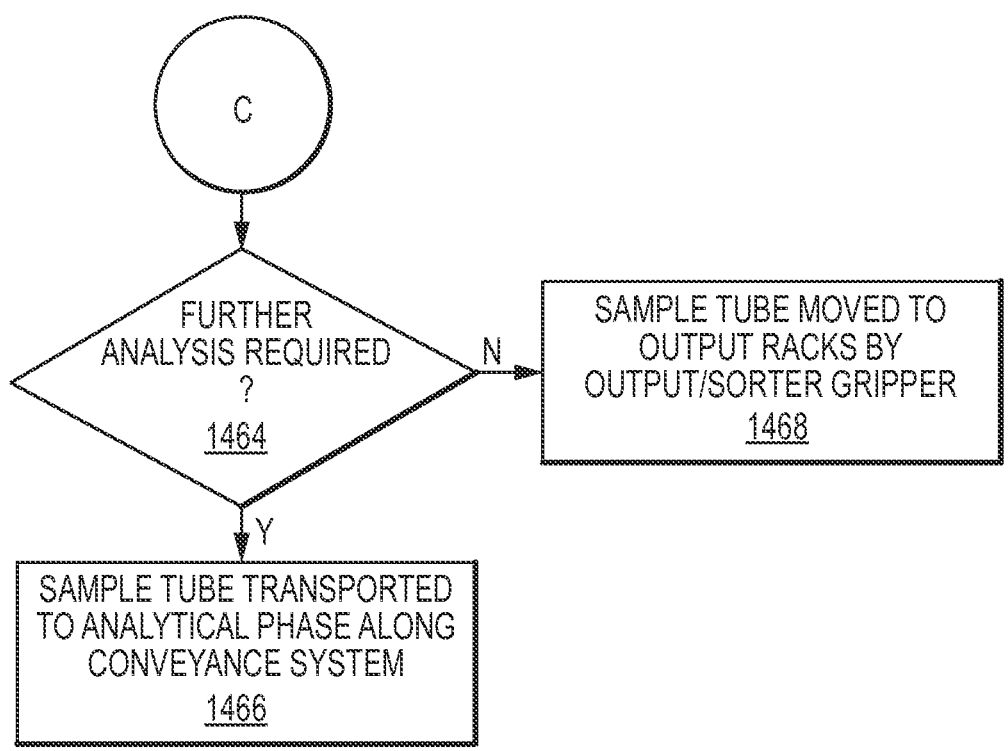
Figure 14E:
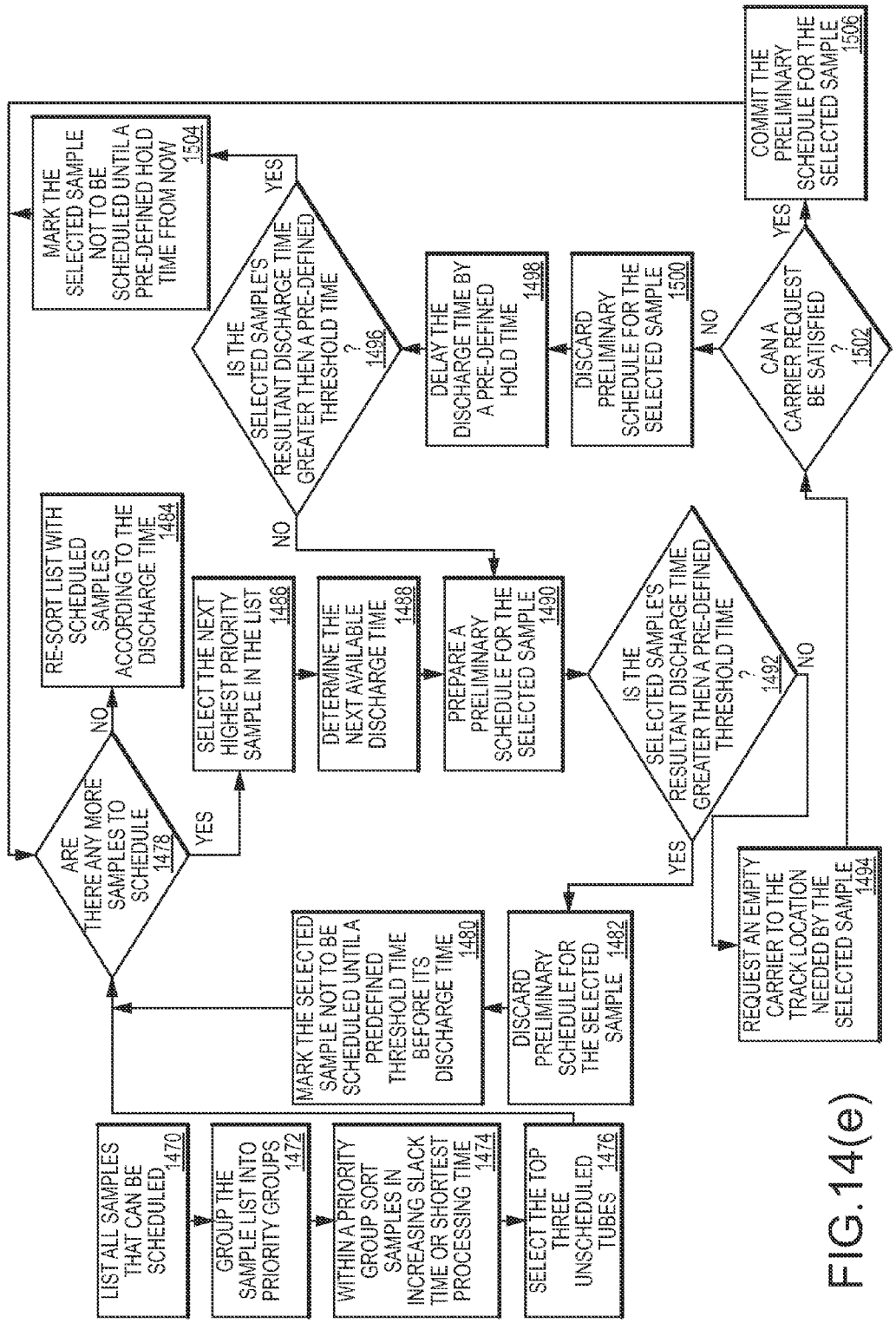

FIG. 13 depicts a closer view of an output/sorter unit 214 that is capable of recapping sample tubes and outputting, sorting, and/or storing the samples tubes. The output/sorter unit 214 of FIG. 13 includes an output robot 404 and output drawers 414. The components of the output/sorter unit 214 are described in more detail in the description for FIGS. 4(*a*)-(*e*) and FIG. 5.

2. Pre-Analytical Phase System Workflow

As discussed above, the pre-analytical phase may contain seven modules. FIGS. 14(*a*)-(*d*) are parts of a flow chart showing an illustrative example of the pre-analytical phase system workflow, which is described with reference to FIGS. 9-12.

Referring to FIG. 14(*a*), at the beginning of the pre-analytical phase, the racks 1806 that are filled with sample tubes are loaded into drawers 216 in the input module 202, as indicated at operation 1402. The processing priority for a sample tube may be indicated by placing the sample tube in the STAT drawer 1056 of the input module 202 or by applying a sample tube marker to the sample tube cap, detectable by a tube and rack presence detection unit that will be described in more detail below. The sample priority is determined based on whether a STAT sample tube is located in the rack, as indicated at operation 1404. The pre-analytical phase system then selects sample tubes from the input module 202 based on processing priority, as indicated at operation 1406. If a STAT sample tube is detected, the STAT sample tube will be the first tube to be lifted by an input module gripper 228, as indicated at operation 1408. If no STAT sample tube is detected, a sample tube that is not a STAT sample tube is lifted by input module gripper 228, as indicated at operation 1410. The levels of the constituent components (e.g., gel or packed red blood cells) of the sample in the sample tube are measured, as indicated at operation 1412. The levels of the constituent components of the sample may be measured as the tube is lifted by the input module gripper 228. The liquid level may be determined from a means for inspecting a tube. For example, the liquid level may be determined from a 2-D image captured of the tube contents, as described below. In some embodiments, the liquid level is determined using an absorption and transmission measurement unit, as described below. While the tube is in the input module gripper 228, a 2-D image (e.g., a photograph) is taken of the tube. One or more of the barcode, tube, and cap characteristics are determined by analyzing the image of the tube, as indicated at operation 1414.

In some embodiments, all samples have a priority assigned to them either through information found in the LIS (laboratory information system) or based upon the rack or position in which they reside within the Input. Sample tubes are selected from the input module are in order of priority. If the priority assigned by the LIS and the priority assigned due to the sample's location in the input module do not agree, the sample is assigned the highest priority of the two. Within a priority level, samples are selected by time of entry to the Input (i.e. first in first out, FIFO). Finally within a rack samples are selected in an established order (e.g. left to right and back to front). STAT samples have the highest priority.

At operation 1416 the sample tube is deposited by input module gripper 228 in the distribution area 204. The barcode of the sample tube may be oriented by input module gripper 228 so that it may be later read. Orientation of the barcode may occur before the move, during the move, or after the move of the sample to the distribution area 204.

While the samples sit in the distribution area 204, several processes for optimizing the functioning of the system may be performed within the distribution area. A scheduler may perform some of these processes. As described above, the scheduler may be a control processor and/or software which schedules the processing of each sample tube in order to organize and optimize the flow of sample tubes through the laboratory automation system. In general, the processor may generate a route plan for each sample based on the availability of processing units (including analyzers having queues) and schedules all samples located in the distribution buffer based on single route plans and prioritization for each sample. In some embodiments, the test information and a route plan may be generated by and/or retrieved from a scheduler based on the type of testing needed and the urgency associated with the sample. The scheduler may also take into account and use sample information (e.g., weight, cap color, spun, STAT (short turn-around time), etc.) to develop test information and the route plan. One example of a scheduler can be found in U.S. Pat. No. 6,721,615, which is herein incorporated by reference in its entirety for all purposes.

The scheduler may also determine which sample out of the plurality of samples sitting in the distribution area 204 is the next appropriate sample to begin processing. The appropriate sample may be one that is selected from a list of samples residing in a distribution area. It may be the sample with the highest priority and/or the sample that can be processed using the resources available according to its route plan to maximize throughput and/or TAT (turn around time). If a sample requires centrifugation, the weight of the tube may be calculated based upon the tube and cap characteristics, sample levels, and a density estimate made within the distribution area. In some embodiments, a database accessible to a central processor may store data relating to various types of sample containers. The data may comprise the weight of the containers (without any samples in them) as well as their dimensions (e.g., the inner diameter and height). The database may also store information regarding the densities of various types of samples. The weight of the sample may be determined using the liquid level of the sample in a sample container and the inner dimensions of the sample container. The weight of the sample container (without a sample) can be retrieved from the database to determine the total weight of the sample and the sample container.

A process for selecting an appropriate sample can be described with reference to FIG. 14(*e*). FIG. 14(*e*) shows a flowchart. As shown in the flowchart, the selection of the appropriate sample can be somewhat dynamic in nature and can change based on a number of factors including the availability of various subassemblies within the system as well as the nature of the particular sample to be processed.

In step 1470, a central processor may generate a list of all samples that can be scheduled. A sample can be scheduled if sample related work instructions are available. Then, the sample list is grouped into priority groups (step 1472). For example, a sample list may contain a first STAT sample that has a processing time of 10 minutes, a second STAT sample that has a processing time of 20 minutes, a third non-STAT sample that has a processing time of 15 minutes and a fourth non-STAT sample that has a processing time of 9 minutes. The samples may be grouped into two groups: STAT and non-STAT. Within these groups, the samples are sorted according to increasing slack time (the slack time may alternatively be referred to as an aging time, or the time that the sample has been in the distribution area) or the shortest processing time through the laboratory automation system (step 1474). With reference to the previous example, the samples may be sorted as follows according to the shortest processing time. For the STAT samples, the prioritization would be the first STAT sample and the second STAT sample. For the non-STAT samples, the prioritization would be the fourth non-STAT sample and the third non-STAT sample. The top three unscheduled tubes are then selected (step 1476). For example, in the above-noted example, the selected tubes may comprise the first STAT sample, the second STAT sample, and the fourth non-STAT sample. Although the top three tubes are selected in this example, more or less sample tubes may be selected in other examples.

In step 1478, a determination is then made as to whether there are any more samples to schedule. If not, then the list may be re-sorted with scheduled samples according to discharge time (step 1484). If so, then the next highest priority sample in the list is selected for processing (step 1486). As noted above, a STAT sample always has a higher priority than a non-STAT sample. In the above example, only the third non-STAT sample is unscheduled.

Then, the next available discharge time is determined (step 1488). The discharge time can be when the sample will be moved out of the distribution area. A preliminary schedule is then determined for the selected sample (step 1490).

Then, a determination is made as to whether the sample's resultant discharge time is greater than a pre-defined threshold time (step 1492). If the determination is positive, then the method proceeds to step 1482. In step 1482, the preliminary schedule is discarded for the selected sample. In step 1480, the selected sample is marked as not to be scheduled until a pre-defined threshold time before its discharge time. The method then proceeds to step 1478.

If the sample's resultant discharge time is not greater than the pre-defined threshold time, then an empty carrier is requested to the track location needed by the selected sample (step 1494). If the carrier request can be satisfied (step 1502), then the system can commit to the preliminary schedule for the selected sample (step 1506), and the method can loop back to step 1478 to determine if there are any more samples to schedule.

If the carrier request cannot be scheduled, then the preliminary schedule for the selected sample is discarded (step 1500). The discharge time may then be delayed by the pre-defined hold time (step 1498). Then, a determination is made as to whether the selected sample's resultant discharge time is greater than a pre-defined threshold time (step 1496). If the determined resultant discharge time is not greater than the pre-defined threshold time, then the method proceeds to step 1490. If the determined resultant discharge time is greater than the predetermined threshold time, then selected sample is marked as not to be scheduled until a pre-defined hold time from the present time (step 1504). The method can then proceed to step 1478.

In some embodiments, a sample is sent to a track only if the required resources are available. If prioritization is equal for all samples, the first sample in the distribution area 204 is sent to the conveyance system 220 (e.g., track).

Conventional systems may use bypass lanes for buffers (e.g., US 2012179405A1) or queue jumping (e.g., US 2011112683A1) or random access buffers beside the track (e.g., U.S. Pat. No. 7,681,466B2). Embodiments of the invention have advantages over such conventional systems. Such advantages include reduced hardware (e.g., fewer buffers and queues). Also, embodiments of the invention have better random access to sample containers since they are not constrained by being present in a buffer or queue.

Referring again to FIG. 14(*a*), in an illustrative workflow, the scheduler plans a schedule for the sample tube, based on the sample processing priority, the liquid level and barcode, tube, and cap characteristics analysis information, as indicated at operation 1418. At operation 1420, when the sample tube is the next tube to be transferred, a distribution area gripper 218 deposits the sample tube at one of the centrifuge adapter 1002, an error area 222 (which may be an output drawer), or at the conveyance system 220. With changes to certain subsystems, the current instrument can make full use of the drawer that housed the SIQ racks. Therefore, full racks can be used on this drawer which makes it function like a normal output area.

As shown in FIG. 14(*b*), when the scheduler selects a sample for centrifugation, the tube may be loaded by the distribution area gripper 218 into the appropriate centrifuge adapter 1002 at the centrifuge load position 1004 to ensure a balanced centrifuge rotor. At operation 1422, if the sample is selected for centrifugation, the tube is transported by distribution area gripper 218 from distribution area 204 to the centrifuge adapter 1002, as indicated at operation 1424.

In embodiments of the invention, the sample level of a sample in a sample tube may be determined after taking a picture of the sample tube with a movable assembly comprising a gripper unit and a camera. Other embodiments use an absorption using a transmission measurement device having multiple light sources having wavelengths capable of passing through labels but may or may not be affected by the sample media. After passing through the labels and sample the light is detected with a photoelectric sensor(s). The various sample media can block none, some or all of the light emitting from the LEDs. As a result, the sample layer heights can be determined and measured. Further details regarding this embodiment are provided below.

The weight of the sample tube may be calculated by an image analysis device while the sample is being moved. The volume of the sample can be calculated from the layer heights coupled with geometric properties of the tube determined from an analysis of the image captured by the camera in the robot. The weight calculation begins after the image and layer information are obtained. The weight of the sample is calculated from the sample layer volumes and density estimates for the contents which are archived in a system software database. The sample weight is combined with the weight of the sample container which was also previously archived in a system software database. This combined weight is used by the system's software to determine which centrifuge adapter position in which to deposit the sample tube to ensure a balanced centrifuge rotor. The camera can also take a picture of a centrifuge adapter and can determine which locations in the centrifuge adapter can be filled in a manner that allows the centrifuge to be balanced once other centrifuge adapters are filled. For example, centrifuge adapters that will be placed opposite to each other in the centrifuge may each be loaded with a plurality of sample tubes that collectively weigh the same.

As the centrifuge cycle is ending for adapters already loaded into the centrifuge 206-1 or 206-2, the newly loaded centrifuge adapters 1002 are moved to the appropriate centrifuge 206-1 or 206-2. The adapters sit on an adapter shuttle 224 that moves from centrifuge load position 1004, between the manager unit 700 and the centrifuge unit 804, to the appropriate centrifuge 206-1 or 206-2, as indicated at operation 1426. The adapter may be loaded by centrifuge module gripper 226 into a centrifuge bucket, as indicated at operation 1428. The sample is centrifuged, as indicated at operation 1430. The adapter is removed from the centrifugation bucket, as indicated at operation 1432. The adapter is transferred to an unloading area, as indicated at operation 1434, the sample tube is removed from the adapter by centrifuge module gripper 226, as indicated at operation 1436, and the sample tube is placed by centrifuge module gripper 226 into a carrier on conveyance system 220, as indicated at operation 1438.

Newly loaded centrifuge adapters 1002 are swapped with the adapters in the centrifuge unit 206-1 or 206-2 by centrifuge module gripper 226. During the first step of the swap, the centrifuged adapters are removed from the centrifuge unit 206-1 or 206-2 and placed onto specific spots on the shuttle so that when the shuttle returns to the manager unit 700, the tubes can be unloaded by centrifuge module gripper 226 from the adapters and placed onto the conveyance system 220. The newly loaded adapters 1002 from the manager unit 700 are placed inside the centrifuge 206-1 or 206-2. The adapters which were previously emptied of tubes are moved by the centrifuge module gripper 226 from the unloading spots on the shuttle 224 to spots on the shuttle where they can be loaded with tubes in the manager unit 700.

While adapters are being swapped in the centrifuge unit 804, the scheduler may direct tubes that do not require centrifugation to be moved by the distribution area gripper 218 from the distribution area 204 to the conveyance system 220, bypassing the centrifugation unit 804, as indicated at operation 1440. This can occur anytime the scheduler determines it is best to advance a tube from the distribution area 204 to the conveyance system 220. This depends upon the priorities and processing requirements of samples in the distribution area and downstream processing availability.

The scheduler determines the appropriate tubes to select from the distribution area 204 and the centrifuge adapters 1002 being unloaded to the conveyance system 220 to ensure the proper flow of samples downstream. The centrifuge adapters can be unloaded to ensure that the next centrifuge cycle can begin on time. This is dependent upon downstream process availability.

When the samples are loaded onto the conveyance system 220, distribution area gripper 218 aligns the barcode of the tube with the carrier used to carry the tube on the conveyance system 220. The carrier orientation is maintained on the conveyance system, simplifying the barcode reading process at downstream processes.

As shown in FIG. 14(*c*), once the tube is in the carrier on the conveyor system 220, the decapper 710 may remove the cap on the sample tube if the sample requires decapping, as indicated at operations 1446 and 1448. The samples that have been decapped may have their serum indices measured in the serum indices unit 210 if a serum index is required for the sample, as indicated at operations 1450 and 1452.

In certain circumstances, samples may need to be divided into more than one sample tube. These sample tubes may exit the conveyance system 220 of the pre-analytical phase and enter the aliquotter unit 212 at the primary tube queue 1104 if aliquotting is required, as indicated at operations 1454 and 1456. The samples are divided into secondary tubes at the direction of the scheduling system. Before the aliquotting is performed by the pipetting robot 302, empty secondary tubes are provided by the secondary tube lift 318 into carriers in the secondary tube queue 1106, as indicated at operation 1458. Part of the sample is transferred from a primary tube 304 into a secondary tube 306 by pipetting robot 302, as indicated at operation 1460. The primary and new secondary tubes then leave the aliquotter unit 212 and reenter the conveyance system 220, as indicated at operation 1462.

As shown in FIG. 14(*d*), once any necessary centrifugation, decapping, or aliquotting is performed, and once the sample is ready to be analyzed, the sample tube may continue to the analytical phase along conveyance system 220 if further analysis is required, as indicated at operations 1464 and 1466, or may be moved by an output/sorter gripper 404 to output racks located in the drawers of the output/sorter unit 214, as indicated at operation 1468.

It will be recognized that a plurality of grippers may be used for the functions described as being performed by any single gripper. The functionality described for each gripper may be combined and performed by one or more gripper.

II. Robotic Arms and Grippers

As discussed above, a robotic arm can be used to move a sample tube or any other object (e.g. a centrifuge adapter) from many different locations within the laboratory system (e.g., input robot 228, distribution robot 218, centrifuge robot 226, decapper robot 710, aliquotter robot 302, output/sorter robot 404, recapper robot 504, secondary tube lift, etc.).

Figure 15:
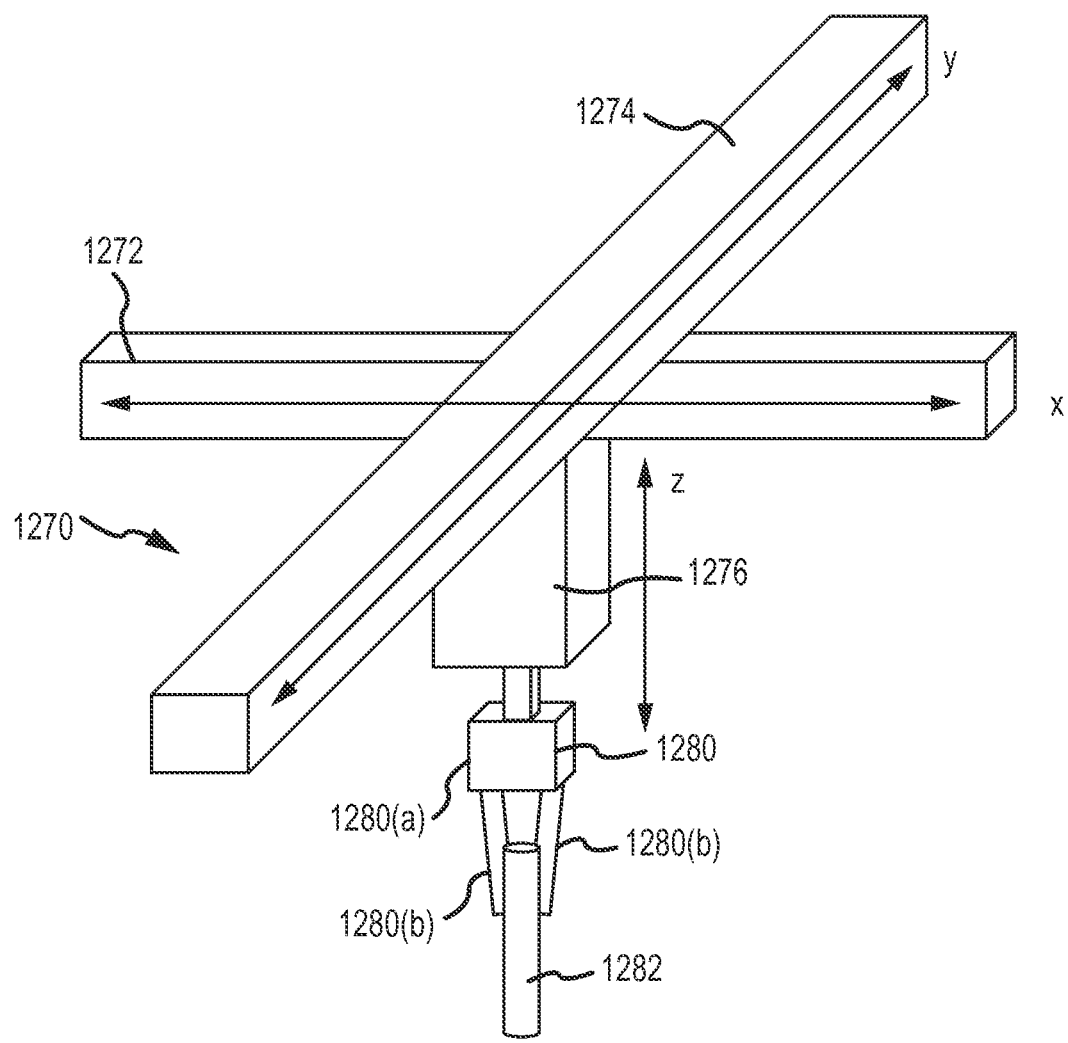
FIG. 15 depicts an example of a Cartesian or gantry robot with three independently moveable directions x-, y-, and z-.

The robotic arm architecture can differ in complexity dependent upon the given task. FIG. 15 depicts an example of a Cartesian or gantry robot 1270 with three independently moveable directions x-, y-, and z-. The x-axis may be defined by an x-axis rail 1272 and the y-axis may be defined by a y-axis rail 1274. The z-axis may be defined by an orientation of a robotic arm 1276 extending in the z-direction. The gantry robot 1270 comprises a robotic arm 1276, and a gripper unit 1280 operatively and physically coupled to the robotic arm 1276. More complex robotic arms may include, for example, the Selective Compliant Assembly Robot Arm (SCARA) or the articulated robotic arm with multiple joint arms. The gripper unit 1280 comprises a gripper housing 1280(a) and gripper fingers 1280(b) extending downward from the gripper housing 1280(a). The gripper fingers can move inwardly towards each other to grip a sample tube 1282 and outwardly to release a sample tube 1282.

The robotic arm including the gripper unit can be additionally employed for identification and for determination of physical characteristics of the moved object. Therefore, the robotic arm can be equipped with an appropriate identification and determination means (e.g., a camera, a bar code reader, or an absorption and transmission measurement unit). The tube identification, level detection, and tube presence detection units are described in more detail below.

The following description of a tube handling unit, a centrifuge adapter gripper, a tube identification device, a sample level detection device, tube or rack presence detection device, and a combination of these functions in a single robot arm will be discussed in light of the gantry robotic arm depicted in FIG. 15.

A. Tube Handling Units

Figure 16C:
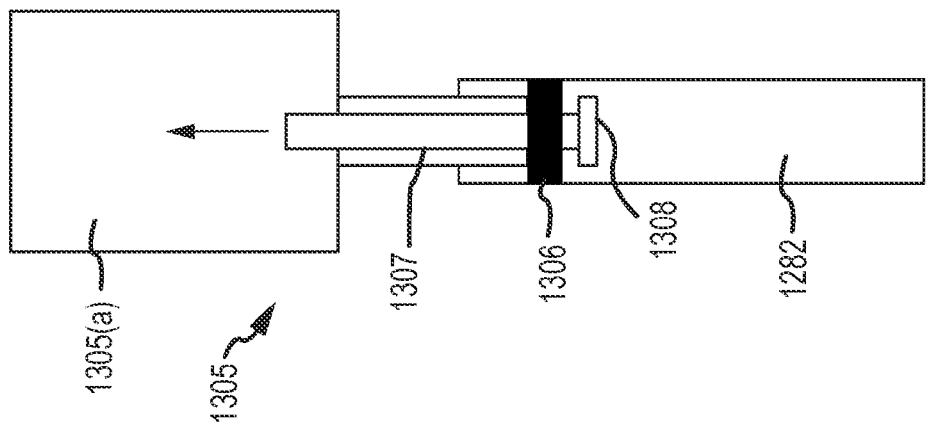
FIGS. 16(a)-(c) depict side-view diagrams of embodiments of gripper units.
Figure 16B:
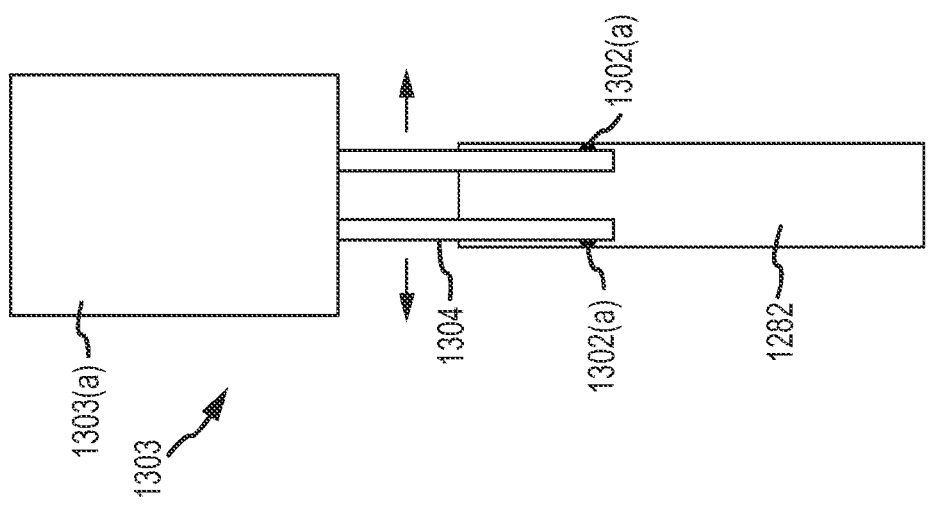
Figure 16A:
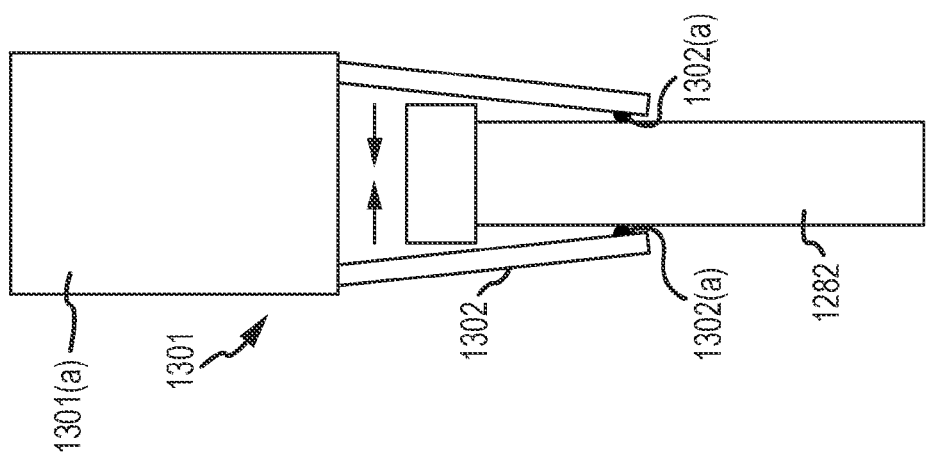

The robotic arms according to embodiments of the invention may employ a gripper unit to grip and transport sample tubes to desired locations. FIGS. 16(a)-16(c) depict several different gripper units to grip and transport sample tubes to desired locations.

FIG. 16(a) depicts an example for a gripper unit 1301 for sample tubes comprising a gripper housing 1301(a) comprising two or more moveable fingers 1302 extending downward and comprising inwardly projecting contact structures 1302(a). The inwardly projecting contact structures 1302(a) grip a sample tube 1282 by a movement towards the outer wall of the tube 1282.

FIG. 16(b) depicts an example for an inside gripper unit 1303 comprising a gripper housing 1303(a) comprising two or more fingers 1304 extending downward from the gripper housing 1303(a). In this embodiment, the two or more fingers 1304 move outwards toward the inner wall of a sample tube 1282.

Another embodiment of an inside gripper unit 1305 is depicted in FIG. 16(c). The gripper unit 1305 employs a flexible ring element 1306 which extends radially from a linear carrier 1307 to grip an inside surface of a sample tube 1282. The linear carrier 1307 extends from a gripper housing 1303(a). The flexible ring element (e.g., silicon O-ring) 1306 is compressed by moving the lower plunger segment 1308 of the linear carrier 1307 upwards.

B. Centrifuge Bucket Gripper

A robotic arm with a mechanical gripper unit as shown in FIGS. 16(a)-(c) may be a combined gripper capable of gripping samples tubes as well as centrifuge buckets and/or adapters used in the centrifuge module 206. As described above, the centrifuge buckets and adapters are containers used to hold sample tubes ready to be centrifuged. The centrifuge buckets may be the actual buckets that are placed in and part of the centrifuge. Additionally, centrifuge adapters may be used in conjunction with the centrifuge buckets. Centrifuge adapters are removable centrifuge cartridges that can be placed into the centrifuge bucket that is attached to the centrifuge rotor. The robotic arm is capable of picking up and transporting both a centrifuge bucket and a centrifuge adapter. For example, centrifuge buckets and/or adapters that are loaded with sample tubes ready to be centrifuged are transported from the distribution area 204 to the centrifuge module 206 via a shuttle 224. The centrifuge buckets and/or adapters are loaded into the centrifuge, after which the samples can be centrifuged.

The gripper unit may perform several functions, including picking up sample tubes at an input area 202, transporting sample tubes to a loading position 1004 for an empty centrifuge bucket, placing sample tubes in a free position of the centrifuge bucket, choosing a completely filled centrifuge bucket, transporting the centrifuge bucket to an available centrifuge, placing the centrifuge bucket in a free position of the centrifuge rotor, choosing a centrifuged bucket, transporting a centrifuged bucket to an unloading position for a centrifuged bucket, picking up centrifuged sample tubes in the centrifuged bucket, etc.

In one embodiment of the robotic gripper arm for use as a sample tube and bucket gripper, an adapter tool can be used with the combined robotic gripper. The adapter tool can be used by the robotic gripper to hook in the centrifuge buckets.

In another embodiment, a bucket lift can be allocated within the body of the centrifuge underneath the unloading position for the buckets. By moving the lift up, the buckets may be transported to the top of the centrifuge to be further processed. A sample tube gripper robot may then grip the centrifuge buckets with the standard gripper unit or an adapter tool as described above.

In another embodiment, a single sample tube gripper can be applied to a telescopic robotic arm. The sample tube gripper unit may be moved down into the centrifuge body using the telescopic robotic arm. The sample tube gripper robot may then grip the centrifuge buckets with its standard gripper unit.

In another embodiment, a centrifuge bucket gripper unit can be applied to the telescopic robotic arm in addition to a standard sample tube gripper.

E. Sample Level Detection

In addition to the tube identification and tube or rack presence detection features described above, the camera unit and analysis tool can use the 2-D image captured by the system to determine a sample volume and sample level for the sample in the sample tube.

Figure 17:
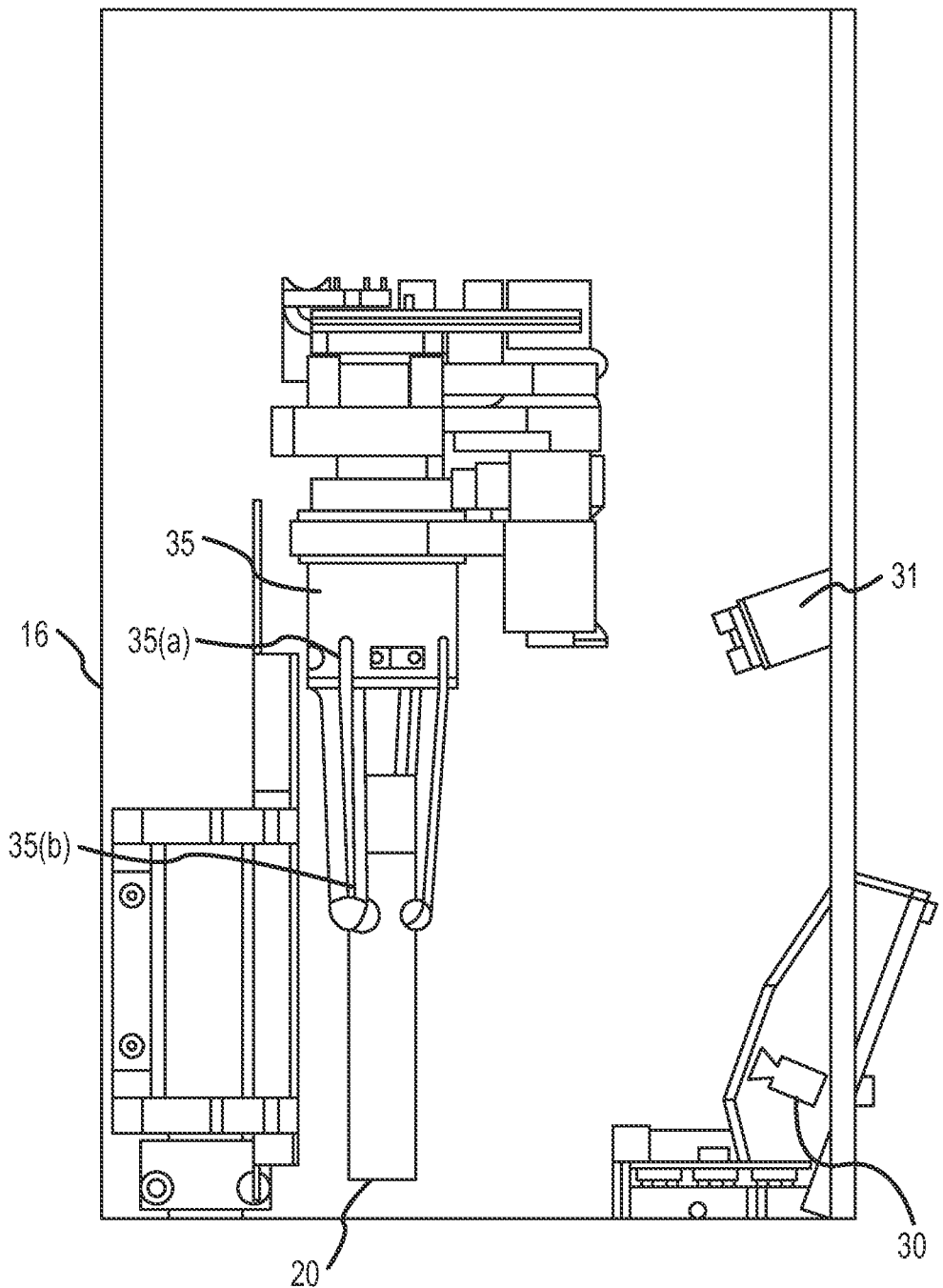
FIG. 17 depicts a side-view diagram of a sample level detection unit and a sample tube.

A sample level detection unit (or assembly) and a sample tube are depicted in FIG. 17. The sample level detection unit includes a chamber 16. A camera unit 30 is accommodated in the chamber 16, which has few and, if possible, no optical reflections. The camera unit 30 can be aligned with and focused on the sample tube 20 containing fluid. An illumination source 31 may provide light to the sample tube 20 so that the camera unit 30 can take a picture of the sample tube 30.

The camera unit 30 can be a still camera, a color image camera, a video camera, a spectral camera or the like. A color image camera, for example a 3CCD video camera, may be used. The settings of the color camera, such as focusing, white balance, diaphragm setting, filling-in, can be permanently preset or adjustable. For example, they can be adjusted with the aid of image evaluation software, as in when the data reported by the image evaluation software to the control software are of reduced quality with reference to store reference data. An algorithm can be used to calculate the sample level and/or volume using known data, such as the type of sample tube used, the type of sample, etc.

As shown in FIG. 17, the camera unit 30 can be inclined to optimize its view of the sample tube 20. The sample tube 20 information can be recorded with comparatively few optical reflections with the aid of this measure.

Arranged above and in the middle relative to the analysis position of the sample tube is a gripper unit 35 that is controlled by a computer. The gripper unit 35 grips the sample tube 20 located in a rack of the input section and lifts it into the analysis position. The gripper unit 35 can comprise a gripper housing 35(a), and a plurality of gripper fingers 35(b), which can be used to grip the sample tube 20.

As an alternative to the liquid level detection device using a camera unit, the liquid level detection may also be accomplished by the use of another type of image acquisition device such as a device that has laser diodes with a defined wavelength and analysis algorithms to evaluate the absorption spectra. A laser diode beam can be focused on sections of the sample tube, and an absorption and transmission measurement of different wavelengths of the focused beam can be measured. The analysis algorithm can then use the measurements to provide the liquid level and volume.

Figure 18:
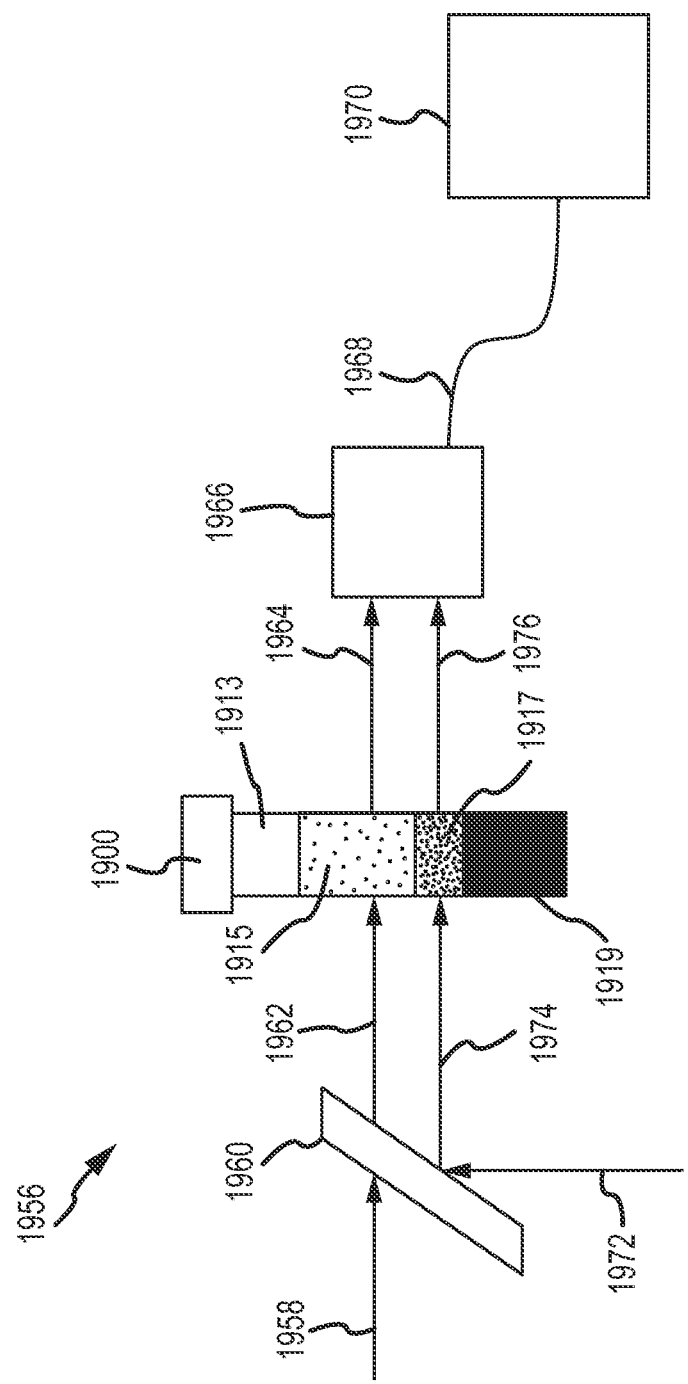
FIG. 18 depicts a block diagram of sample level detection utilizing the analysis of absorption and transmission curves at distinct wavelengths.

FIG. 18 depicts an example of sample level detection utilizing the analysis of absorption and transmission curves at distinct wavelengths. In instances in which blood samples are provided with the sample tube container, the system may additionally be able to detect the distinct levels of serum, plasma, or blood-cake in the sample.

In FIG. 18, a portion of an operable fluid sample interrogation system is depicted generally at 1956. A first source of radiation 1958 (with a second source of radiation 1972 turned off) is arranged to apply a first radiation having a first characteristic wavelength (e.g., 980 nm) to beam combiner 1960, which directs the first emitted radiation 1962 toward a location on the sample tube 1900. The first transmitted radiation 1964 is detected by a detector, such as illustrated photo diode and amplifier arrangement 1966. The detector may be an example of at least a part of an image acquisition device. A signal 1968, corresponding to the intensity of first transmitted radiation 1964 can then be stored and/or manipulated in comparison structure, such as programmable integrated circuit 1970, or a computer. The second source of radiation 1972 (with the first source of radiation 1958 turned off) is arranged to apply a second radiation having a second characteristic wavelength (e.g., 1050 nm) to beam combiner 1960 at a slightly shifted position as the first emitted radiation 1962, which directs the second emitted radiation 1974 parallel to the beam path of first emitted radiation 1962 toward a slightly different location on the sample tube 1900. The second transmitted radiation 1976 is detected by the same detector, such as illustrated photo diode and amplifier arrangement 1966. A signal 1968, corresponding to the intensity of second transmitted radiation 1976 can then be stored and/or manipulated in comparison structure, such as programmable integrated circuit 1970, or a computer.

FIG. 18 further depicts a sample tube that is being measured and analyzed using the wavelength process. As shown, serum 1915 and gel 1917 are mostly transparent to visible light while red blood cells 1919 are substantially opaque. Further, gel 1917 is transparent to infrared light while red blood cells 1919 and serum 1915 are substantially opaque. Accordingly, when the sample tube 1900 has gel 1917 to separate the serum 1915 and red blood cells 1919, it is possible just using infrared light to "see through" different sections. The infrared light reading is strong when the infrared light beam passes through air 1913, drops when the infrared light beam is directed toward the serum, is relatively strong when directed toward the gel 1917, and drops again when directed toward the red blood cells 1919. This analysis performed by the analysis tool allows for the measurement of the sample level/volume of the sample.

The liquid level detection unit can be combined with any of the above-described robotic arms with or without a tube identification unit, and with or without a tube or rack presence detection unit. Further details regarding tube identification units and tube or rack presence detection units can be found in U.S. Provisional Patent Application Nos. 61/556,667, 61/616,994, and 61/680,066.

F. Combination Robot with Gripper, Tube Identification Unit, Tube or Rack Presence Detection Unit and Liquid Level Detection Unit A combination robot with gripper, tube identification unit, tube or rack presence detection unit and liquid level detection unit can be utilized by the laboratory automation system. The combination robot utilizes the features of the gripper robot described above and a camera of the tube identification unit, a camera of the tube or rack presence detection unit and laser diodes for sample level detection described above.

Figure 19:
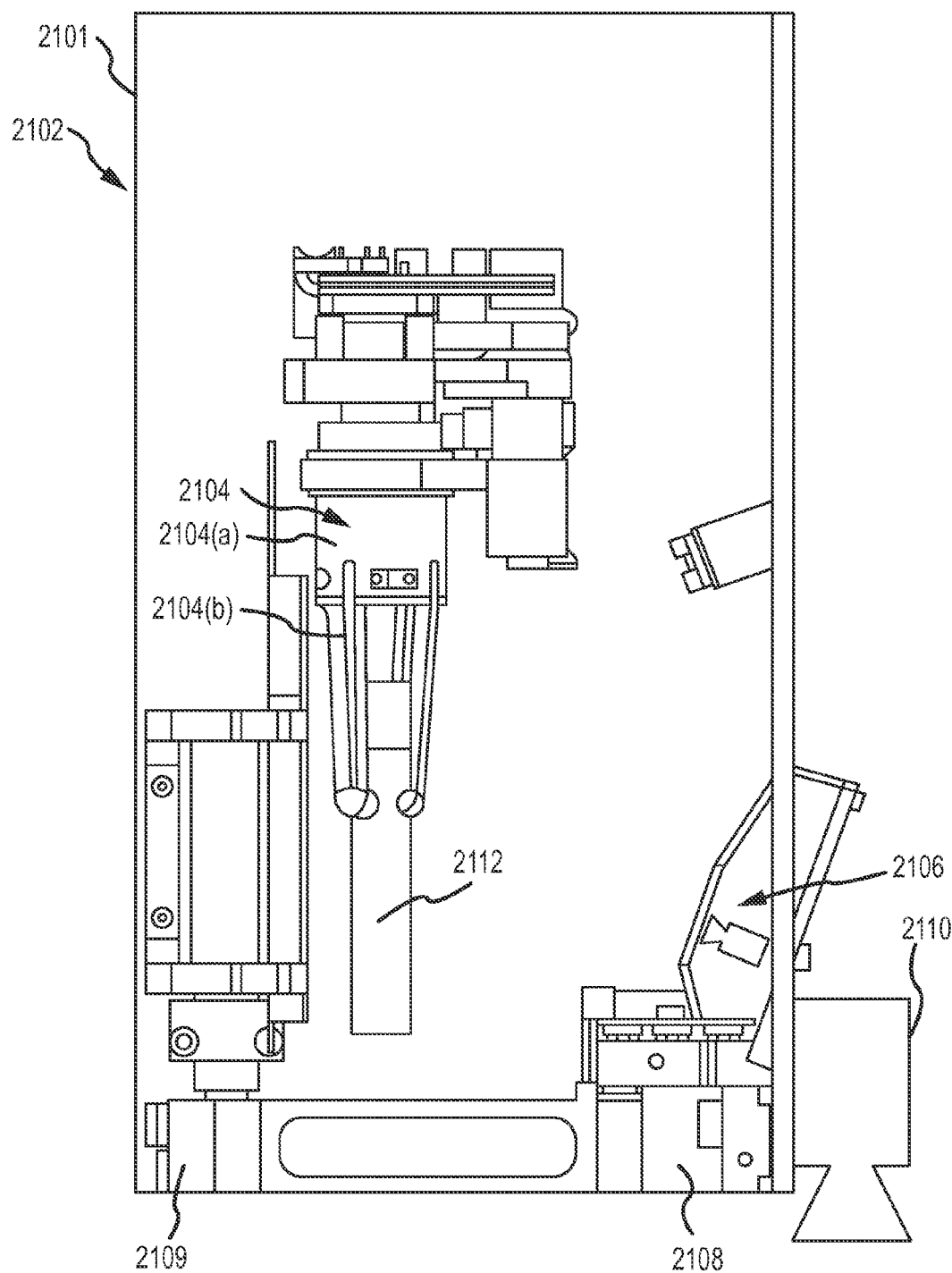
FIG. 19 depicts a block diagram of a combination robot.

FIG. 19 depicts a schematic drawing of one example of the combination robot (or assembly). The combination robot 2102 can include a robotic gripper 2104 for gripping sample tubes, disposed in a chamber 2101. The robotic gripper 2104 may comprise a gripper housing 2104(a) with gripper fingers 2104(b) extending downward and gripping a sample tube 2112. The combination robot 2102 can utilize a camera 2106 for acquiring images to perform tube detection and/or sample level detection. The combination robot 2102 can also utilize an emitter 2108 and a receiver 2109 for performing laser diode sample level/volume detection. The combination robot 2102 can also utilize a tube or rack presence detection camera 2110 for acquiring a series of images during the x-y movement of the gripper to perform tube and rack presence detection and tube and rack identification. Tube and rack presence detection and tube and rack identification systems and methods are described in further detail in U.S. Provisional Patent Application No. 61/556,667, filed Nov. 7, 2011, U.S. Provisional Patent Application No. 61/616,994, filed Mar. 28, 2012, and U.S. Provisional Patent Application No. 61/680,066, filed Aug. 6, 2012, which are herein incorporated by reference in their entirety for all purposes.

Figure 20:
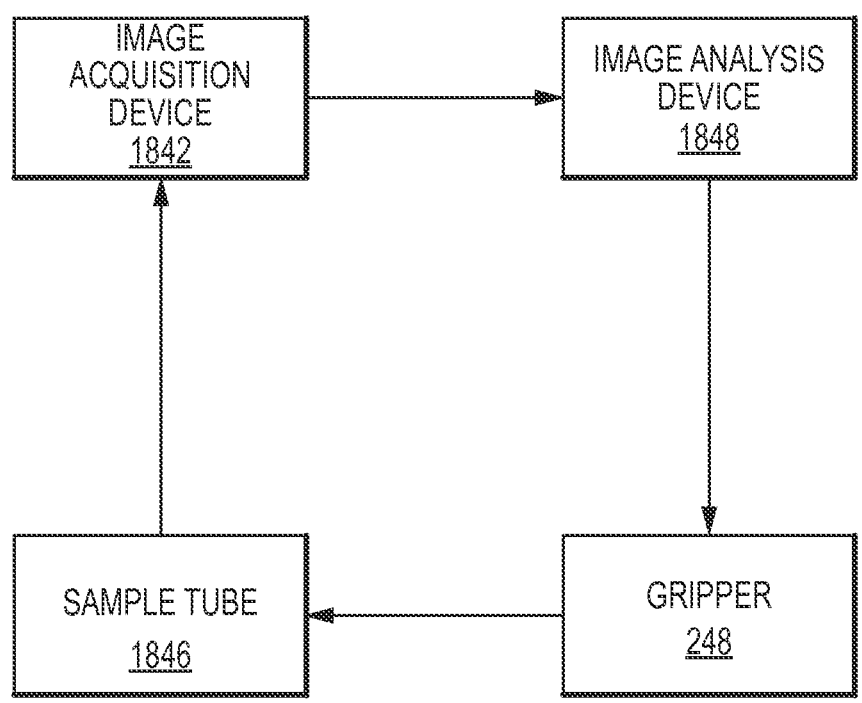
FIG. 20 shows a block diagram of some components of a system using a robotic arm with an image acquisition device.

FIG. 20 shows a high-level block diagram of some components in a sample tube and rack identification system according to an embodiment of the invention. FIG. 20 shows an image acquisition device 1842 coupled to an image analysis device 1848. The image analysis device 1848 can also be coupled to a gripper unit 248 and can provide instructions to it. The gripper unit 248 can then secure a specific sample tube 1846.

Suitable image acquisition devices may include cameras, as well as detectors like those described with reference to FIG. 18.

Although the instructions provided by the image analysis device 1848 are provided to a gripper unit 248 in this example, embodiments of the invention are not limited thereto. For example, embodiments of the invention can provide instructions to a central controller in the laboratory automation system to inform other downstream instruments or subsystems that a particular tube has been identified and/or that the sample tube is of a particular weight. For example, once a particular sample tube in a sample rack has been identified, a scheduler in a central controller will know where that particular sample tube is in the system and can plan ahead for any subsequent processing. Thus, the instructions and/or analysis data provided by the image analysis device 1848 may be provided to any suitable downstream instrument or subsystem.

Figure 21:
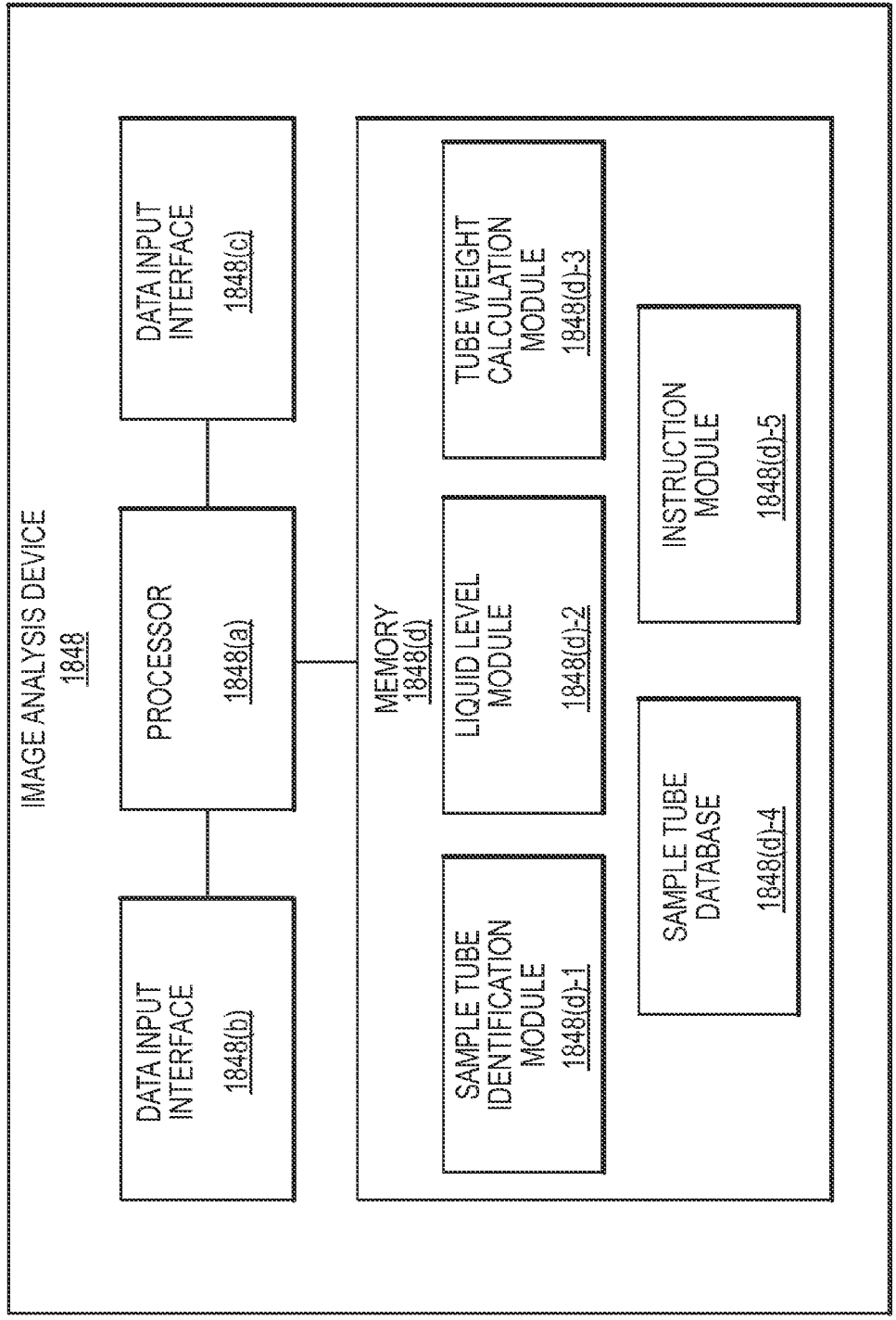
FIG. 21 shows a block diagram of an image analysis device.

FIG. 21 shows a block diagram of an image analysis device 1848 according to an embodiment of the invention. It may include a data input interface 1848(*b*) to receive data from the one or more image acquisition devices (e.g. image acquisition device 1842), and a processor 1848(*a*) coupled to the input interface 1848(*b*). The processor 1848(*a*) may also be coupled to a data output interface 1848(*c*) which provides data to suitable devices which can manipulate and/or transport a sample tube 1848(*c*). The processor 1848(*a*) may further be coupled to a memory 1848(*d*) which may comprise a sample tube identification module 1848(*d*)-1, a liquid level determination module 1848(*d*)-2, a tube weight calculation module 1848(*d*)-3, a sample tube database 1848(*d*)-4, and an instruction module 1848(*d*)-5. The sample tube identification module 1848(*d*)-1 may comprise computer code, executable by the processor 1848(*a*), to determine the identity of a sample tube. A sample tube can be identified, for example, by a barcode on the sample tube, a cap color, a tube shape, etc. The liquid level determination module 1848(*d*)-2 may comprise computer code, executable by the processor 1848(*a*) to determine a liquid level of a sample in a sample tube. The tube weight calculation module 1848(*d*)-3 may comprise computer code, executable by the processor 1848(*a*) to calculate the weight of a sample tube. The sample tube database 1848(*d*)-4 may have information relating to sample tubes. The sample tube instruction module 1848(*d*)-5 may comprise code, executable by the processor 1848(*a*) to provide instructions to an external device via the data output interface 1848(*c*). The instructions that are provided may include instructions to a gripper unit, which cause the gripper unit to transport the sample tube to a particular location or a particular subsystem after identifying the sample tube. Note that any of the previously described software modules may function independently or together. For instance, the sample tube identification module 1848(*d*)-1 may operate with the liquid level module 1848(*d*)-2 and the sample tube weight calculation module 1848(*d*)-3 to identify the particular sample tube and to calculate a weight of the sample tube.

The sample tube database 1848(*d*)-4 may comprise any suitable type of information relating to sample tubes. It may include, for example, sample tube information correlating samples to sample tube characteristics, markers or labels on a sample tube. The sample tube database 1848(*d*)-4 may also include information regarding different types of sample tubes and their corresponding volumes and weights (without a sample in it). This information, along with information about the level of a sample if a tube, can be used to calculate the weight of a sample tube.

In methods according to embodiments of the invention, at least one camera acquires at least one picture of the rack with sample tubes comprising samples. The method further comprises analyzing, by the image analysis device, the at least one picture to identify characteristics of the sample tubes and/or rack. If the sample tubes comprise different samples, then these samples may be in different sample tubes with different characteristics, and the samples may be processed differently, after they have been identified. For example, after receiving instructions from the analysis device, a first sample tube with a first characteristic and a first sample could be sent to a storage unit by a gripper (coupled to a robotic arm) that is capable of moving in three directions (X, Y, and Z), while a second sample tube with a second characteristic and a second sample may be sent to a centrifuge, prior to being analyzed.

The processor 1848(*a*) may comprise any suitable data processor for processing data. For example, the processor may comprise one or more microprocessors that function separately or together to cause various components of the system to operate.

The memory 1848(*d*) may comprise any suitable type of memory device, in any suitable combination. The memory 1848(*d*) may comprise one or more volatile or non-volatile memory devices, which operate using any suitable electrical, magnetic, and/or optical data storage technology.

VII. Computer Architecture

The various participants and elements described herein with reference to the figures may operate one or more computer apparatuses to facilitate the functions described herein. Any of the elements in the above description, including any servers, processors, or databases, may use any suitable number of subsystems to facilitate the functions described herein, such as, e.g., functions for operating and/or controlling the functional units and modules of the laboratory automation system, transportation systems, the scheduler, the central controller, local controllers, etc.

Examples of such subsystems or components are shown in FIG. 22. The subsystems shown in FIG. 22 are interconnected via a system bus 4445. Additional subsystems such as a printer 4444, keyboard 4448, fixed disk 4449 (or other memory comprising computer readable media), monitor 4446, which is coupled to display adapter 4482, and others are shown. Peripherals and input/output (I/O) devices, which couple to I/O controller 4441 (which can be a processor or other suitable controller), can be connected to the computer system by any number of means known in the art, such as serial port 4484. For example, serial port 4484 or external interface 4481 can be used to connect the computer apparatus to a wide area network such as the Internet, a mouse input device, or a scanner. The interconnection via system bus allows the central processor 4443 to communicate with each subsystem and to control the execution of instructions from system memory 4442 or the fixed disk 4449, as well as the exchange of information between subsystems. The system memory 4442 and/or the fixed disk 4449 may embody a computer readable medium.

Embodiments of the technology are not limited to the above-described embodiments. Specific details regarding some of the above-described aspects are provided above. The specific details of the specific aspects may be combined in any suitable manner without departing from the spirit and scope of embodiments of the technology. For example, back end processing, data analysis, data collection, and other processes may all be combined in some embodiments of the technology. However, other embodiments of the technology may be directed to specific embodiments relating to each individual aspect, or specific combinations of these individual aspects.

It should be understood that the present technology as described above can be implemented in the form of control logic using computer software (stored in a tangible physical medium) in a modular or integrated manner. Furthermore, the present technology may be implemented in the form and/or combination of any image processing. Based on the disclosure and teachings provided herein, a person of ordinary skill in the art will know and appreciate other ways and/or methods to implement the present technology using hardware and a combination of hardware and software.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the technology will become apparent to those skilled in the art upon review of the disclosure. The scope of the technology should, therefore, be determined not with reference to the above description, but instead should be determined with reference to the pending claims along with their full scope or equivalents.

One or more features from any embodiment may be combined with one or more features of any other embodiment without departing from the scope of the technology.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of transporting a sample container for analysis by a laboratory automation system, comprising:
   transporting a sample container containing a sample from an input area to a distribution area by a gripper comprising a means for inspecting a tube;
   obtaining data during the transporting of the sample container, wherein the obtaining the data comprises,
      capturing an image of the sample container, analyzing the image to determine at least one physical characteristic of the sample container, and determining a sample container identification of the sample container based on the at least one physical characteristic,
      determining a liquid level of the sample in the sample container, and
      calculating a weight of the sample container using the sample container identification and the liquid level;
   requesting a sample schedule associated with the sample in the tube, wherein the sample schedule is requested from a scheduling system based on the data obtained during the transporting;
   determining by the scheduling system a time when the tube containing the sample should be processed; and
   transporting the tube from the distribution area to a subsequent processing module in the laboratory automation system at the time determined by the scheduling system.

2. An assembly comprising:
   a robotic arm having a gripper unit configured to grip a sample container, wherein the robotic arm is configured to move in three dimensions;
   an image acquisition device physically coupled to the robotic arm and configured to acquire an image of the sample container, wherein the image acquisition device comprises a camera and a liquid level optical detection device comprising an optical emitter and an optical detector, wherein the liquid level detection device comprises
      a first source of radiation configured to apply a first radiation having a first characteristic wavelength to a beam combiner, which is configured to direct the first radiation towards a location on the sample container,
      a second source of radiation configured to apply a second radiation having a second characteristic wavelength to the beam combiner at a slightly shifted position as the first radiation, wherein the beam combiner is configured to direct the second emitted radiation parallel to the beam path of the first radiation towards a slightly different location on the sample container,
      a detector capable of detecting a first transmitted radiation, which comprises the first radiation transmitted through the sample container, and the second transmitted radiation, which comprises the second radiation transmitted through the sample container,
      a comparison structure for storing and/or manipulating both the intensity of first transmitted radiation and the intensity of the second transmitted radiation; and
   an image analysis device in communication with the image acquisition device, wherein the image analysis device is configured to analyze the image of the sample container to determine identifying information associated with the sample container and to determine a liquid level of a sample in the sample container via a transmission measurement, wherein the sample container is positioned between the optical emitter and the optical detector when the liquid level of the sample in the sample container is determined by the image analysis device.

3. The assembly of claim 2, wherein the transmission measurement is performed by the liquid level detection device.

4. The assembly of claim 2, wherein the optical emitter is configured to use multiple light sources having wavelengths capable of passing through labels but being absorbed by sample media comprised in the sample container.

5. The assembly of claim 2, wherein the liquid level detection device comprises laser diodes with different defined wavelengths, wherein the beams of the laser diodes are focused on sections of the sample container in order to allow for transmission measurements of different defined wavelengths.

6. The assembly of claim 2, wherein the liquid level detection device comprises light emitting diodes (LEDs) and the LEDs are selected such that various sample media comprised in the sample container block none, some or all of the light emitting from the LEDs, in order to make it possible via an analysis algorithm to determine and measure sample layer heights of a sample comprised in the sample container.

7. The assembly of claim 2, wherein the liquid level detection device comprises light sources emitting infrared light beams.

8. The assembly of claim 2, wherein the assembly comprises a tube presence detection unit capable of detecting the presence of a sample container in a rack.

9. The assembly of claim 2, wherein the image analysis device is further configured to calculate a weight of the sample container, while the sample container is being transported by the gripper unit.

10. An assembly comprising:
a robotic arm having a gripper unit configured to grip a sample container, wherein the robotic arm is configured to move in three dimensions;
an image acquisition device physically coupled to the robotic arm and configured to acquire an image of the sample container, wherein the image acquisition device comprises a camera and a liquid level optical detection device comprising an optical emitter and an optical detector, wherein the image acquisition device is a first image acquisition device, and wherein the assembly comprises a second image acquisition device configured to capture a second image of a plurality of sample containers, wherein the second image is analyzed to determine a second sample container in the plurality of sample containers to grip with the gripper unit, and wherein the assembly further comprises a third image acquisition device configured to capture the image of the sample container or a sample container rack under the third image acquisition device; and
an image analysis device in communication with the image acquisition device, wherein the image analysis device is configured to analyze the image of the sample container to determine identifying information associated with the sample container and to determine a liquid level of a sample in the sample container via a transmission measurement, wherein the sample container is positioned between the optical emitter and the optical detector when the liquid level of the sample in the sample container is determined by the image analysis device.

* * * * *